(12) United States Patent
MacKinnon et al.

(10) Patent No.: US 7,888,046 B2
(45) Date of Patent: Feb. 15, 2011

(54) VOLTAGE SENSOR DOMAINS OF VOLTAGE-DEPENDENT ION CHANNEL PROTEINS AND USES THEREOF

(75) Inventors: Roderick MacKinnon, New York, NY (US); Alice Lee MacKinnon, New York, NY (US); Youxing Jiang, Carrollton, TX (US); Vanessa Ruta, New York, NY (US)

(73) Assignee: The Rockefeller University, New York, NY (US)

( * ) Notice: Subject to any disclaimer, the term of this patent is extended or adjusted under 35 U.S.C. 154(b) by 178 days.

(21) Appl. No.: 12/141,367

(22) Filed: Jun. 18, 2008

(65) Prior Publication Data

US 2009/0075394 A1    Mar. 19, 2009

Related U.S. Application Data

(63) Continuation of application No. 10/377,139, filed on Mar. 1, 2003, now Pat. No. 7,405,052.

(51) Int. Cl.
*C07K 14/705* (2006.01)
*G01N 33/566* (2006.01)

(52) U.S. Cl. ................ 435/7.2; 436/501; 530/350

(58) Field of Classification Search ............. None
See application file for complete search history.

(56) References Cited

U.S. PATENT DOCUMENTS

| | | | |
|---|---|---|---|
| 5,368,712 A | | 11/1994 | Tomich et al. |
| 5,538,863 A | * | 7/1996 | Price .................... 435/69.1 |
| 2002/0187524 A1 | | 12/2002 | Curtis |
| 2005/0101767 A1 | | 5/2005 | Clapham et al. |
| 2005/0267009 A1 | | 12/2005 | Deagle |

OTHER PUBLICATIONS

Trainer et al. Neurotoxin Binding and Allosteric Modulation at Receptor Sites 2 and 5 on Purified and Reconstituted Rat Brain Sodium Channels, 1993, The Journal of Biological Chemistry 268(23):17114-17119.*
Ruta et al., "Functional Analysis of an Archaebacterial Voltage-Dependent K+ Channel", Nature, vol. 422, 180-185 (2003).
Schoenherr et al., "Conformational Switch Between Slow and Fast Gating Modes: Allosteric Regulation of Voltage Sensor Mobility in the EAG K+ Channel", Neutron 2002, 35(5):935-949.
Bezanilla, "The Voltage Sensor in Voltage-Dependent Ion Channels", Physiological Reviews, 80(2)555-592, Apr. 2000.
Lee et al., "Structure of the KvAP Voltage-Dependent K+ Channel and its Dependence on the Lipid Membrane", PNAS 102(43)15441-15446 (2005).
Ruta et al., "Localization of the Voltage-Sensor Toxin Receptor on KvAP+", Biochemistry, 43, 10071-10079 (2004).
Jiang et al., "X-Ray Structure of a Voltage-Dependent K+ Channel" Nature, 423, 33-41 (2003).
Jiang et al., "The Principle of Gating Charge Movement in a Voltage-Dependent K+ Channel", Nature, 423, 42-48 (2003).
Sigworth, "Life's Transistors", Nature, 423, 21-22 (2003).
Gregerson, "The Voltage Sensor of Ion Channels Revealed", Trends in Endocrinology and Metabolism, 14:6, 251-252 (2003).
Kawarabaysai, "Complete Gerome Sequence of an Aerobic Hyperthermophilic Crenarchaeon, Aeropyrum Pernix K1", DNA Research 6, 83-101 (1999).
Voges, "Recombinant Expression, Purification and Characterization of Kch, a Putative *Escherichia coli* Potassium Channel Protein", FEBS Letters, 429, 104-108 (1998).

* cited by examiner

*Primary Examiner*—John D Ulm
(74) *Attorney, Agent, or Firm*—Hoffmann & Baron, LLP

(57) ABSTRACT

A composition of matter suitable for use in identifying chemical compounds that bind to voltage-dependent ion channel proteins, the composition comprising a screening protein that comprises an ion channel voltage sensor domain of the ion channel protein immobilized on a solid support.

22 Claims, 4 Drawing Sheets

SEQUENCE LISTING

<160> NUMBER OF SEQ ID NOS: 21

<210> SEQ ID NO 1
<211> LENGTH: 295
<212> TYPE: PRT
<213> ORGANISM: Aeropyrum pernix

<400> SEQUENCE: 1

Met Ser Val Glu Arg Trp Val Phe Pro Gly Cys Ser Val Met Ala Arg
1               5                   10                  15

Phe Arg Arg Gly Leu Ser Asp Leu Gly Arg Val Arg Asn Ile Gly
            20                  25                  30

Asp Val Met Glu His Pro Leu Val Glu Leu Gly Val Ser Tyr Ala Ala
            35                  40                  45

Leu Leu Ser Val Ile Val Val Val Glu Tyr Thr Met Gln Leu Ser
50                  55                  60

Gly Glu Tyr Leu Val Arg Leu Tyr Leu Val Asp Leu Ile Leu Val Ile
65                  70                  75                  80

Ile Leu Trp Ala Asp Tyr Ala Tyr Arg Ala Tyr Lys Ser Gly Asp Pro
                85                  90                  95

Ala Gly Tyr Val Lys Lys Thr Leu Tyr Glu Ile Pro Ala Leu Val Pro
            100                 105                 110

Ala Gly Leu Leu Ala Leu Ile Glu Gly His Leu Ala Gly Leu Gly Leu
            115                 120                 125

Phe Arg Leu Val Arg Leu Leu Arg Phe Leu Arg Ile Leu Leu Ile Ile
    130                 135                 140

Ser Arg Gly Ser Lys Phe Leu Ser Ala Ile Ala Asp Ala Ala Asp Lys
145                 150                 155                 160

Ile Arg Phe Tyr His Leu Phe Gly Ala Val Met Leu Thr Val Leu Tyr
                165                 170                 175

Gly Ala Phe Ala Ile Tyr Ile Val Glu Tyr Pro Asp Pro Asn Ser Ser
            180                 185                 190

Ile Lys Ser Val Phe Asp Ala Leu Trp Trp Ala Val Val Thr Ala Thr
            195                 200                 205

Thr Val Gly Tyr Gly Asp Val Val Pro Ala Thr Pro Ile Gly Lys Val
    210                 215                 220

Ile Gly Ile Ala Val Met Leu Thr Gly Ile Ser Ala Leu Thr Leu Leu
225                 230                 235                 240

Ile Gly Thr Val Ser Asn Met Phe Gln Lys Ile Leu Val Gly Glu Pro
                245                 250                 255

Glu Pro Ser Cys Ser Pro Ala Lys Leu Ala Glu Met Val Ser Ser Met
            260                 265                 270

Ser Glu Glu Glu Phe Glu Phe Val Arg Thr Leu Lys Asn Leu Arg
            275                 280                 285

Arg Leu Glu Asn Ser Met Lys
    290                 295

<210> SEQ ID NO 2
<211> LENGTH: 283
<212> TYPE: PRT
<213> ORGANISM: Pseudomonas aeruginosa

<400> SEQUENCE: 2

Met Ser Ala Pro Asp Ser Trp Arg Glu Arg Leu Tyr Ile Val Ile Phe
1               5                   10                  15

-continued

```
Gln Thr Asp Thr Arg Asp Gly Arg Arg Phe Asp Ser Ala Leu Leu Leu
             20                  25                  30

Val Ile Leu Ala Ser Leu Leu Val Val Met Ile Asp Ser Ile Asp Glu
         35                  40                  45

Ile His Gln Asp Tyr Gly Asp Leu Leu Ala Tyr Ile Glu Trp Gly Phe
     50                  55                  60

Thr Gly Ile Phe Leu Val Glu Tyr Leu Arg Leu Tyr Cys Ser Pro
65                  70                  75                  80

Lys Pro Leu Arg Tyr Ala Phe Ser Phe Tyr Gly Leu Val Asp Leu Leu
                 85                  90                  95

Ala Ile Leu Pro Gly Phe Leu Ala Leu Leu Tyr Pro Asp Ala Gln Tyr
             100                 105                 110

Leu Leu Ile Val Arg Val Ile Arg Met Leu Arg Ile Phe Arg Val Leu
             115                 120                 125

Lys Leu Arg Gln Tyr Leu Ser Gln Ala Asn Phe Leu Leu Thr Ala Leu
         130                 135                 140

Arg Gly Ser Lys Gln Lys Ile Ile Val Phe Phe Leu Thr Val Met Thr
145                 150                 155                 160

Leu Val Thr Val Phe Gly Ala Leu Met Tyr Val Val Glu Gly Pro Glu
                 165                 170                 175

His Gly Phe Thr Ser Ile Pro Arg Gly Ile Tyr Trp Ala Ile Val Thr
             180                 185                 190

Leu Thr Thr Val Gly Phe Gly Asp Ile Thr Pro Lys Thr Pro Leu Gly
         195                 200                 205

Gln Ala Ile Ala Ser Leu Val Met Leu Thr Gly Tyr Ser Ile Ile Ala
     210                 215                 220

Val Pro Thr Gly Ile Phe Thr Ala Glu Leu Ala Thr Ala Met Arg Gln
225                 230                 235                 240

Asp Pro Ala Asn Leu Leu Gln Arg Asp Cys Pro Val Cys Arg Lys Ala
                 245                 250                 255

Thr His Glu Val Gln Ala Ala Phe Cys Cys Arg Cys Gly Asn Pro Leu
             260                 265                 270

Phe Pro Arg Glu Glu Gly Ser His Gly Lys Ser
         275                 280

<210> SEQ ID NO 3
<211> LENGTH: 280
<212> TYPE: PRT
<213> ORGANISM: Deinococcus radiodurans

<400> SEQUENCE: 3

Met Ile Ser Pro Pro Asp Pro Pro His Pro Asp His Arg Pro
1               5                   10                  15

Trp Arg Arg Trp Leu Gly Asn Leu Ile Phe Gly Leu Ser Thr Pro Ala
             20                  25                  30

Ala Arg Ala Tyr Asp Lys Ile Val Ile Val Leu Ile Val Ala Ser Val
         35                  40                  45

Leu Ala Val Thr Leu Glu Ser Val Pro Glu Leu Ser His Ala Val Arg
     50                  55                  60

Ala Arg Leu Arg Gln Thr Glu Trp Val Phe Thr Val Met Phe Thr Ala
65                  70                  75                  80

Asp Tyr Leu Leu Arg Leu Leu Gly Ala Arg Arg Pro Leu Arg Tyr Ala
                 85                  90                  95

Leu Ser Phe Tyr Gly Leu Val Asp Leu Leu Thr Ile Leu Pro Ser Tyr
```

-continued

```
                100                 105                 110
Leu Ser Leu Leu Phe Pro Gly Thr Gln Tyr Leu Leu Val Val Arg Ala
        115                 120                 125

Leu Arg Leu Leu Arg Val Phe Arg Val Phe Lys Leu Ala Arg Tyr Ser
    130                 135                 140

Asp Gln Ala Ala Leu Ile Gly Glu Ala Leu Gln Ala Ser Arg Glu Lys
145                 150                 155                 160

Ile Ile Val Phe Phe Ile Ser Val Leu Ser Met Val Ile Val Phe Gly
                165                 170                 175

Thr Leu Leu Tyr Met Val Glu Gly Pro Glu Ser Gly Phe Thr Ser Ile
            180                 185                 190

Pro Thr Ser Ile Tyr Trp Ala Val Val Thr Val Thr Thr Val Gly Tyr
        195                 200                 205

Gly Asp Ile Ser Pro Lys Thr Gly Leu Gly Lys Phe Ile Ala Thr Leu
    210                 215                 220

Ala Met Leu Ser Gly Tyr Ala Ile Ile Ala Val Pro Thr Gly Ile Val
225                 230                 235                 240

Thr Val Gly Leu Gln Gln Ala Gln Glu Ala Arg Arg Gly Arg Thr Cys
                245                 250                 255

Pro Gln Cys Gly Leu Ser Arg His Asp Ala Asp Ala Arg Phe Cys Lys
            260                 265                 270

Arg Cys Gly Glu Asn Leu Pro Gly
        275                 280

<210> SEQ ID NO 4
<211> LENGTH: 656
<212> TYPE: PRT
<213> ORGANISM: Drosophila melanogaster

<400> SEQUENCE: 4

Met Ala Ala Val Ala Gly Leu Tyr Gly Leu Gly Glu Asp Arg Gln His
1               5                   10                  15

Arg Lys Lys Gln Gln Gln Gln Gln His Gln Lys Glu Gln Leu Glu
            20                  25                  30

Gln Lys Glu Glu Gln Lys Lys Ile Ala Glu Arg Lys Leu Gln Leu Arg
        35                  40                  45

Glu Gln Gln Leu Gln Arg Asn Ser Leu Asp Gly Tyr Gly Ser Leu Pro
    50                  55                  60

Lys Leu Ser Ser Gln Asp Glu Glu Gly Gly Ala Gly His Gly Phe Gly
65                  70                  75                  80

Gly Gly Pro Gln His Phe Glu Pro Ile Pro His Asp His Asp Phe Cys
                85                  90                  95

Glu Arg Val Val Ile Asn Val Ser Gly Leu Arg Phe Glu Thr Gln Leu
            100                 105                 110

Arg Thr Leu Asn Gln Phe Pro Asp Thr Leu Leu Gly Asp Pro Ala Arg
        115                 120                 125

Arg Leu Arg Tyr Phe Asp Pro Leu Arg Asn Glu Tyr Phe Phe Asp Arg
    130                 135                 140

Ser Arg Pro Ser Phe Asp Ala Ile Leu Tyr Tyr Tyr Gln Ser Gly Gly
145                 150                 155                 160

Arg Leu Arg Arg Pro Val Asn Val Pro Leu Asp Val Phe Ser Glu Glu
                165                 170                 175

Ile Lys Phe Tyr Glu Leu Gly Asp Gln Ala Ile Asn Lys Phe Arg Glu
            180                 185                 190
```

```
Asp Glu Gly Phe Ile Lys Glu Glu Arg Pro Leu Pro Asp Asn Glu
        195                 200                 205

Lys Gln Arg Lys Val Trp Leu Leu Phe Glu Tyr Pro Glu Ser Ser Gln
    210                 215                 220

Ala Ala Arg Val Val Ala Ile Ile Ser Val Phe Val Ile Leu Leu Ser
225                 230                 235                 240

Ile Val Ile Phe Cys Leu Glu Thr Leu Pro Glu Phe Lys His Tyr Lys
                245                 250                 255

Val Phe Asn Thr Thr Thr Asn Gly Thr Lys Ile Glu Glu Asp Glu Val
                260                 265                 270

Pro Asp Ile Thr Asp Pro Phe Phe Leu Ile Glu Thr Leu Cys Ile Ile
            275                 280                 285

Trp Phe Thr Phe Glu Leu Thr Val Arg Phe Leu Ala Cys Pro Asn Lys
            290                 295                 300

Leu Asn Phe Cys Arg Asp Val Met Asn Val Ile Asp Ile Ile Ala Ile
305                 310                 315                 320

Ile Pro Tyr Phe Ile Thr Leu Ala Thr Val Val Ala Glu Glu Glu Asp
                325                 330                 335

Thr Leu Asn Leu Pro Lys Ala Pro Val Ser Pro Gln Asp Lys Ser Ser
            340                 345                 350

Asn Gln Ala Met Ser Leu Ala Ile Leu Arg Val Ile Arg Leu Val Arg
            355                 360                 365

Val Phe Arg Ile Phe Lys Leu Ser Arg His Ser Lys Gly Leu Gln Ile
            370                 375                 380

Leu Gly Arg Thr Leu Lys Ala Ser Met Arg Glu Leu Gly Leu Leu Ile
385                 390                 395                 400

Phe Phe Leu Phe Ile Gly Val Val Leu Phe Ser Ser Ala Val Tyr Phe
                405                 410                 415

Ala Glu Ala Gly Ser Glu Asn Ser Phe Phe Lys Ser Ile Pro Asp Ala
            420                 425                 430

Phe Trp Trp Ala Val Val Thr Met Thr Thr Val Gly Tyr Gly Asp Met
        435                 440                 445

Thr Pro Val Gly Val Trp Gly Lys Ile Val Gly Ser Leu Cys Ala Ile
    450                 455                 460

Ala Gly Val Leu Thr Ile Ala Leu Pro Val Pro Val Ile Val Ser Asn
465                 470                 475                 480

Phe Asn Tyr Phe Tyr His Arg Glu Thr Asp Gln Glu Glu Met Gln Ser
                485                 490                 495

Gln Asn Phe Asn His Val Thr Ser Cys Pro Tyr Leu Pro Gly Thr Leu
            500                 505                 510

Gly Gln His Met Lys Lys Ser Ser Leu Ser Glu Ser Ser Ser Asp Met
        515                 520                 525

Met Asp Leu Asp Asp Gly Val Glu Ser Thr Pro Gly Leu Thr Glu Thr
530                 535                 540

His Pro Gly Arg Ser Ala Val Ala Pro Phe Leu Gly Ala Gln Gln Gln
545                 550                 555                 560

Gln Gln Gln Gln Pro Val Ala Ser Ser Leu Ser Met Ser Ile Asp Lys
                565                 570                 575

Gln Leu Gln His Pro Leu Gln His Val Thr Gln Thr Gln Leu Tyr Gln
            580                 585                 590

Gln Gln Gln Gln Gln Gln Gln Gln Gln Asn Gly Phe Lys Gln Gln
            595                 600                 605

Gln Gln Gln Thr Gln Gln Gln Leu Gln Gln Gln Gln Ser His Thr Ile
```

610                 615                 620
Asn Ala Ser Ala Ala Ala Thr Ser Gly Ser Gly Ser Ser Gly Leu
625                 630                 635                 640

Thr Met Arg His Asn Asn Ala Leu Ala Val Ser Ile Glu Thr Asp Val
                    645                 650                 655

<210> SEQ ID NO 5
<211> LENGTH: 857
<212> TYPE: PRT
<213> ORGANISM: Rattus norvegicus

<400> SEQUENCE: 5

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
            20                  25                  30

Val Arg Leu Asn Val Gly Gly Leu Ala His Glu Val Leu Trp Arg Thr
        35                  40                  45

Leu Asp Arg Leu Pro Arg Thr Arg Leu Gly Lys Leu Arg Asp Cys Asn
    50                  55                  60

Thr His Asp Ser Leu Leu Gln Val Cys Asp Asp Tyr Ser Leu Glu Asp
65                  70                  75                  80

Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Glu Met Cys Ala
            100                 105                 110

Leu Ser Phe Ser Gln Glu Leu Asp Tyr Trp Gly Ile Asp Glu Ile Tyr
        115                 120                 125

Leu Glu Ser Cys Cys Gln Ala Arg Tyr His Gln Lys Lys Glu Gln Met
    130                 135                 140

Asn Glu Glu Leu Lys Arg Glu Ala Glu Thr Leu Arg Glu Arg Glu Gly
145                 150                 155                 160

Glu Glu Phe Asp Asn Thr Cys Cys Ala Glu Lys Arg Lys Lys Leu Trp
                165                 170                 175

Asp Leu Leu Glu Lys Pro Asn Ser Ser Val Ala Ala Lys Ile Leu Ala
            180                 185                 190

Ile Ile Ser Ile Met Phe Ile Val Leu Ser Thr Ile Ala Leu Ser Leu
        195                 200                 205

Asn Thr Leu Pro Glu Leu Gln Ser Leu Asp Glu Phe Gly Gln Ser Thr
    210                 215                 220

Asp Asn Pro Gln Leu Ala His Val Glu Ala Val Cys Ile Ala Trp Phe
225                 230                 235                 240

Thr Met Glu Tyr Leu Leu Arg Phe Leu Ser Ser Pro Lys Lys Trp Lys
                245                 250                 255

Phe Phe Lys Gly Pro Leu Asn Ala Ile Asp Leu Leu Ala Ile Leu Pro
            260                 265                 270

Tyr Tyr Val Thr Ile Phe Leu Thr Glu Ser Asn Lys Ser Val Leu Gln
        275                 280                 285

Phe Gln Asn Val Arg Arg Val Val Gln Ile Phe Arg Ile Met Arg Ile
    290                 295                 300

Leu Arg Ile Leu Lys Leu Ala Arg His Ser Thr Gly Leu Gln Ser Leu
305                 310                 315                 320

Gly Phe Thr Leu Arg Arg Ser Tyr Asn Glu Leu Gly Leu Leu Ile Leu
                325                 330                 335

```
Phe Leu Ala Met Gly Ile Met Ile Phe Ser Ser Leu Val Phe Phe Ala
                340                 345                 350

Glu Lys Asp Glu Asp Thr Lys Phe Lys Ser Ile Pro Ala Ser Phe
            355                 360                 365

Trp Trp Ala Thr Ile Thr Met Thr Thr Val Gly Tyr Gly Asp Ile Tyr
        370                 375                 380

Pro Lys Thr Leu Leu Gly Lys Ile Val Gly Gly Leu Cys Cys Ile Ala
385                 390                 395                 400

Gly Val Leu Val Ile Ala Leu Pro Ile Pro Ile Ile Val Asn Asn Phe
                405                 410                 415

Ser Glu Phe Tyr Lys Glu Gln Lys Arg Gln Glu Lys Ala Ile Lys Arg
            420                 425                 430

Arg Glu Ala Leu Glu Arg Ala Lys Arg Asn Gly Ser Ile Val Ser Met
        435                 440                 445

Asn Met Lys Asp Ala Phe Ala Arg Ser Ile Glu Met Met Asp Ile Val
    450                 455                 460

Val Glu Lys Asn Gly Glu Ser Ile Ala Lys Lys Asp Lys Val Gln Asp
465                 470                 475                 480

Asn His Leu Ser Pro Asn Lys Trp Lys Trp Thr Lys Arg Ala Leu Ser
                485                 490                 495

Glu Thr Ser Ser Ser Lys Ser Phe Glu Thr Lys Glu Gln Gly Ser Pro
            500                 505                 510

Glu Lys Ala Arg Ser Ser Ser Pro Gln His Leu Asn Val Gln Gln
        515                 520                 525

Leu Glu Asp Met Tyr Ser Lys Met Ala Lys Thr Gln Ser Gln Pro Ile
    530                 535                 540

Leu Asn Thr Lys Glu Met Ala Pro Gln Ser Lys Pro Pro Glu Glu Leu
545                 550                 555                 560

Glu Met Ser Ser Met Pro Ser Pro Val Ala Pro Leu Pro Ala Arg Thr
                565                 570                 575

Glu Gly Val Ile Asp Met Arg Ser Met Ser Ser Ile Asp Ser Phe Ile
            580                 585                 590

Ser Cys Ala Thr Asp Phe Pro Glu Ala Thr Arg Phe Ser His Ser Pro
        595                 600                 605

Leu Ala Ser Leu Ser Ser Lys Ala Gly Ser Ser Thr Ala Pro Glu Val
    610                 615                 620

Gly Trp Arg Gly Ala Leu Gly Ala Ser Gly Gly Arg Leu Thr Glu Thr
625                 630                 635                 640

Asn Pro Ile Pro Glu Thr Ser Arg Ser Gly Phe Val Glu Ser Pro
                645                 650                 655

Arg Ser Ser Met Lys Thr Asn Asn Pro Leu Lys Leu Arg Ala Leu Lys
            660                 665                 670

Val Asn Phe Val Glu Gly Asp Pro Thr Pro Leu Leu Pro Ser Leu Gly
        675                 680                 685

Leu Tyr His Asp Pro Leu Arg Asn Arg Gly Ala Ala Ala Val
    690                 695                 700

Ala Gly Leu Glu Cys Ala Ser Leu Leu Asp Lys Pro Val Leu Ser Pro
705                 710                 715                 720

Glu Ser Ser Ile Tyr Thr Thr Ala Ser Ala Arg Thr Pro Pro Arg Ser
                725                 730                 735

Pro Glu Lys His Thr Ala Ile Ala Phe Asn Phe Glu Ala Gly Val His
            740                 745                 750

His Tyr Ile Asp Thr Asp Thr Asp Asp Glu Gly Gln Leu Leu Tyr Ser
```

```
                        755                 760                 765
Val Asp Ser Ser Pro Pro Lys Ser Leu His Gly Ser Thr Ser Pro Lys
    770                 775                 780

Phe Ser Thr Gly Ala Arg Thr Glu Lys Asn His Phe Glu Ser Ser Pro
785                 790                 795                 800

Leu Pro Thr Ser Pro Lys Phe Leu Arg Pro Asn Cys Val Tyr Ser Ser
                805                 810                 815

Glu Gly Leu Thr Gly Lys Gly Pro Gly Ala Gln Glu Lys Cys Lys Leu
            820                 825                 830

Glu Asn His Thr Pro Pro Asp Val His Met Leu Pro Gly Gly Gly Ala
        835                 840                 845

His Gly Ser Thr Arg Asp Gln Ser Ile
    850                 855

<210> SEQ ID NO 6
<211> LENGTH: 655
<212> TYPE: PRT
<213> ORGANISM: Homo sapiens

<400> SEQUENCE: 6

Met Ala Ala Gly Val Ala Ala Trp Leu Pro Phe Ala Arg Ala Ala Ala
1               5                   10                  15

Ile Gly Trp Met Pro Val Ala Asn Cys Pro Met Pro Leu Ala Pro Ala
            20                  25                  30

Asp Lys Asn Lys Arg Gln Asp Glu Leu Ile Val Leu Asn Val Ser Gly
        35                  40                  45

Arg Arg Phe Gln Thr Trp Arg Thr Thr Leu Glu Arg Tyr Pro Asp Thr
    50                  55                  60

Leu Leu Gly Ser Thr Glu Lys Glu Phe Phe Phe Asn Glu Asp Thr Lys
65                  70                  75                  80

Glu Tyr Phe Phe Asp Arg Asp Pro Glu Val Phe Arg Cys Val Leu Asn
                85                  90                  95

Phe Tyr Arg Thr Gly Lys Leu His Tyr Pro Arg Tyr Glu Cys Ile Ser
            100                 105                 110

Ala Tyr Asp Asp Glu Leu Ala Phe Tyr Gly Ile Leu Pro Glu Ile Ile
        115                 120                 125

Gly Asp Cys Cys Tyr Glu Glu Tyr Lys Asp Arg Lys Arg Glu Asn Ala
    130                 135                 140

Glu Arg Leu Met Asp Asp Asn Asp Ser Glu Asn Asn Gln Glu Ser Met
145                 150                 155                 160

Pro Ser Leu Ser Phe Arg Gln Thr Met Trp Arg Ala Phe Glu Asn Pro
                165                 170                 175

His Thr Ser Thr Leu Ala Leu Val Phe Tyr Tyr Val Thr Gly Phe Phe
            180                 185                 190

Ile Ala Val Ser Val Ile Thr Asn Val Val Glu Thr Val Pro Cys Gly
        195                 200                 205

Thr Val Pro Gly Ser Lys Glu Leu Pro Cys Gly Glu Arg Tyr Ser Val
    210                 215                 220

Ala Phe Phe Cys Leu Asp Thr Ala Cys Val Met Ile Phe Thr Gly Glu
225                 230                 235                 240

Tyr Leu Leu Arg Leu Phe Ala Ala Pro Ser Arg Tyr Arg Phe Ile Arg
                245                 250                 255

Ser Val Met Ser Ile Ile Asp Val Val Ala Ile Met Pro Tyr Tyr Ile
            260                 265                 270
```

Gly Leu Val Met Thr Asn Asn Glu Asp Val Ser Gly Ala Phe Val Thr
                275                 280                 285

Leu Arg Val Phe Arg Val Phe Arg Ile Phe Lys Phe Ser Arg His Ser
            290                 295                 300

Gln Gly Leu Arg Ile Leu Gly Tyr Thr Leu Lys Ser Cys Ala Ser Glu
305                 310                 315                 320

Leu Gly Phe Leu Leu Phe Ser Leu Thr Met Ala Ile Ile Ile Phe Ala
                325                 330                 335

Thr Val Met Phe Tyr Ala Glu Lys Gly Ser Ser Ala Ser Lys Phe Thr
                340                 345                 350

Ser Ile Pro Ala Ser Phe Trp Tyr Thr Ile Val Thr Met Thr Thr Leu
                355                 360                 365

Gly Tyr Gly Asp Met Val Leu Lys Thr Ile Ala Gly Lys Ile Phe Gly
        370                 375                 380

Ser Ile Cys Ser Leu Ser Gly Val Leu Val Ile Ala Leu Pro Val Pro
385                 390                 395                 400

Val Ile Val Ser Asn Phe Ser Arg Ile Tyr His Gln Asn Gln Arg Ala
                405                 410                 415

Asp Lys Arg Arg Ala Gln Lys Lys Ala Arg Leu Ala Arg Ile Arg Val
            420                 425                 430

Ala Lys Thr Gly Ser Ser Asn Ala Tyr Leu His Ser Lys Arg Asn Gly
                435                 440                 445

Leu Leu Asn Glu Ala Leu Glu Leu Thr Gly Thr Pro Glu Glu Glu His
            450                 455                 460

Met Gly Lys Thr Thr Ser Leu Ile Glu Ser Gln His His His Leu Leu
465                 470                 475                 480

His Cys Leu Glu Lys Thr Thr Gly Leu Ser Tyr Leu Val Asp Asp Pro
                485                 490                 495

Leu Leu Ser Val Arg Thr Ser Thr Ile Lys Asn His Glu Phe Ile Asp
                500                 505                 510

Glu Gln Met Phe Glu Gln Asn Cys Met Glu Ser Ser Met Gln Asn Tyr
            515                 520                 525

Pro Ser Thr Arg Ser Pro Ser Leu Ser Ser His Pro Gly Leu Thr Thr
            530                 535                 540

Thr Cys Cys Ser Arg Arg Ser Lys Lys Thr Thr His Leu Pro Asn Ser
545                 550                 555                 560

Asn Leu Pro Ala Thr Arg Leu Arg Ser Met Gln Glu Leu Ser Thr Ile
                565                 570                 575

His Ile Gln Gly Ser Glu Gln Pro Ser Leu Thr Thr Ser Arg Ser Ser
            580                 585                 590

Leu Asn Leu Lys Ala Asp Asp Gly Leu Arg Pro Asn Cys Lys Thr Ser
            595                 600                 605

Gln Ile Thr Thr Ala Ile Ile Ser Ile Pro Thr Pro Pro Ala Leu Thr
            610                 615                 620

Pro Glu Gly Glu Ser Arg Pro Pro Ala Ser Pro Gly Pro Asn Thr
625                 630                 635                 640

Asn Ile Pro Ser Ile Thr Ser Asn Val Val Lys Val Ser Val Leu
                645                 650                 655

<210> SEQ ID NO 7
<211> LENGTH: 6942
<212> TYPE: DNA
<213> ORGANISM: Rattus norvegicus

<400> SEQUENCE: 7

```
tctagagccc cccacatgct cccccaccgg gtcccccgtt gcgtgaggac acctcctctg    60 agggctccg ctcgcccctc ttcggacccc ccggggcccc ggctggccag aggatggacg   120
aggaggagga tggagcgggc gccgaggagt cggacagcc ccgtagcttc acgcagctca   180
acgacctgtc cggggccggg ggccggcagg ggccggggtc gacggaaaag gacccgggca   240
gcgcggactc cgaggcggag gggctgccgt accccggcgct agccccggtg gttttcttct   300
acttgagcca ggacagccgc ccgcggagct ggtgtctccg cacggtctgt aacccgtggt   360
tcgagcgagt cagtatgctg gtcattcttc tcaactgtgt gactctgggt atgttcaggc   420
cgtgtgagga cattgcctgt gactcccagc gctgccggat cctgcaggcc ttcgatgact   480
tcatctttgc cttctttgct gtggaaatgg tggtgaagat ggtggccttg gcatctttg   540 ggaagaaatg ttacctggga gacacttgga accggcttga cttttttcatt gtcattgcag   600 ggatgctgga gtattcgctg gacctgcaga acgtcagctt ctccgcagtc aggacagtcc   660
gtgtgctgcg accgctcagg gccattaacc gggtgcccag catgcgcatt ctcgtcacat   720
tactgctgga caccttgcct atgctgggca acgtcctgct gctctgtttc ttcgtctttt   780
tcatctttgg catcgtgggc gtccagctgt gggcaggact gcttcgcaac cggtgcttcc   840
tccccgagaa cttcagcctc cccctgagcg tggacctgga gccttattac agacagagaa   900
atgaggacga gagcccttc atctgctctc agcctcggga gaatggcatg agatcctgca   960
ggagtgtgcc cacactgcgt ggggaaggcg gtggtggccc accctgcagt ctggactatg  1020
agacctataa cagttccagc aacaccacct gtgtcaactg gaaccagtac tataccaact  1080
gctctgcggg cgagcacaac cccttcaaag gcgccatcaa ctttgacaac attggctatg  1140
cctggatcgc catcttccag gtcatcacac tggaggctg gtcgacatc atgtacttcg  1200 taatggacgc tcactccttc tacaacttca tctacttcat tcttctcatc atcgtgggct  1260
ccttcttcat gatcaacctg tgcctggtgg tgattgccac gcagttctcc gagaccaaac  1320
agcgggagag tcagctgatg cgggagcagc gtgtacgatt cctgtccaat gctagcaccc  1380
tggcaagctt ctctgagcca ggcagctgct atgaggagct actcaagtac ctggtgtaca  1440
tcctccgaaa agcagcccga aggctggccc aggtctctag ggctataggc gtgcgggctg  1500
ggctgctcag cagcccagtg gccgtagtg gcaggagcc ccagcccagt ggcagctgca  1560
ctcgctcaca ccgtcgtctg tctgtccacc acctggtcca ccaccatcac caccaccatc  1620
accactacca cctgggtaat gggacgctca gagttcccg ggccagccca gagatccagg  1680
acagggatgc caatgggtct cgccggctca tgctaccacc accctctaca cccactccct  1740
ctgggggccc tccgaggggt gcggagtctg tacacagctt ctaccatgct gactgccact  1800
tggagccagt ccgttgccag gcaccccctc ccagatgccc atcggaggca tctggtagga  1860
ctgtgggtag tgggaaggtg taccccactg tgcataccag ccctccacca gagatactga  1920
aggataaagc actagtggag gtggcccca gccctgggcc cccaccctc accagcttca  1980 acatcccacc tgggcccttc agctccatgc acaagctcct ggagacacag agtacgggag  2040
cctgccatag ctcctgcaaa atctccagcc cttgctccaa ggcagacagt ggagcctgcg  2100
ggccggacag ttgtccctac tgtgcccgga caggagcagg agagcagag tccgctgacc  2160 atgtcatgcc tgactcagac agcgaggctg tgtatgagtt cacacaggac gctcagcaca  2220
gtgacctccg ggatcccac agccggcggc gacagcggag cctgggccca gatgcagagc  2280
ctagttctgt gctggctttc tggaggctga tctgtgacac attccggaag atcgtagata  2340
```

-continued

```
gcaaatactt tggccgggga atcatgatcg ccatcctggt caatacactc agcatgggca    2400
tcgagtacca cgagcagccc gaggagctca ccaacgccct ggaaatcagc aacatcgtct    2460
tcaccagcct cttcgccttg gagatgctgc tgaaactgct tgtctacggt ccctttggct    2520
acattaagaa tccctacaac atctttgatg gtgtcattgt ggtcatcagt gtgtgggaga    2580
ttgtgggcca gcagggaggt ggcctgtcgg tgctgcggac cttccgcctg atgcgggtgc    2640
tgaagctggt gcgcttcctg ccggcccgtgc agcgccagct cgtggtgctc atgaagacca    2700
tggacaacgt ggccaccttc tgcatgctcc tcatgctgtt catcttcatc ttcagcatcc    2760
tgggcatgca tctcttttggt tgcaagttcg catctgaacg ggatggggac acgttgccag    2820
accggaagaa tttcgactcc ctgctctggg ccatcgtcac tgtctttcag attctgactc    2880
aggaagactg aataaagtc ctctacaacg gcatggcctc cacatcgtct tgggctgctc    2940
tttacttcat cgccctcatg acttttggca actatgtgct ctttaacctg ctggtggcca    3000
ttcttgtgga aggattccag gcagaggag atgccaccaa gtctgagtca gagcctgatt    3060
tcttttcgcc cagtgtggat ggtgatgggg acagaaagaa gcgcttggcc ctggtggctt    3120
tgggagaaca cgcggaacta cgaaagagcc ttttgccacc cctcatcatc catacggctg    3180
cgacaccaat gtcacacccc aagagctcca gcacaggtgt gggggaagca ctgggctctg    3240
gctctcgacg taccagtagc agtgggtccg ctgagcctgg agctgcccac catgagatga    3300
aatgtccgcc aagtgcccgc agctccccgc acagtccctg gagtgcggca agcagctgga    3360
ccagcaggcg ctccagcagg aacagcctgg gccgggcccc cagcctaaag cggaggagcc    3420
cgagcgggga gcggaggtcc ctgctgtctg gagagggcca ggagagtcag gatgaggagg    3480
aaagttcaga gaggaccgg gccagcccag caggcagtga ccatcgccac aggggttcct    3540
tggaacgtga ggccaagagt tcctttgacc tgcctgacac tctgcaggtg ccggggctgc    3600
accgcacagc cagcggccgg agctctgcct ctgagcacca agactgtaat ggcaagtcgg    3660
cttcagggcg tttggcccgc accctgagga ctgatgaccc ccaactggat ggggatgatg    3720
acaatgatga gggaaatctg agcaaagggg aacgcataca agcctgggtc agatcccggc    3780
ttcctgcctg ttgccgagag cgagattcct ggtcggccta tatctttcct cctcagtcaa    3840
ggtttcgtct cctgtgtcac cggatcatca cccacaagat gtttgaccat gtggtcctcg    3900
tcatcatctt cctcaactgt atcaccatcg ctatggagcg ccccaaaatt gaccccaca    3960 gcgctgagcg catcttcctg accctctcca actacatctt cacggcagtc tttctagctg    4020
aaatgacagt gaaggtggtg gcactgggct ggtgctttgg ggagcaggcc tacctgcgca    4080
gcagctggaa tgtgctggac ggcttgctgg tgctcatctc cgtcatcgac atcctggtct    4140
ccatggtctc cgacagcggc accaagatcc ttggcatgct gagggtgctg cggctgctgc    4200
ggaccctgcg tccactcagg gtcatcagcc gggcccaggg actgaagctg tggtagaga    4260 ctctgatgtc atccctcaaa cccattgcaa acattgtggt catttgctgt gccttcttca    4320 tcattttttgg aattctcggg gtgcagctct tcaaagggaa gttcttcgtg tgtcagggtg    4380
aggacaccag gaacatcact aacaaatccg actgcgctga ggccagctac cgatgggtcc    4440
ggcacaagta caactttgac aacctgggcc aggtctgat gtccctgttt gtgctggcct    4500
ccaaggatgt tgggttgac atcatgtatg atgggctgga tgctgtgggt gtggatcagc    4560
agcccatcat gaaccacaac ccctggatgc tgctatactt catctccttc ctcctcatcg    4620
tggccttctt tgtcctgaac atgtttgtgg gcgtggtggt ggagaacttc cataagtgca    4680
gacagcacca ggaggaggag gaggcgaggc ggcgtgagga gaagcgacta cggaggctgg    4740
```

```
agaaaaagag aaggagtaag gagaagcaga tggccgaagc ccagtgcaag ccctactact   4800
ctgactactc gagattccgg ctccttgtcc accacctgtg taccagccac tacctggacc   4860
tcttcatcac tggtgtcatc gggctgaacg tggtcactat ggccatgaa cattaccagc   4920 agccccagat cctggacgag gctctgaaga tctgcaatta catctttacc gtcatctttg   4980
tctttgagtc agttttcaaa cttgtggcct ttggcttccg ccgtttcttc caggacaggt   5040
ggaaccagct ggacctggct attgtgcttc tgtccatcat gggcatcaca ctggaggaga   5100
ttgaggtcaa tctgtcgctg cccatcaacc ccaccatcat ccgtatcatg agggtgctcc   5160
gcattgctcg agttctgaag ctgttgaaga tggctgtggg catgcgggca ctgctgcaca   5220
cggtgatgca ggccctgccc caggtgggga acctgggact tctcttcatg ttattgtttt   5280
tcatctttgc agctctgggc gtggagctct ttggagacct ggagtgtgat gagacacacc   5340
cttgtgaggg cttgggtcgg catgccacct ttaggaactt tggtatggcc tttctgaccc   5400
tcttccgagt ctccactggt gacaactgga atggtattat gaaggacacc ctccgggact   5460
gtgaccagga gtccacctgc tacaacactg tcatctcccc tatctacttt gtgtccttcg   5520
tgctgacggc ccagtttgtg ctggtcaacg tggtcatagc tgtgctgatg aagcacctgg   5580
aagaaagcaa caaagaggcc aaggaggagg ccgagctcga ggccgagctg agctggaga   5640 tgaagacgct cagcccgcag ccccactccc cgctgggcag ccccttcctc tggcccgggg   5700
tggagggtgt caacagtact gacagcccta agcctgggc tccacacacc actgcccaca   5760
ttggagcagc ctcgggcttc tcccttgagc accccacgat ggtaccccac cccgaggagg   5820
tgccagtccc cctaggacca gacctgctga ctgtgaggaa gtctggtgtc agccggacgc   5880
actctctgcc caatgacagc tacatgtgcc gcaatgggag cactgctgag agatccctag   5940
gacacagggg ctggggctc cccaaagccc agtcaggctc catcttgtcc gttcactccc   6000
aaccagcaga caccagctgc atcctacagc ttcccaaaga tgtgcactat ctgctccagc   6060
ctcatggggc tcccacctgg ggcgccatcc ctaaactacc ccacctggc cgctccctc   6120 tggctcagag gcctctcagg cgccaggcag caataaggac tgactccctg gatgtgcagg   6180
gcctgggtag ccgggaagac ctgttgtcag aggtgagtgg gccctcctgc cctctgaccc   6240
ggtcctcatc cttctgggc gggtcgagca tccaggtgca gcagcgttcc ggcatccaga   6300
gcaaagtctc caagcacatc cgcctgccag ccccttgccc aggcctggaa cccagctggg   6360
ccaaggaccc tccagagacc agaagcagct tagagctgga cacggagctg agctggattt   6420
caggagacct ccttcccagc agccaggaag aaccccgtt cccacgggac ctgaagaagt   6480
gctacagtgt agagacccag agctgcaggc gcaggcctgg gttctggcta gatgaacagc   6540
ggagacactc cattgctgtc agctgtctgg acagcggctc ccaaccccgc ctatgtccaa   6600 gccctcaag cctcggggc caacctcttg ggggtcctgg gagccggcct aagaaaaaac   6660
tcagcccacc cagtatctct atagaccccc cggagagcca gggctctcgg ccccatgca   6720 gtcctggtgt ctgcctcagg aggagggcgc cggccagtga ctctaaggat ccctcggtct   6780 ccagcccct tgacagcacg gctgcctcac cctccccaaa gaaagacacg ctgagtctct   6840
ctggtttgtc ttctgaccca acagacatgg accctgagt cctacccact ctcccccatc   6900 accttttctcc accgggtgca gatcctacgt ccgcctcctg gg                    6942
```

<210> SEQ ID NO 8
<211> LENGTH: 6990
<212> TYPE: DNA

<213> ORGANISM: Homo sapiens

<400> SEQUENCE: 8

| | | | | | |
|---|---|---|---|---|---|
| atggctgaga | gcgcctcccc | gccctcctca | tctgcagcag | ccccagccgc | tgagccagga | 60 |
| gtcaccacgg | agcagcccgg | accccggagc | cccccatcct | ccccgccagg | cctggaggag | 120 |
| cctctggatg | gagctgatcc | tcatgtccca | cacccagacc | tggcgcctat | tgccttcttc | 180 |
| tgcctgcgac | agaccaccag | cccccggaac | tggtgcatca | agatggtgtg | caacccgtgg | 240 |
| tttgaatgtg | tcagcatgct | ggtgatcctg | ctgaactgcg | tgacacttgg | catgtaccag | 300 |
| ccgtgcgacg | acatggactg | cctgtccgac | cgctgcaaga | tcctgcaggt | ctttgatgac | 360 |
| ttcatcttta | tcttctttgc | catggagatg | gtgctcaaga | tggtggccct | ggggattttt | 420 |
| ggcaagaagt | gctacctcgg | ggacacatgg | aaccgcctgg | atttcttcat | cgtcatggca | 480 |
| gggatggtcg | agtactccct | ggaccttcag | aacatcaacc | tgtcagccat | ccgcaccgtg | 540 |
| cgcgtcctga | ggcccctcaa | agccatcaac | cgcgtgccca | gtatgcggat | cctggtgaac | 600 |
| ctgctcctgg | acacactgcc | catgctgggg | aatgtcctgc | tgctctgctt | ctttgtcttc | 660 |
| ttcatctttg | catcatagg | tgtgcagctc | tgggcgggcc | tgctgcgtaa | ccgctgcttc | 720 |
| ctggaggaga | acttcaccat | acaaggggat | gtggccttgc | ccccatacta | ccagccggag | 780 |
| gaggatgatg | agatgccctt | catctgctcc | ctgtcgggcg | acaatgggat | aatgggctgc | 840 |
| catgagatcc | ccccgctcaa | ggagcagggc | cgtgagtgct | gcctgtccaa | ggacgacgtc | 900 |
| tacgactttg | ggcgggggcg | ccaggacctc | aatgccagcg | gcctctgtgt | caactggaac | 960 |
| cgttactaca | atgtgtgccg | cacgggcagc | gccaaccccc | acaagggtgc | catcaacttt | 1020 |
| gacaacatcg | ttatgcttg | gattgtcatc | ttccaggtga | tcactctgga | aggctgggtg | 1080 |
| gagatcatgt | actacgtgat | ggatgctcac | tccttctaca | acttcatcta | cttcatcctg | 1140 |
| cttatcatag | tgggctcctt | cttcatgatc | aacctgtgcc | tcgttgtcat | agcgacccag | 1200 |
| ttctcggaga | ccaagcaacg | ggagcaccgg | ctgatgctgg | agcagcggca | gcgctacctg | 1260 |
| tcctccagca | cggtggccag | ctacgccgag | cctggcgact | gctacgagga | gatcttccag | 1320 |
| tatgtctgcc | acatcctgcg | caaggccaag | cgccgcgccc | tgggcctcta | ccaggccctg | 1380 |
| cagagccggc | gccaggccct | gggccccgag | gccccggccc | ccgccaaacc | tgggccccac | 1440 |
| gccaaggagc | cccggcacta | ccatgggaag | actaagggtc | agggagatga | agggagacat | 1500 |
| ctcggaagcc | ggcattgcca | gactttgcat | gggcctgcct | ccctggaaa | tgatcactcg | 1560 |
| ggaagagagc | tgtgcccgca | acatagcccc | ctggatgcga | cgcccacac | cctggtgcag | 1620 |
| cccatccccg | ccacgctggc | ttccgatccc | gccagctgcc | cttgctgcca | gcatgaggac | 1680 |
| ggccggcggc | cctcggcct | gggcagcacc | gactcgggcc | aggagggctc | gggctccggg | 1740 |
| agctccgctg | gtggcgagga | cgaggcggat | ggggacgggg | cccggagcag | cgaggacgga | 1800 |
| gcctcctcag | aactggggaa | ggaggaggag | gaggaggagc | aggcggatgg | ggcggtctgg | 1860 |
| ctgtgcgggg | atgtgtggcg | ggagacgcga | gccaagctgc | gcggcatcgt | ggacagcaag | 1920 |
| tacttcaacc | ggggcatcat | gatggccatc | ctggtcaaca | ccgtcagcat | gggcatcgag | 1980 |
| caccacgagc | agccggagga | gctgaccaac | atcctggaga | tctgcaatgt | ggtcttcacc | 2040 |
| agcatgtttg | ccctggagat | gatcctgaag | ctggctgcat | ttgggctctt | cgactacctg | 2100 |
| cgtaaccccc | taacatctct | cgacagcatc | attgtcatca | tcagcatctg | ggagatcgtg | 2160 |
| gggcaggcgg | acggtgggct | gtcggtgctg | cggaccttcc | ggctgctgcg | cgtgctgaaa | 2220 |
| ctggtgcgct | tcatgcctgc | cctgcggcgc | cagctcgtgg | tgctcatgaa | gaccatggac | 2280 |

```
aacgtggcca ccttctgcat gctgctcatg ctcttcatct tcatcttcag catccttggg    2340
atgcatattt ttggctgcaa gttcagcctc cgcacggaca ctggagacac ggtgcccgac    2400
aggaagaact tcgactccct gctgtgggcc atcgtcactg tgttccagat cctcacccag    2460
gaggactgga acgtcgttct ctacaatggc atggcctcca cttctccctg gcctccctc    2520 tactttgtcg ccctcatgac cttcggcaac tatgtgctct tcaacctgct ggtgccatc    2580 ctggtggagg gcttccaggc ggagggtgac gccaatcgct cctactcgga cgaggaccag    2640
agctcatcca acatagaaga gtttgataag ctccaggaag gcctggacag cagcggagat    2700
cccaagctct gcccaatccc catgaccccc aatgggcacc tggacccag tctcccactg    2760 ggtgggcacc taggtcctgc tggggctgcg ggacctgccc ccgactctc actgcagccg    2820 gaccccatgc tggtggccct gggctcccga aagagcagtg tcatgtctct agggaggatg    2880
agctatgacc agcgctccct gtccagctcc cggagctcct actacgggcc atggggccgc    2940
agcgcggcct gggccagccg tcgctccagc tggaacagcc tcaagcacaa gccgccgtcg    3000
gcggagcatg agtccctgct ctctgcggag cgcggcggcg gcgcccgggt ctgcgaggtt    3060
gccgcggacg aggggccgcc gcgggccgca cccctgcaca ccccacacgc ccaccacatt    3120
catcacgggc cccatctggc gcaccgccac cgccaccacc gccggacgct gtccctcgac    3180
aacagggact cggtggacct ggccgagctg gtgcccgcgg tgggcgccca ccccgggcc    3240 gcctggaggg cggcaggccc ggccccgggg catgaggact gcaatggcag gatgcccagc    3300
atcgccaaag acgtcttcac caagatgggc gaccgcgggg atcgcgggga ggatgaggag    3360
gaaatcgact acaccctgtg cttccgcgtc cgcaagatga tcgacgtcta taagcccgac    3420
tggtgcgagg tccgcgaaga ctggtctgtc tacctcttct ctcccgagaa caggttccgg    3480
gtcctgtgtc agaccattat tgcccacaaa ctcttcgact acgtcgtcct ggccttcatc    3540
tttctcaact gcatcaccat cgccctggag cggcctcaga tcgaggccgg cagcaccgaa    3600
cgcatctttc tcaccgtgtc caactacatc ttcacggcca tcttcgtggg cgagatgaca    3660
ttgaaggtag tctcgctggg cctgtacttc ggcgagcagg cgtacctacg cagcagctgg    3720
aacgtgctgg atggctttct tgtcttcgtg tccatcatcg acatcgtggt gtccctggcc    3780
tcagccgggg gagccaagat cttgggggtc ctccgagtct tgcggctcct gcgcacccta    3840 cgcccccctgc gtgtcatcag ccgggcgccg ggcctgaagc tggtggtgga cacactcatc    3900
tcctccctca gcccatcgg caacatcgtg ctcatctgct gtgccttctt catcatcttt    3960
ggcatcctgg gagtgcagct cttcaagggc aagttctacc actgtctggg cgtggacacc    4020
cgcaacatca ccaaccgctc ggactgcatg gccgccaact accgctgggt ccatcacaaa    4080
tacaacttcg acaacctggg ccaggctctg atgtccctct ttgtcctggc atccaaggat    4140
ggttgggtga acatcatgta caatggactg gatgctgttg ctgtggacca gcagcctgtg    4200
accaaccaca cccctggat gctgctgtac ttcatctcct tcctgctcat cgtcagcttc    4260
tttgtgctca acatgtttgt gggtgtcgtg gtggagaact tccacaagtg ccggcagcac    4320
caggaggctg aagaggcacg gcggcgtgag gagaagcggc tgcggcgcct ggagaagaag    4380
cgccggaagg cccagcggct gccctactat gccacctatt gtcacacccg gctgctcatc    4440
cactccatgt gcaccagcca ctacctggac atcttcatca ccttcatcat ctgcctcaac    4500
gtggtcacca tgtccctgga gcactacaat cagcccacgt ccctggagac agccctcaag    4560
tactgcaact atatgttcac cactgtcttt gtgctggagg ctgtgctgaa gctggtggca    4620
```

```
tttggtctga ggcgcttctt caaggaccga tggaaccagc tggacctggc cattgtgcta    4680
ctgtcagtca tgggcatcac cctggaggag atcgagatca atgcgccct gcccatcaat    4740 cccaccatca tccgcatcat gagggttctg cgcattgccc gagtgctgaa gctgttgaag    4800
atggccacag gaatgcgggc cctgctggac acggtggtgc aagctttgcc ccaggtgggc    4860
aacctgggcc tcctcttcat gctgctcttc ttcatctatg ctgctctcgg ggtggagctc    4920
tttgggaagc tggtctgcaa cgacgagaac ccgtgcgagg gcatgagccg gcatgccacc    4980
ttcgagaact tcggcatggc cttcctcaca ctcttccagg tctccacggg tgacaactgg    5040
aacgggatca tgaaggacac gctgcgggac tgcacccacg acgagcgcag ctgcctgagc    5100
agcctgcagt ttgtgtcgcc gctgtacttc gtgagcttcg tgctcaccgc gcagttcgtg    5160
ctcatcaacg tggtggtggc tgtgctcatg aagcacctgg acgacagcaa caaggaggcg    5220
caggaggacg ccgagatgga tgccgagctc gagctggaga tggcccatgg cctgggccct    5280
ggcccgaggc tgcctaccgg ctccccgggc gcccctggcc gagggccggg aggggcgggc    5340
ggcgggggcg acaccgaggg cggcttgtgc cggcgctgct actcgcctgc ccaggagaac    5400
ctgtggctgg acagcgtctc tttaatcatc aaggactcct tggagggga gctgaccatc    5460 atcgacaacc tgtcgggctc catcttccac cactactcct cgcctgccgg ctgcaagaag    5520
tgtcaccacg acaagcaaga ggtgcagctg gctgagacgg aggccttctc cctgaactca    5580
gacaggtcct cgtccatcct gctgggtgac gacctgagtc tcgaggaccc cacagcctgc    5640
ccacctggcc gcaaagacag caagggtgag ctggacccac ctgagcccat gcgtgtggga    5700
gacctgggcg aatgcttctt ccccttgtcc tctacggccg tctcgccgga tccagagaac    5760
ttcctgtgtg agatggagga gatcccattc aaccctgtcc ggtcctggct gaaacatgac    5820
agcagtcaag cacccccaag tcccttctcc ccggatgcct ccagccctct cctgcccatg    5880
ccagccgagt tcttccaccc tgcagtgtct gccagccaga aaggcccaga aaagggcact    5940
ggcactggaa ccctccccaa gattgcgctg cagggctcct gggcatctct gcggtcacca    6000
agggtcaact gtaccctcct ccggcaggcc accgggagcg acgtcgct ggacgccagc    6060 cccagcagct ccgcgggcag cctgcagacc acgctcgagg acagcctgac cctgagcgac    6120 agccccggc gtgccctggg gccgcccgcg cctgctccag gaccccgggc cggcctgtcc    6180
cccgccgctc gccgccgcct gagcctgcgc ggccggggcc tcttcagcct gcgggggctg    6240
cgggcgcatc agcgcagcca cagcagcggg ggctccacca gcccgggctg cacccaccac    6300
gactccatgg acccctcgga cgaggagggc gcggtggcg cggcggcgg gggcgcgggc    6360 agcgagcact cggagaccct cagcagcctc tcgctcacct ccctcttctg cccgccgccc    6420
ccgccgccag ccccggcct cacgcccgcc aggaagttca gcagcaccag cagcctggcc    6480
gcccccggcc gccccacgc gccgccctg gccacggcc tggcccggag ccctcgtgg    6540 gccgcggacc gcagcaagga ccccccggc cgggcaccgc tgcccatggg cctgggccc    6600 ttggcgcccc cgccgcaacc gctccccgga gagctggagc cgggagacgc cgccagcaag    6660
aggaagagat gagggtcgca ggggccccg gccgcccacc gccgccccg tctcaccttc    6720 tttacctcag gagccaggag cagacagcaa tacttcgtcc acacctggga tcgcgcaggg    6780
cccgcagggc acaggcgccc gacagccggg ctgagcggaa tctgggttag ccaggcctgc    6840
gtggcccatg gtggcccttc cagtgcatat acatacatat atatatatat atgcatatat    6900
atatatatat atatatatat gtgtatacac acacacatag acagacatat atatatatat    6960
ttattttttt tactgagagc ttatgacttc                                     6990
```

<210> SEQ ID NO 9
<211> LENGTH: 9014
<212> TYPE: DNA
<213> ORGANISM: Mus musculus

<400> SEQUENCE: 9

| | | | | | |
|---|---|---|---|---|---|
| gtgtgttgca | catgtctgtg | tgagtacagg | cacacatgtg | catgcaagtg | gttgcagaag | 60 |
| gcagaagatc | actttggatc | ccttggggct | ggagttatag | gtgcttgtga | gccaccagac | 120 |
| atggtacttg | taattgagaa | gcaagtggtc | ccaaccacag | tgccatctct | ccagctccca | 180 |
| ctttctttct | ttttgaccac | aactctcccc | tttataaaag | aggaagaaag | ttattcccaa | 240 |
| gccggggaaa | cactcacaac | aggctccttc | ttttaactta | gtggagaagt | cggggcagcc | 300 |
| tcaaaaacag | tgagtaggtc | acaactctag | tactctacta | agcacttgag | caaattacaa | 360 |
| gatagcaatt | ggtatgcagg | agccaaagta | tgatgagggt | tggatgagca | tgtgctaagc | 420 |
| acagccatcc | tcttttgtct | taattggagc | agatatactg | caagcctctc | tctgtctaga | 480 |
| gataacgttt | attttatttg | gatgcatgag | tattttgctt | acatgtatgt | atgggtacta | 540 |
| tgtgtgtgcc | tggagcctgc | agtggtcacg | agaggggatc | agatcccatg | gaacggagct | 600 |
| cggcgcggcg | cggcccggag | cggcggcggc | agtggcggcg | gcggcgacgc | ttccgcgggg | 660 |
| ctcgccctca | ggtgttcgcg | gctgccgtcg | ccgaagatcg | cgggtcgggg | cctcgcggcg | 720 |
| atcgccctgg | gcgggccgga | gacgcctcgg | gcccccctggc | ggctcggggt | ccacccggcg | 780 |
| ccgcgggccc | gccgctttcc | ctcgcctcgc | ctttgcgcct | cttctcgctc | tgcctctcca | 840 |
| tttattattc | ttatcatttt | tattttcaaa | tggtgtagcc | gccagaggtg | cggtgctaaa | 900 |
| ttcttggaag | gggcccggat | gtactgagga | tgcattacaa | tctcacgaaa | ggaggcggta | 960 |
| gtggaaagca | gcagttttg | gtgtttggtg | caataatggg | gatcaggtaa | tcacccgaag | 1020 |
| ggagcaagaa | ccactgcgga | tccacggctt | cctggatttg | cgcgagagcc | gccggcctcg | 1080 |
| gaggagggat | ccatcccgag | ccgctcgcgg | ctgttgctgc | atttcttcct | ctttgtggct | 1140 |
| tctccttttcc | aagcagtttt | tggccaatgg | tcaatgaaaa | cacgaggatg | tacgttccag | 1200 |
| aggaaaacca | ccaaggttcc | aactatggga | gcccacgccc | agctcatgcc | aacatgaatg | 1260 |
| ccaatgcagc | tgcaggactt | gctcccgagc | acatccctac | tccaggggca | gcactgtcct | 1320 |
| ggcaggcagc | catcgatgcc | gcccggcagg | ccaagctcat | gggcagtgct | ggcaacgcaa | 1380 |
| ccatctctac | cgtcagttcc | acacagcgga | agcggcagca | gtatgggaaa | cccaagaagc | 1440 |
| agggggggcac | aaccgccaca | cggccgcccc | gggctctgct | gtgtctgacc | ctgaagaacc | 1500 |
| ctatccggag | ggcgtgcata | agcattgttg | aatggaaacc | atttgaaatc | attattttac | 1560 |
| tgactatttt | tgccaattgt | gtggccttag | caatctatat | tccctttccg | gaagacgact | 1620 |
| ccaacgccac | caactccaac | ctggaacgag | tggagtatct | cttcctcatc | attttaccg | 1680 |
| tggaagcatt | tttaaaagta | attgcctacg | gacttctctt | ccacccccaac | gcttacctcc | 1740 |
| gcaatggttg | gaatttactg | gatttttataa | tcgtggttgt | agggcttttt | agtgcaattt | 1800 |
| tagaacaagc | aaccaaagct | gatggggcca | atgctctagg | agggaaagga | gctggattcg | 1860 |
| acgtgaaggc | actgagagcg | ttccgcgtgc | tccgtccact | gcggctagtg | tccggagtcc | 1920 |
| caagtctcca | ggtggtcctg | aactccatca | tcaaggccat | ggtgcctctg | ctgcacattg | 1980 |
| cccttcttgt | gctcttcgtc | atcatcattt | atgctattat | cggcctggag | ctcttcatgg | 2040 |
| gaaagatgca | caagacctgc | tacaaccagg | agggcataat | agatgttccg | gcagaagagg | 2100 |

```
atccttcccc ttgtgctttg gagacaggcc atgggcgaca gtgtcagaac gggaccgtgt    2160
gcaaacccgg gtgggatggg cccaagcacg gcatcaccaa cttcgacaac ttcgccttcg    2220
ccatgctgac ggtgttccag tgtatcacca tggagggctg gacagacgtg ctgtactgga    2280
tgcaagacgc tatgggctat gagttgccct gggtgtattt tgtcagtctg gtcatctttg    2340
gatcctttt cgttctaaat ctggttctcg gtgttttgag cggggagttt tccaaagaga    2400
gggagaaagc caaagcccga ggagatttcc agaagcttcg agagaagcag caactagaag    2460
aagatctcaa aggctacctg gactggatca cccaggcaga agacattgac cccgagaatg    2520
aggacgaggg catggatgaa gacaagcctc gaaacatgag catgcccaca agtgagactg    2580
agtctgtcaa cactgaaaac gtggctggag gtgacatcga gggagaaaac tgtggagcca    2640
ggcttgccca tcggatctcc aaatccaaat tcagccgcta ctggcgcagg tggaatcgat    2700
tctgcagaag aaaatgccgt gcagcagtta agtccaacgt cttctactgg ctcgtgatct    2760
tcctggtgtt cctcaacacc ctcaccattg cctccgaaca ttacaaccag cctcactggc    2820
tcacagaagt gcaagacaca gccaataaag ccctcctggc ccttttcact gcagaaatgc    2880
tcctgaagat gtacagcctg ggtcttcagg cctattttgt gtccctcttc aaccgctttg    2940
actgtttcat tgtgtgtggg gcatcctgg agaccatcct ggtggagacg aagatcatgt    3000
ctccctggg catctctgtg ctgagatgtg tgcggttgct caggatcttc aagatcacca    3060
ggtactggaa ttccttgagc aaccttgtgg catccttgct gaactcagtg cgctccattg    3120
cctccctgct gctgctcctc ttcctcttca tcatcatctt ctccctcctg gggatgcagc    3180
tctttggagg gaagttcaat ttcgatgaga tgcagacccg taggagcacg ttcgataact    3240
tcccgcagtc tctcctcact gtgtttcaga tcctgaccgg ggaggactgg aattcggtga    3300
tgtatgatgg gatcatggct tatggcggcc cctcttttcc agggatgtta gtctgtattt    3360
acttcatcat cctcttcatc tgtggaaatt atatcctact gaatgtgttc ttggccattg    3420
cggtggacaa cctggctgat gcggagagcc tgaccctcagc ccaaaaggag gaggaagaag    3480
agaaggagag gaagaagctg gccaggactg ccagcccaga aaagaaacag gaggtgatgg    3540
agaagccagc cgtggaggag agcaaagagg agaaaattga actgaaatcc attacagccg    3600
atggagaatc cccacccact accaagatca acatggatga cctccagccc agtgaaaacg    3660
aggataagag tccccactcc aacccagaca ctgcagggga agaggatgaa gaggagccag    3720
agatgcctgt ggggccacgc ccccggcccc tgtctgagct gcaccttaag gaaaaggcag    3780
ttcccatgcc ggaagccagt gcattttca tcttcagccc aaacaacagg ttccgcctgc    3840
agtgccaccg tattgtcaat gacacgatct tcaccaacct catcctcttc ttcattctgc    3900
tcagcagcat ctctctggct gctgaggacc ccgtccagca cacctccttc aggaaccata    3960
tcctaggcaa tgcagactat gtcttcacta gtatctttac attagaaatt atccttaaga    4020
tgactgctta cgggggctttc ctgcacaagg gctctttctg ccgaaactac ttcaatatcc    4080
tggacctgct ggtggttagc gtgtccctca tctcctttgg catccagtcc agcgcgatca    4140
acgttgtgaa gattttacga gtgctgcgag tcctcagacc cctgagggcc atcaacaggg    4200
ccaaggggct aaagcatgtg gttcagtgcg tgtttgtggc catccggacc atcgggaaca    4260
tcgtaattgt caccactctg ctgcagttca tgttcgcctg cattgggtc cagctcttca    4320
agggaaagct ctatacctgt tcggatagtt ctaaacagac ggaggcagaa tgcaagggta    4380
actatatcac atacaaagat ggagaggtcg atcaccccat tatccagcct cgaagctggg    4440
agaacagcaa gtttgacttt gacaatgttt tggcagccat gatggctctc ttcaccgtct    4500
```

```
ccaccttcga agggtggcca gagctgctgt accgctccat tgactcccac acagaagaca    4560
agggccccat ctacaactac cgtgtggaga tctccatctt cttcatcatc tatatcatca    4620
tcattgcctt cttcatgatg aacatcttcg tgggtttcgt cattgtcacc ttccaggagc    4680
aggggggaaca agagtacaag aactgtgagc tggacaagaa ccagagacaa tgtgtggaat    4740
atgccctcaa ggcccgaccc ttgcgaaggt acatccccaa gaaccagcac cagtacaaag    4800
tgtggtacgt ggtcaactct acctacttcg agtatctgat gttcgttctc atcctgctca    4860
acaccatctg cctggccatg cagcactatg ccagagctg cctcttcaaa atcgccatga    4920
atatactcaa catgcttttc accggcctct tcacagtgga gatgatcctg aagctcattg    4980
ccttcaaacc caagggttac tttagtgatc cctggaatgt ttttgacttc ctcatcgtca    5040
ttgggagcat aattgatgtc attctcagtg agactaatcc agctgaacat acccaatgct    5100
ctccctctat gagtgcagag gagaactccc gcatctccat caccttcttc cgcctcttcc    5160
gggtcatgcg cctggtgaag ctgctgagcc gcggggaagg catccgaacc ctgctgtgga    5220
ccttcatcaa gtccttccag gctctgccct atgtggctct tttgattgtg atgctgttct    5280
ttatctatgc agtgattggg atgcaggtgt ttgggaagat tgccctgaat gacaccacag    5340
agatcaatcg gaacaacaac ttccagacgt tcccccaggc tgtgttactg ctgttcaggt    5400
gtgccaccgg agaggcctgg caggacatca tgctggcctg catgccaggc aagaagtgtg    5460
ccccagagtc tgagcccagc aacagcacgg aaggggagac ccctgtggc agcagctttg    5520
ctgtcttcta cttcatcagc ttctacatgc tctgtgcctt cctgatcatc aacctctttg    5580
tagctgttat catggacaac tttgactacc tgactaggga ttggtctatc ctcggtcccc    5640
atcacctgga tgaattcaag agaatctggg ccgagtatga ccctgaagcc aagggtcgga    5700
tcaaacactt ggatgtggtg accctcctcc gtcgaattca gccccactg ggttttggga    5760
aattgtgtcc tcaccgtgtg gcctgcaaac gcctggtgtc catgaacatg cctctgaaca    5820
gcgatggcac agtcatgttc aatgctaccc tgtttgccct cgtcaggaca gccctgagga    5880
tcaaaacaga agggaaccta gagcaagcca atgaggagct tcgggccatc atcaagaaaa    5940
tctggaagag gactagcatg aagctgttgg accaggtggt gcccctgca ggcgatgacg    6000
aggtcacagt gggcaagttc tatgccacct tcctgatcca agagtacttc aggaaattca    6060
agaagcgaaa agagcagggg ctggtgggca agccctcaca aaggaatgca ctgtccctcc    6120
aggctggctt gcgcaccttg catgacattg ggcctgagat ccggcgggcc atctctgggg    6180
atctgactgc tgaggaggag ttggacaagg ctatgaagga ggcggtgtct gctgcctccg    6240
aagatgacat cttcaggagg gctggaggcc tgttcggcaa ccatgtcacc tactatcaga    6300
gtgacagcag gggcaacttt cctcagacgt tcgccaccca gcgcccactg cacatcaaca    6360
agacagggaa caaccaagct gacactgagt caccgtccca tgagaagctg gtggactcca    6420
cgttcacccc cagcagctac tcatccacgg gctccaatgc caacatcaac aatgccaaca    6480
acactgccct gggccgcttc ccccatcccg ctggctactc cagcacggtc agcactgtgg    6540
agggccatgg gcctcccttg tccctgctg tccgagtaca ggaggcagca tggaagctca    6600
gctctaagag gtgccactcc cgagagagcc agggagccac ggtgaatcag gagatatttc    6660
cagatgagac ccgcagcgta aggatgagtg aagaagccga gtactgcagt gagcccagcc    6720
tgctctccac agatatgttc tcctaccagg aagatgaaca ccgacaactg acctgcccag    6780
aggaggacaa gagggagatc cagccatctc caaagaggag tttccttcgc tctgcctctc    6840
```

```
taggtcgaag ggcctccttc catctggaat gtctaaagcg acaaaaggat caaggggag    6900
acatctctca gaagacagcc ttgcccttgc atctggttca tcatcaggca ttggcagtgg    6960
caggcttgag ccccctcctg cagagaagcc attctcctac cacattcccc aggccgtgcc    7020
ccacacccc tgtcactcca ggcagccggg gcagacccct acggcccatc cctaccctac    7080
ggctggaggg ggcagagtcc agcgagaaac tcaacagcag cttcccatcc atccactgca    7140
gctcctggtc tgaggagacg acagcctgta gtgggagcag cagcatggcc cggagagccc    7200
ggcccgtctc cctcaccgtg cccagccagg ctggagctcc agggagacag ttccatggca    7260
gtgccagcag cctggtggaa gcggtcttga tttcagaagg actgggacag tttgctcaag    7320
atcccaagtt catcgaggtc accacccagg agctggctga cgcctgcgac atgacaatag    7380
aggagatgga gaacgccgca gacaacatcc tcagtggggg cgcccagcag agccccaacg    7440
gcaccctctt accttttgtg aactgcaggg accggggca ggacagggct gtggccccag    7500
aggacgagag ctgcgcatat gccctgggc gaggccggag cgaggaggcg ctcgcggaca    7560
gcaggtccta cgtcagcaac ctgtagtcct cagggctggc gagacgcggg tggtttttt    7620
attcgtttca atgttcctaa tgggttcgtt tcagaagtgc ctcactgttc tcgtgacctg    7680
gaggtaaccg gaacagcgtc ttcattcact gctgtcggga taagcctcag agctgggcgg    7740
tgtacggagt cggcttttca ggggagaagg ccaaggccgt ggtgcggggg ctccagcacc    7800
ttccgcggca gcaccgccca aggaccccca cccccacccc tgagcaaaag ggtgttttcc    7860
ccttgcttgt ataaacagtc atttgcacat gttctgtctg agcctggccg tctctatgga    7920
gcagggcccc agggatctat ggcaggaatg ggccagcgcc cccagtagga gccgggaggt    7980
ggctgcgagg ttcccagcag tgcaggtctg gtccctatgg tcccttcagg gactcttttcc    8040
ctgcaaggag ctgagatgca ggtggcagga gccagtgcag atcacaccac ccgccctcag    8100
ctagccaggc caggggggcg caggctgctg cctggtgctc ggggtttcat ggtttgaggg    8160
ttcttgtcag catgttgcga ctttctgggg tttggtttct ttattactat ttgttgtgtt    8220
ttcccacggg gagggagga ataagagcgg ttacaactgc gcggcctcac ttcactgttt    8280
ccacatttgc atttgcgtat ttaagtcgga tttggtttga ttgtattctt taaatggtgc    8340
ggtccacccc caccgccacc cccacccccc actggagcaa gggttcaata tcaccagaga    8400
aaggttttac ctgctctgtg tctgcccagt aacttgttcc aatttcctta agtaaaagca    8460
acttttttct ttctttcgag tttggttgag catcacaatc agcaggctaa caggcagtta    8520
gatcaggcgg tgtgcgcctg ggcgattgag ctgggctcct ttctgtgctg ggcatatgga    8580
ctggttcaag agagaagaaa tatgggcatc tttgtgtcac acttgtgtcc atagtatgtg    8640
cgtatgtgca cccacgtggt atgtgtgcgc cccaccccac ccctgcacaa aagcctgtag    8700
aaccccgttt gggtttgact gcagggagtt ctaaatctgg ggctatttga agcaagaac    8760
aaaccactgt ctctgcttct gcttctgaaa cgagaatcgg taactgcatt tttctgtccc    8820
acgagatatg caaaagcaat gcaataatat ccattttaaa atatggttgt gagttgtgtc    8880
agcattaaaa ttctattta aaaaaaaaac cacgaaattt aagggaaaa ctcaagaaga    8940
cattttgctt cgatatattc tgtgtaatgt tttattgcat tgataatgtt tctgttgaag    9000
aaactgttat actt                                                       9014
```

<210> SEQ ID NO 10
<211> LENGTH: 7648
<212> TYPE: DNA
<213> ORGANISM: Homo sapiens

<400> SEQUENCE: 10

| | | | | | |
|---|---|---|---|---|---|
| atggacgagg | aggaggatgg | agcgggcgcc | gaggagtcgg | gacagccccg | gagcttcatg | 60
| cggctcaacg | acctgtcggg | ggccggggc | cggccggggc | cggggtcagc | agaaaaggac | 120
| ccgggcagcg | cggactccga | ggcggagggg | ctgccgtacc | cggcgctggc | cccggtggtt | 180
| ttcttctact | tgagccagga | cagccgcccg | cggagctggt | gtctccgcac | ggtctgtaac | 240
| ccctggtttg | agcgcatcag | catgttggtc | atccttctca | actgcgtgac | cctgggcatg | 300
| ttccggccat | gcgaggacat | cgcctgtgac | tcccagcgct | gccggatcct | gcaggccttt | 360
| gatgacttca | tctttgcctt | ctttgccgtg | agatggtgg | tgaagatggt | ggccttgggc | 420
| atctttggga | aaaagtgtta | cctgggagac | acttggaacc | ggcttgactt | tttcatcgtc | 480
| atcgcaggga | tgctggagta | ctcgctggac | ctgcagaacg | tcagcttctc | agctgtcagg | 540
| acagtccgtg | tgctgcgacc | gctcaggggcc | attaaccggg | tgcccagcat | gcgcatcctt | 600
| gtcacgttgc | tgctggatac | gctgcccatg | ctgggcaacg | tcctgctgct | ctgcttcttc | 660
| gtcttcttca | tcttcggcat | cgtcggcgtc | cagctgtggg | cagggctgct | tcggaaccga | 720
| tgcttcctac | ctgagaattt | cagcctcccc | ctgagcgtgg | acctggagcg | ctattaccag | 780
| acagagaacg | aggatgagag | ccccttcatc | tgctcccagc | cacgcgagaa | cggcatgcgg | 840
| tcctgcagaa | gcgtgcccac | gctgcgcggg | acgggggcg | gtggcccacc | ttgcggtctg | 900
| gactatgagg | cctacaacag | ctccagcaac | accacctgtg | tcaactggaa | ccagtactac | 960
| accaactgct | cagcggggga | gcacaacccc | ttcaagggcg | ccatcaactt | tgacaacatt | 1020
| ggctatgcct | ggatcgccat | cttccaggtc | atcacgctgg | agggctgggt | cgacatcatg | 1080
| tactttgtga | tggatgctca | ttccttctac | aatttcatct | acttcatcct | cctcatcatc | 1140
| gtgggctcct | tcttcatgat | caacctgtgc | ctggtggtga | ttgccacgca | gttctcagag | 1200
| accaagcagc | gggaaagcca | gctgatgcgg | gagcagcgtg | tgcggttcct | gtccaacgcc | 1260
| agcaccctgg | ctagcttctc | tgagcccggc | agctgctatg | aggagctgct | caagtacctg | 1320
| gtgtacatcc | ttcgtaaggc | agcccgcagg | ctggctcagg | tctctcgggc | agcaggtgtg | 1380
| cgggttgggc | tgctcagcag | cccagcaccc | ctcgggggcc | aggagaccca | gcccagcagc | 1440
| agctgctctc | gctcccaccg | ccgcctatcc | gtccaccacc | tggtgcacca | ccaccaccac | 1500
| catcaccacc | actaccacct | gggcaatggg | acgctcaggg | ccccccgggc | cagcccggag | 1560
| atccaggaca | gggatgccaa | tgggtcccgc | aggctcatgc | tgccaccacc | ctcgacgcct | 1620
| gccctctccg | ggggccccccc | tggtggcgca | gagtctgtgc | acagcttcta | ccatgccgac | 1680
| tgccacttag | agccagtccg | ctgccaggcg | cccccctccca | ggtccccatc | tgaggcatcc | 1740
| ggcaggactg | tgggcagcgg | gaaggtgtat | cccaccgtgc | acaccagccc | tccaccggag | 1800
| acgctgaagg | agaaggcact | agtagaggtg | gctgccagct | ctgggccccc | aaccctcacc | 1860
| agcctcaaca | tcccacccgg | gccctacagc | tccatgcaca | agctgctgga | gacacagagt | 1920
| acaggtgcct | gccaaagctc | ttgcaagatc | tccagcccctt | gcttgaaagc | agacagtgga | 1980
| gcctgtggtc | cagacagctg | cccctactgt | gcccgggccg | ggcaggggga | ggtggagctc | 2040
| gccgaccgtg | aaatgcctga | ctcagacagc | gaggcagttt | atgagttcac | acaggatgcc | 2100
| cagcacagcg | acctccggga | cccccacagc | cggcggcaac | ggagcctggg | cccagatgca | 2160
| gagcccagct | ctgtgctggc | cttctggagg | ctaatctgtg | acaccttccg | aaagattgtg | 2220
| gacagcaagt | actttggccg | gggaatcatg | atcgccatcc | tggtcaacac | actcagcatg | 2280

```
ggcatcgaat accacgagca gcccgaggag cttaccaacg ccctagaaat cagcaacatc    2340
gtcttcacca gcctctttgc cctggagatg ctgctgaagc tgcttgtgta tggtcccttt    2400
ggctacatca agaatcccta caacatcttc gatggtgtca ttgtggtcat cagcgtgtgg    2460
gagatcgtgg gccagcaggg gggcggcctg tcggtgctgc ggaccttccg cctgatgcgt    2520
gtgctgaagc tggtgcgctt cctgccggcg ctgcagcggc agctggtggt gctcatgaag    2580
accatggaca acgtggccac cttctgcatg ctgcttatgc tcttcatctt catcttcagc    2640
atcctgggca tgcatctctt cggctgcaag tttgcctctg agcgggatgg ggacaccctg    2700
ccagaccgga agaattttga ctccttgctc tgggccatcg tcactgtctt tcagatcctg    2760
acccaggagg actggaacaa agtcctctac aatggtatgg cctccacgtc gtcctgggcg    2820
gccctttatt tcattgccct catgaccttc ggcaactacg tgctcttcaa tttgctggtc    2880
gccattctgg tggagggctt ccaggcggag gaaatcagca acgggaaga tgcgagtgga    2940 cagttaagct gtattcagct gcctgtcgac tcccaggggg gagatgccaa caagtccgaa    3000
tcagagcccg atttcttctc acccagcctg gatggtgatg ggacaggaa gaagtgcttg    3060 gccttggtgt ccctgggaga gcacccggag ctgcggaaga gcctgctgcc gcctctcatc    3120
atccacacgg ccgccacacc catgtcgctg cccaagagca ccagcacggg cctgggcgag    3180
gcgctgggcc ctgcgtcgcg ccgcaccagc agcagcgggt cggcagagcc tggggcggcc    3240
cacgagatga agtcaccgcc cagcgcccgc agctctccgc acagcccctg gagcgctgca    3300
agcagctgga ccagcaggcg ctccagccgg aacagcctcg gccgtgcacc cagcctgaag    3360
cggagaagcc caagtggaga gcggcggtcc ctgttgtcgg gagaaggcca ggagagccag    3420
gatgaagagg agagctcaga agaggagcgg gccagccctg cgggcagtga ccatcgccac    3480
agggggtccc tggagcggga ggccaagagt tcctttgacc tgccagacac actgcaggtg    3540
ccagggctgc atcgcactgc cagtggccga gggtctgctt ctgagcacca ggactgcaat    3600
ggcaagtcgg cttcagggcg cctggcccgg gccctgcggc ctgatgaccc ccactggat    3660 ggggatgacg ccgatgacga gggcaacctg agcaaagggg aacgggtccg cgcgtggatc    3720
cgagcccgac tccctgcctg ctgcctcgag cgagactcct ggtcagccta catcttccct    3780
cctcagtcca ggttccgcct cctgtgtcac cggatcatca cccacaagat gttcgaccac    3840
gtggtccttg tcatcatctt ccttaactgc atcaccatcg ccatggagcg ccccaaaatt    3900
gacccccaca cgcgctgaacg catcttcctg accctctcca attacatctt caccgcagtc    3960
tttctggctg aaatgacagt gaaggtggtg gcactgggct ggtgcttcgg ggagcaggcg    4020
tacctgcgga gcagttggaa cgtgctggac gggctgttgg tgctcatctc cgtcatcgac    4080
attctggtgt ccatggtctc tgacagcggc accaagatcc tgggcatgct gagggtgctg    4140
cggctgctgc ggaccctgcg cccgctcagg gtgatcagcc gggcgcaggg gctgaagctg    4200
gtggtggaga cgctgatgtc ctcactgaaa cccatcggca acattgtagt catctgctgt    4260
gccttcttca tcattttcgg catcttgggg gtgcagctct tcaaagggaa gtttttcgtg    4320
tgccaggggc ggatacccag gaacatcacc aataaatcgg actgtgccga ggccagttac    4380
cggtgggtcc ggcacaagta caacttgac aaccttggcc aggccctgat gtccctgttc    4440
gttttggcct ccaaggatgg ttgggtggac atcatgtacg atgggctgga tgctgtgggc    4500
gtggaccagc agcccatcat gaaccacaac ccctggatgc tgctgtactt catctcgttc    4560
ctgctcattg tggccttctt tgtcctgaac atgtttgtgg gtgtggtggt ggagaacttc    4620
cacaagtgtc ggcagcacca ggaggaagag gaggcccggc ggcgggagga gaagcgccta    4680
```

```
cgaagactgg agaaaaagag aaggaatcta atgctggacg atgtaattgc ttccggcagc   4740
tcagccagcg ctgcgtcaga agcccagtgc aaaccttact actccgacta ctcccgcttc   4800
cggctcctcg tccaccactt gtgcaccagc cactacctgg acctcttcat cacaggtgtc   4860
atcgggctga acgtggtcac catggccatg agcactacc agcagcccca gattctggat    4920
gaggctctga agatctgcaa ctacatcttc actgtcatct ttgtcttgga gtcagttttc   4980
aaacttgtgg cctttggttt ccgtcggttc ttccaggaca ggtggaacca gctggacctg   5040
gccattgtgc tgctgtccat catgggcatc acgctggagg aaatcgaggt caacgcctcg   5100
ctgcccatca accccaccat catccgcatc atgagggtgc tgcgcattgc ccgagtgctg   5160
aagctgctga gatggctgt gggcatgcgg gcgctgctgg acacggtgat gcaggccctg    5220
ccccaggtgg ggaacctggg acttctcttc atgttgttgt ttttcatctt tgcagctctg   5280
ggcgtggagc tctttggaga cctggagtgt gacgagacac accctgtga gggcctgggc    5340 cgtcatgcca ccttcggaa ctttggcatg gccttcctaa ccctcttccg agtctccaca    5400
ggtgacaatt ggaatggcat tatgaaggac accctccggg actgtgacca ggagtccacc   5460
tgctacaaca cggtcatctc gcctatctac tttgtgtcct tcgtgctgac ggcccagttc   5520
gtgctagtca acgtggtgat cgccgtgctg atgaagcacc tggaggagag caacaaggag   5580
gccaaggagg aggccgagct agaggctgag ctggagctgg agatgaagac cctcagcccc   5640
cagccccact cgccactggg cagccccttc ctctggcctg gggtcgaggg ccccgacagc   5700
cccgacagcc ccaagcctgg ggctctgcac ccagcggccc acgcgagatc agcctcccac   5760 tttccctgg agcaccccac ggacaggcag ctgtttgaca ccatatccct gctgatccag    5820
ggctccctga gtgggagct gaagctgatg acgagctgg caggcccagg gggccagccc    5880
tctgccttcc cttctgcccc cagcctggga ggctccgacc cacagatccc tctagctgag   5940
atggaggctc tgtctctgac gtcagagatt gtgtctgaac cgtcctgctc tctagctctg   6000
acggatgact ctttgcctga tgacatgcac acactcttac ttagtgccct ggagagcaat   6060
atgcagcccc accccacgga gctgccagga ccagactac tgactgtgcg gaagtctggg     6120
gtcagccgaa cgcactctct gcccaatgac agctacatgt gtcggcatgg gagcactgcc   6180
gaggggcccc tgggacacag gggctggggg ctccccaaag ctcagtcagg ctccgtcttg   6240
tccgttcact cccagccagc agataccagc tacatcctgc agcttcccaa agatgcacct   6300
catctgctcc agcccacag cgccccaacc tggggcacca tccccaaact gccccccacca   6360 ggacgctccc ctttggctca gaggccactc aggcgccagg cagcaataag gactgactcc   6420
ttggacgttc agggtctggg cagccgggaa gacctgctgg cagaggtgag tgggccctcc   6480
ccgcccctgg cccgggccta ctctttctgg ggccagtcaa gtacccaggc acagcagcac   6540
tcccgcagcc acagcaagat ctccaagcac atgacccgc cagccccttg cccaggccca    6600
gaacccaact ggggcaaggg ccctccagag accagaagca gcttagagtt ggacacggag   6660
ctgagctgga tttcaggaga cctcctgccc cctggcggcc aggaggagcc cccatcccca   6720
cgggacctga agaagtgcta cagcgtggag gcccagagct gccagcgccg gcctacgtcc   6780
tggctggatg agcagaggag acactctatc gccgtcagct gcctggacag cggctcccaa   6840
ccccacctgg gcacagaccc ctctaacctt ggggggccagc tcttgggggg gctgggagc   6900 cggcccaaga aaaaactcag cccgcctagt atcaccatag accccccga gagccaaggt    6960 cctcggaccc cgcccagccc tggtatctgc ctccggagga gggctccgtc cagcgactcc   7020
```

-continued

| | |
|---|---|
| aaggatccct tggcctctgg ccccctgac agcatggctg cctcgccctc cccaaagaaa | 7080 |
| gatgtgctga gtctctccgg tttatcctct gacccagcag acctggaccc ctgagtcctg | 7140 |
| ccccactttc ccactcacct ttctccactg ggtgccaagt cctagctcct cctcctgggc | 7200 |
| tatattcctg acaaaagttc catatagaca ccaaggaggc ggaggcgctc ctccctgcct | 7260 |
| cagtggctct gggtacctgc aagcagaact tccaaagaga gttaaaagca gcagccccgg | 7320 |
| caactctggc tccaggcaga aggagaggcc cggtgcagct gaggttcccg acaccagaag | 7380 |
| ctgttgggag aaagcaatac gtttgtgcag aatctctatg tatattctat tttattaaat | 7440 |
| taattgaatc tagtatatgc gggatgtacg acattttgtg actgaagaga cttgtttcct | 7500 |
| tctactttta tgtgtctcag aatattttg aggcgaaggc gtctgtctct tggctatttt | 7560 |
| aacctaaaat aacagtctag ttatattccc tcttcttgca aagcacaagc tgggaccgcg | 7620 |
| agcacattgc agccccaacg gtggccca | 7648 |

<210> SEQ ID NO 11
<211> LENGTH: 6073
<212> TYPE: DNA
<213> ORGANISM: Caenorhabditis elegans

<400> SEQUENCE: 11

| | |
|---|---|
| accactttga cccggtcacc tgaaaatgct acgtcagcca gttccggaac tgcgcagttt | 60 |
| tcagtccctc tctaaatatg caggcggacc gagatcagtt ctcggtagga gaacatcagc | 120 |
| aatcacagtc aatcgaagac aatcacaatc gacacgacga catgaggatg ttgaggcact | 180 |
| gggctcgatc gaaggctcga agaaaactct gcagctgtcg gaacacggac gattggcctc | 240 |
| ctcctcggag gcctcccctt ctcggtggga gggccgacag atcgagtggg ggaatgaaga | 300 |
| gcaaattgaa gaggaaagtg aacttccgta tccggggttt gctgagccag cacttcgatg | 360 |
| tttttatcaa gccagacctc caaggaaatg ggcgcttcaa atggtgatga gtccttggtt | 420 |
| tgaccgaata acaatggctg tgattatgat taattgtgta accctcggga tgtacaggcc | 480 |
| ttgtgaagat ggtccagact gtgacactta ccggtgtcaa atccttgata taattgacaa | 540 |
| ttgcatattt gtctattttg catttgaaat ggtgataaaa ataatggctc tagggtttta | 600 |
| cggtcctgcg gcttatatgt ctgatacatg gaatcgtctg gacttttca ttgttatggc | 660 |
| aggaatcgct gagtttgtat tacacgagta tctcggagga aacatcaatt taacagcaat | 720 |
| cagaacggtt cgagtactga ggccgcttcg agcggtcaat cgaataccat cgatgaggat | 780 |
| tttagtcaat ttgttactcg acacattacc catgcttgga aatgtgcttc ttttatgttt | 840 |
| tttcgttttc ttcattttg gaattgttgg tgttcaatta tgggcgggtt tattacgaaa | 900 |
| tcgatgtgtc attaatttac caaaacaat atcgagaat caatctgcgt tgttcaacaa | 960 |
| tgtaaaactg acaaggtttt acattccgga agacacatcg ctagaatata tttgcagtca | 1020 |
| accagacgca aacgggttac acacttgctc aaatcttcca ccatacactg tcgacggagt | 1080 |
| gaagtgtaac cttacactag atgaatacga caaagtaacg aacgactctt gtatcaactg | 1140 |
| gaatatttat tacaacgaat gtcaggtgat gcaacgaaat ccatttcaag gatcagtttc | 1200 |
| tttcgacaat atcggttttg cgtgggtcgc tattttctc gtcatatcac ttgaagggtg | 1260 |
| gacggatata atgtactatg tacaggacgc tcattctttt tggaattgga tctattttgt | 1320 |
| tcttctcatt gtgatcggtg cttttttcat gatcaatcta tgccttgttg ttattgctac | 1380 |
| tcagtttgct gaaacaaagc ggcgggagac tgaacgaatg ctacaagaac gaaaaatgct | 1440 |
| actaaataga gattctatat cgtgtactgg aagtgagatt ggtggcgctt cttccaaaga | 1500 |

-continued

```
agaaggagat actgtttatg cagcttttgt tagatttatc ggacacacct ttcggagaac    1560
aaaacgagca gcgaaaaaaa agtacactgc ctacatggaa gaaagagcag agcgaaaaag    1620
ttccgaacga caacaacgga ggaagtcaaa acttgatgat atggccacac tttcaaggat    1680
cgaggaaaaa gctgaagacg aagaagatga aaccaccata actcgtgaaa acggagatga    1740
tcaaatcgag caaaatggtg atggagtccg gataaagcgc gtaaaaattg aagaagaacc    1800
caagatcaaa ataggaaacg gtaattcgaa tggaccgcat tacaaacact ccagcagcga    1860
tgaagaatct gatgaggatg gcgaagagga ccaagtttac gatggggaag aagccaagaa    1920
gaagagtaca ccttccaagc tctggtggtt tcgagaaaaa attcagaaat tcgttatttg    1980
tgatcacttc actagaggga ttcttgttgc aattttggtg aatacgttga gcatgggtgt    2040
ggagtaccat caacaaccgg aaatattaac tgtcattctg gaatattcga atttattttt    2100
cactgctttg tttgctttgg aaatgcttct taagatcatt gcaagtggat gtttggtta    2160 tttagctgat ggattcaacc ttttcgacgg aggaattgtc gcattgagtg ttcttgagtt    2220
atttcaagaa ggtaaaggag gtctatcagt tcttcgtact tttcgccttc ttcgaattct    2280
gaaattggtt cgcttcatgc ctgctcttcg atatcaactg gttgtgatgc tccgaacaat    2340
ggacaatgtc actgtgtttt ttggactttt ggttcttttc atctttatct tcagcattct    2400
cggaatgaat ctgtttgggt gcaaattttg caaagtcgaa gagaaatttc ttggaggcct    2460
tgcgaaaaag tgtgaaagaa aaactttga cacgttgctc tgggcgctga tcactgtgtt    2520
tcagattctt acacaagaag attggaacat ggttttattc aacggtatgg ctcaaacaaa    2580
cccatgggca gctctttact ttgtggcgct catgacattt ggtaattacg ttcttttcaa    2640
cttacttgta gctatcttgg tagaaggatt ccaagaaagc aaggaagaag aaaagcgaca    2700
attggaagag gatgcgagaa agcaagctgt agaagaagaa gacgaaagaa agcgagaatt    2760
ggagcttata attgccaaaa caacgtcacc tgctttcaat aatggagtag cacctgcaga    2820
atgtacttgt caaagaccat cctccccgga agaatcacca tctccgagat gctgtctgc    2880 aaattaccac ccatctcctg aaaggaaaca ctctgcaaat ttggatgcca tcattgataa    2940
aagattagtt ctaagaaatt cggcaccttt cgatagatca ccagtatctg aaggacgtga    3000
tgattctaga ctcaatcgtc acgccagtct tgtacttcct gtcgctaatg gagttccgta    3060
tcggcgacaa agagttcaca gttggagtgg gctttgtcat catttcaatc cgaactgccc    3120
tgtacatgga agaagagcac tcattgaaac ttatgcacga gaaaaatttc tagaagctag    3180
tcaagagcta aaacaggctc tcgctgagga agaaaaaaga aatgaagcca agcaaaacac    3240
gtttgtgaga aaacttttga aaaaaacgtg ccttcacaac cgaactgaat tttcactatt    3300
tcttatgggc ccaaaaaacc cgctacgcat aaaatgccta caaacaactc aaaagaaatg    3360
gttcgattac accgtattgt ttttcattgg aatcaactgt ataacactgg ctatggaacg    3420
accatcaatt cctcctgata gttttgaaag gcaatttctt catatttctg ggtacatttt    3480
cacagtgatt tttactggtg aaatgatgat gaaggttatt gcaaatggtt gtttcattgg    3540
gcaagcagcg tattttaaag atggttggaa cattctcgat ggaattcttg ttgtcatttc    3600
cttaatcaac attgcgtttg aacttctggc aactggcgat tctccaaaaa tatttggtgt    3660
tataagagtg ttaaggctac ttcgtgcatt gaggccttta cgagttatca ataggctcc    3720 gggagttaag cttgtagtaa tgacattaat atccagtctg aaacctatcg gaaacattgt    3780
tctgatttgc tgcacattct tcattatctt tggcatcctc ggtgttcagt tgttcaaagg    3840
```

```
tatgatgtac cattgcattg gacctgaagt tggaaacgtt acaacaaaag cggattgcat    3900
tgaagattac cgaaacaaat gggttaatca tcgttacaac tttgacaacc tcggtcaggc    3960
tcttatgtca cttttcgttc tttcaagtaa agatggatgg gtctcgatca tgtatcaagg    4020
aatcgacgct gtaggggttg acgtgcaacc aattgagaat tacaatgaat ggagaatgat    4080
ttactttatt tcattcttat tgcttgttgg attctttgtg ctgaacatgt tcgtaggagt    4140
tgtggttgag aactttcata agtgcaaaga agcattggaa aaagaaatga gagaaaaaga    4200
gaaagaaaag aggctgaaga gaaagctgaa acggcagaag tttgaggaga gtatggctgg    4260
aaaacggaaa aaaatggaaa ggaattatcc ttattaccat gattatggtc atacaaggct    4320
tttcttgcac ggaattgtca cctccaaata cttcgaccta gcgatcgccg cagtaattgg    4380
tatcaatgtc atatctatgg ctatggagtt ctatatgatg ccaatgggac tgaaatacgt    4440
tctcaaagct ctcaattact ttttcacagc agtcttcaca ctagaagctg ctatgaagct    4500
gattgctttg ggttttaaac gtttctttat tgaaaaatgg aatcgcttgg atatgttcat    4560
tgttattttg tctattgcgg gcataatttt cgaagagttt gaagctctcg aacttccaat    4620
taatccaaca atcattcgtg tcatgcgagt gctccggata gccagagttc tgaaactgct    4680
gaaaatggcc aaaggaattc gatcattgtt ggacacagtg ggagaagcgt tgccccaggt    4740
tggaaatctc gggtctctgt tcttccttct tttcttcata tttgctgcac ttggtgttga    4800
actgtttgga aaactggagt gctctgaaga tcatccgtgt gatggattag gagaacatgc    4860
gcatttaaaa aattttggaa tggcttttt aacactcttt cgaatagcga cgggtgataa    4920
ttggaatgga attatgaagg atgccctccg tgatgactgt gattcctccg atcactgtga    4980
aacaaactgc tgcgttgatc caatcctggc accatgcttc ttcgtaattt tcgtcttgat    5040
ctcacaattt gtacttgtca atgtagtagt cgctgtactt atgaaacatc tggaagaaag    5100
taacaagcga gatgcggaag gaccggcaga accaacaggt gaaaacatcg agaacgagat    5160
cacaaagtcc gacgatgacg aaattgtgga agaacacgaa ccactcgcaa ttgaacatgt    5220
taaagagggt gaacttgatg aagaagaaga gacagaagaa ggtcccacca ctcaaatacc    5280
agacgggcat ggtggtatta acggttatc catgcaggtt ctggaacaag aattaatcga    5340
agtcgagaga catttggaag aaagatatcg gagggcaagc gagtgtctcg gcggagaact    5400
tcagcctttg aatcccggag agatcgaaga tctagacgat cccgagttca gaccacggag    5460
tagatcacat agaccacgag caagaacaaa cagtgcgttg agcaataaaa gccgtggatc    5520
acacaagtct gctttatagc ctattcactt atcaagaaga aaatatcatc aacttttttt    5580
gcaattttc atagttgtat atccaccca ctttttatgg aaccatctca tatttagaat    5640
tctttgcttt gccaaaacct ttggttgatc aatatcagat tgttcgttta ttactggtaa    5700
catttgtcat aactcaaaaa atccctcttt tttcaatttc cctctgaacc tttttttatcg   5760
catgtatgaa acttgtatga aagaatttga aacaaataaa acgaaaccta tgctttttc    5820
aattgtcaac ttatatttcc ggtccatgtt tcctctactt ttcgcttctg catttcattt    5880
gccttcctgt tagaaattaa atctacttga aaagaactg catcttccaa agtgttcact    5940
tcaaactgat cttttctgat gtttaatatt gttcgaaatt ctaatatcaa ctattttctt    6000
ggtttattgc ttttttgtct ttttgtcttt tgtcttcttt ccttcattc attattgaaa    6060
aaatgaataa ttg                                                      6073

<210> SEQ ID NO 12
<211> LENGTH: 5905
```

<212> TYPE: DNA
<213> ORGANISM: Rattus norvegicus

<400> SEQUENCE: 12

```
tctggagcca tacggtgccc tgatcctctg taccaggaag acagggtgaa gatggaggag      60
aggtactacc cggtgatctt cccggacgag cggaatttcc gccccttcac ttccgactct     120
ctggctgcca tagagaagcg gattgctatc caaaaggaga ggaagaagtc caaagacaag     180
gcggcagctg agcccagcc tcggcctcag cttgacctaa aggcctccag gaagttacct     240
aagctttatg gtgacattcc ccctgagctt gtagcgaagc ctctggaaga cctggaccca     300
ttctacaaag accataagac attcatggtg ttgaacaaga agagaacaat ttatcgcttc     360
agcgccaagc gggccttgtt cattctgggg ccttttaatc ccctcagaag cttaatgatt     420
cgtatctctg tccattcagt ctttagcatg ttcatcatct gcacggtgat catcaactgt     480
atgttcatgg cgaattctat ggagagaagt ttcgacaacg acattcccga atacgtcttc     540
attgggattt atattttaga agctgtgatt aaaatattgg caagaggctt cattgtggat     600
gagttttcct tcctccgaga tccgtggaac tggctggact tcattgtcat ggaacagcg      660
atcgcaactt gttttccggg cagccaagtc aatctttcag ctcttcgtac cttccgagtg     720
ttcagagctc tgaaggcgat ttcagttatc tcaggtctga aggtcatcgt aggtgccctg     780
ctgcgctcgg tgaagaagct ggtagacgtg atggtcctca ctctcttctg cctcagcatc     840
tttgccctgg tcggtcagca gctgttcatg ggaattctga accagaagtg tattaagcac     900
aactgtggcc ccaaccctgc atccaacaag gattgctttg aaaaggaaaa agatagcgaa     960
gacttcataa tgtgtggtac ctggctcggc agcagaccct gtcccaatgg ttctacgtgc    1020
gataaaacca cattgaaccc agacaataat tatacaaagt tgacaacttt ggctggtcc     1080
tttctcgcca tgttccgggt tatgactcaa gactcctggg agaggcttta ccgacagatc    1140
ctgcggacct ctgggatcta ctttgtcttc ttcttcgtgg tggtcatctt cctgggctcc    1200
ttctacctgc ttaacctaac cctggctgtt gtcaccatgg cttatgaaga acagaacaga    1260
aatgtagctg ctgagacaga ggccaaggag aaaatgtttc aggaagccca gcagctgtta    1320
agggaggaga aggaggctct ggttgccatg ggaattgaca aagttccct taattcccctt     1380
caagcttcat cctttcccc gaagaagagg aagttttcg gtagtaagac aagaaagtcc     1440
ttctttatga gagggtccaa gacggcccaa gcctcagcgt ctgattcaga ggacgatgcc    1500
tctaaaaatc cacagctcct tgagcagacc aaacgactgt cccagaactt gccagtggat    1560
ctctttgatg agcacgtgga ccccctccac aggcagagag cgctgagcgc tgtcagtatc    1620
ttaaccatca ccatgcagga acaagaaaaa ttccaggagc cttgtttccc atgtgggaaa    1680
aatttggcct ctaagtacct ggtgtgggac tgtagccctc agtggctgtg cataaagaag    1740
gtcctgcgga ccatcatgac ggatcccttt actgagctgg ccatcaccat ctgcatcatc    1800
atcaataccg ttttcttagc cgtggagcac cacaacatgg atgacaactt aaagaccata    1860
ctgaaaatag aaactgggt tttcacggga attttcatag cggaaatgtg tctcaagatc    1920
atcgcgctcg acccttacca ctacttccgg cacggctgga atgtttttga cagcatcgtg    1980
gccctcctga gtcgctga tgtgctctac aacacactgt ctgataacaa taggtctttc    2040
ttggcttccc tcagagtgct gagggtcttc aagttagcca atcctggcc cacgttaaac    2100
actctcatta agatcatcgg ccactccgtg ggcgcgcttg gaaacctgac tgtggtcctg    2160
actatcgtgg tcttcatctt ttctgtggtg ggcatgcggc tcttcggcac caagtttaac    2220
```

| | | | | |
|---|---|---|---|---|
| aagaccgcct | acgccaccca | ggagcggccc | aggcggcgct | ggcacatgga | taatttctac | 2280 |
| cactccttcc | tggtggtgtt | ccgcatcctc | tgtggggaat | ggatcgagaa | catgtggggc | 2340 |
| tgcatgcagg | atatgacgg | ctccccgttg | tgcatcattg | tctttgtcct | gataatggtg | 2400 |
| atcgggaagc | ttgtggtgct | taacctcttc | attgccttgc | tgctcaattc | cttcagcaat | 2460 |
| gaggagaagg | atgggagcct | ggaaggagag | accaggaaaa | ccaaagtgca | gctagccctg | 2520 |
| gatcggttcc | gccgggcctt | ctccttcatg | ctgcacgctc | ttcagagttt | tgttgcaag | 2580 |
| aaatgcagga | ggaaaaactc | gccaaagcca | aagagacaa | cagaaagctt | tgctggtgag | 2640 |
| aataaagact | caatcctccc | ggatgcgagg | ccctggaagg | agtatgatac | agacatggct | 2700 |
| ttgtacactg | acaggccgg | ggctccgctg | gccccactcg | cagaggtaga | ggacgatgtg | 2760 |
| gaatattgtg | gtgaaggcgg | tgccctaccc | acctcacaac | atagtgctgg | agttcaggcc | 2820 |
| ggtgacctcc | ctccagagac | caagcagctc | actagcccgg | atgaccaagg | ggttgaaatg | 2880 |
| gaagtatttt | ctgaagaaga | tctgcattta | agcatacaga | gtcctcgaaa | gaagtctgac | 2940 |
| gcagtgagca | tgctctcgga | atgcagcaca | attgacctga | atgatatctt | tagaaattta | 3000 |
| cagaaaacag | tttcccccaa | aaagcagcca | gatagatgct | ttcccaaggg | ccttagttgt | 3060 |
| cactttctat | gccacaaaac | agacaagaga | aagtccccct | gggtcctgtg | gtggaacatt | 3120 |
| cggaaaacct | gctaccaaat | cgtgaagcac | agctggtttg | agagtttcat | aatctttgtt | 3180 |
| attctgctga | gcagtggagc | gctgatattt | gaagatgtca | atctccccag | ccggccccaa | 3240 |
| gttgagaaat | tactaaggtg | taccgataat | attttcacat | ttattttcct | cctggaaatg | 3300 |
| atcctgaagt | gggtggcctt | tggattccgg | aggtatttca | ccagtgcctg | gtgctggctt | 3360 |
| gatttcctca | ttgtggtggt | gtctgtgctc | agtctcatga | atctaccaag | cttgaagtcc | 3420 |
| ttccggactc | tgcgggccct | gagacctctg | cgggcgctgt | cccagtttga | aggaatgaag | 3480 |
| gttgcgtct | acgccctgat | cagcgccata | cctgccattc | tcaatgtctt | gctggtctgc | 3540 |
| ctcatttct | ggctcgtatt | ttgtatcttg | ggagtaaatt | tattttctgg | gaagtttgga | 3600 |
| aggtgcatta | acgggacaga | cataaatatg | tatttggatt | ttaccgaagt | tccgaaccga | 3660 |
| agccaatgta | acattagtaa | ttactcgtgg | aaggtcccgc | aggtcaactt | tgacaacgtg | 3720 |
| gggaatgcct | atctcgccct | gctgcaagtg | gcaacctata | agggctggct | ggaaatcatg | 3780 |
| aatgctgctg | tcgattccag | agagaaagac | gagcagccgg | actttgaggc | gaacctctac | 3840 |
| gcgtatctct | actttgtggt | ttttatcatc | ttcggctcct | tctttaccct | gaacctcttt | 3900 |
| atcggtgtta | ttattgacaa | cttcaatcag | cagcagaaaa | agttaggtgg | ccaagacatt | 3960 |
| tttatgacag | aagaacagaa | gaaatattac | aatgcaatga | aaagttagg | aaccaagaaa | 4020 |
| cctcaaaagc | ccatcccaag | gcccctgaac | aaatgtcaag | cctttgtgtt | cgacctggtc | 4080 |
| acaagccagg | tctttgacgt | catcattctg | ggtcttattg | tcttaaatat | gattatcatg | 4140 |
| atggctgaat | ctgccgacca | gcccaaagat | gtgaagaaaa | cctttgatat | cctcaacata | 4200 |
| gccttcgtgg | tcatctttac | catagagtgt | ctcatcaaag | tctttgcttt | gaggcaacac | 4260 |
| tacttcacca | atggctggaa | cttatttgat | tgtgtggtcg | tggttctttc | tatcattagt | 4320 |
| accctggttt | cccgcttgga | ggacagtgac | atttcttcc | cgcccacgct | cttcagagtc | 4380 |
| gtccgcttgg | ctcggattgg | tcgaatcctc | aggctggtcc | gggctgcccg | gggaatcagg | 4440 |
| accctcctct | tgctttgat | gatgtctctc | ccctctctct | tcaacatcgg | tctgctgctc | 4500 |
| ttcctggtga | tgttcattta | cgccatcttt | gggatgagct | ggtttccaa | agtgaagaag | 4560 |
| ggctccggga | tcgacgacat | cttcaacttc | gagacctta | cgggcagcat | gctgtgcctc | 4620 |

```
ttccagataa ccacttcggc tggctgggat accctcctca accccatgct ggaggcaaaa    4680
gaacactgca actcctcctc ccaagacagc tgtcagcagc cgcagatagc cgtcgtctac    4740
ttcgtcagtt acatcatcat ctccttcctc atcgtggtca acatgtacat cgctgtgatc    4800
ctcgagaact tcaacacagc cacggaggag agcgaggacc ctctgggaga ggacgacttt    4860
gaaatcttct atgaggtctg ggagaagttt gaccccgagg cgtcgcagtt catccagtat    4920
tcggccctct ctgactttgc ggacgccctg ccggagccgt tgcgtgtggc caagccgaat    4980
aagtttcagt tctagtgat ggacttgccc atggtgatgg cgaccgcct ccattgcatg    5040 gatgttctct ttgctttcac taccagggtc ctcggggact ccagcggctt ggataccatg    5100
aaaaccatga tggaggagaa gtttatggag gccaacccctt ttaagaagct ctacgagccc    5160
atagtcacca ccaccaagag gaaggaggag gagcaaggcg ccgccgtcat ccagagggcc    5220
taccggaaac acatggagaa gatggtcaaa ctgaggctga aggacaggtc aagttcatcg    5280
caccaggtgt tttgcaatgg agacttgtcc agcttggatg tggccaaggt caaggttcac    5340
aatgactgaa ccctcatctc caccccctacc tcactgcctc acagcttagc ctccagcctc    5400
tggcgagcag gcggcagact cactgaacac aggccgttcg atctgtgttt ttggctgaac    5460
gaggtgacag gttggcgtcc atttttaaat gactcttgga aagatttcat gtagagagat    5520
gttagaaggg actgcaaagg acaccgacca taacggaagg cctggaggac agtccaactt    5580
acataaagat gagaaacaag aaggaaagat cccaggaaaa cttcagattg tgttctcagt    5640
acattcccca atgtgtctgt tcggtgtttt gagtatgtga cctgccacat gtagctcttt    5700
tttgcatgta cgtcaaaacc ctgcagtaag ttaatagctt gctacgggtg ttcctaccag    5760
catcacagaa ttgggtgtat gactcaaacc taaaagcatg actctgactt gtcagtcagc    5820
accccgactt tcagacgctc caatctctgt cccaggtgtc taacgaataa ataggtaaaa    5880
gaaaaaaaaa aaaaaaaaaa aaaaa                                          5905

<210> SEQ ID NO 13
<211> LENGTH: 8131
<212> TYPE: DNA
<213> ORGANISM: Homo sapiens
<220> FEATURE:
<221> NAME/KEY: misc_feature
<222> LOCATION: (6499)..(6752)
<223> OTHER INFORMATION: n is any nucleotide: a, c, g, t (u)

<400> SEQUENCE: 13
aatgtgcagg atgacaagat ggagcaaaca gtgcttgtac caccaggacc tgacagcttc      60
aacttcttca ccagagaatc tcttgcggct attgaaagac gcattgcaga agaaaaggca     120
aagaatccca accagacaa aaaagatgac gacgaaaatg gcccaaagcc aaatagtgac     180
ttggaagctg gaaagaacct tccatttatt tatggagaca ttcctccaga gatggtgtca     240
gagcccctgg aggacctgga cccctactat atcaataaga aaacttttat agtattgaat     300
aaagggaagg ccatcttccg gttcagtgcc acctctgccc tgtacatttt aactcccttc     360
aatcctctta ggaaaatagc tattaagatt ttggtacatt cattattcag catgctaatt     420
atgtgcacta ttttgacaaa ctgtgtgttt atgacaatga gtaaccctcc tgattggaca     480
aagaatgtag aatacacctt cacaggaata tatactttg aatcacttat aaaaattatt     540
gcaaggggat tctgtttaga agattttact ttccttcggg atccatggaa ctggctcgat     600
ttcactgtca ttacatttgc gtacgtcaca gagtttgtgg acctgggcaa tgtctcggca     660
```

```
ttgagaacat tcagagttct ccgagcattg aagacgattt cagtcattcc aggcctgaaa    720
accattgtgg gagccctgat ccagtctgtg aagaagctct cagatgtaat gatcctgact    780
gtgttctgtc tgagcgtatt tgctctaatt gggctgcagc tgttcatggg caacctgagg    840
aataaatgta tacaatggcc tcccaccaat gcttccttgg aggaacatag tatagaaaag    900
aatataactg tgaattataa tggtacactt ataaatgaaa ctgtctttga gtttgactgg    960
aagtcatata ttcaagattc aagatatcat tatttcctgg agggtttttt agatgcacta   1020
ctatgtggaa atagctctga tgcaggccaa tgtccagagg atatatgtg tgtgaaagct    1080 ggtagaaatc ccaattatgg ctacacaagc tttgatacct tcagttgggc tttctgtcc    1140 ttgtttcgac taatgactca ggacttctgg gaaaatcttt atcaactgac attacgtgct   1200
gctgggaaaa cgtacatgat attttttgtg ttggtcattt tcttgggctc attctaccta   1260
ataaatttga tcctggctgt ggtggccatg gcctacgagg aacagaatca ggccaccttg   1320
gaagaagcag aacagaaaga ggccgaattt cagcagatga ttgaacagct taaaaagcaa   1380
caggaggcag ctcagcaggc agcaacggca actgcctcag aacattccag agagcccagt   1440
gcagcaggca ggctctcaga cagctcatct gaagcctcta gttgagttc caagagtgct    1500 aaggaaagaa gaaatcggag gaagaaaaga aaacagaaag agcagtctgg tggggaagag   1560
aaagatgagg atgaattcca aaaatctgaa tctgaggaca gcatcaggag gaaaggtttt   1620
cgcttctcca ttgaagggaa ccgattgaca tatgaaaaga ggtactcctc cccacaccag   1680
tctttgttga gcatccgtgg ctccctattt tcaccaaggc gaaatagcag aacaagcctt   1740
ttcagcttta gagggcgtgc aaaggatgtg ggatctgaga cgacttcgc agatgatgag    1800 cacagcacct ttgaggataa cgagagccgt agagattcct tgtttgtgcc ccgacgacac   1860
ggagagagac gcaacagcaa cctgagtcag accagtaggt catcccggat gctggcagtg   1920
tttccagcga atgggaagat gcacagcact gtggattgca atggtgtggt tccttggtt    1980 ggtggacctt cagttcctac atcgcctgtt ggacagcttc tgccaggggg aacaaccact   2040
gaaactgaaa tgagaaagag aaggtcaagt tctttccacg tttccatgga ctttctagaa   2100
gatccttccc aaaggcaacg agcaatgagt atagccagca ttctaacaaa tacagtagaa   2160
gaacttgaag aatccaggca gaaatgccca ccctgttggt ataaattttc caacatattc   2220
tcaatctggg actgttctcc atattggtta aaagtgaaac atgttgtcaa cctggtcgtg   2280
atggacccat tgttgacct ggccatcacc atctgtattg tcttaaatac tcttttcatg    2340
gccatggagc actatccaat gacggaccat ttcaataatg tgcttacagt aggaaacttg   2400
gttttcactg ggatctttac agcagaaatg tttctgaaaa ttattgccat ggatccttac   2460
tattatttcc aagaaggctg gaatatcttt gacggtttta ttgtgacgct tagcctggta   2520
gaacttggac tcgccaatgt ggaaggatta tctgttctcc gttcatttcg attgctgcga   2580
gttttcaagt tggcaaaatc ttggccaacg ttaaatatgc taataaagat catcggcaat   2640
tccgtggggg ctctgggaaa tttaacccte gtcttggcca tcatcgtctt cattttttgcc   2700 gtggtcggca tgcagctctt tggtaaaagc tacaaagatt gtgtctgcaa gatcgccagt   2760
gattgtcaac tcccacaacg ctggcacatg aatgacttct ccactccttt cctgattgtg   2820
ttccgcgtgc tgtgtgggga gtggatagag accatgtggg actgtatgga ggttgctggt   2880
caagccatgt gccttactgt cttcatgatg gtcatggtga ttggaaacct agtggtcctg   2940
aatctctttc tggccttgct tctgagctca tttagtgcag acaaccttgc agccactgat   3000
gatgataatg aaatgaataa tctccaaatt gctgtggata ggatgcacaa aggagtagct   3060
```

```
tatgtgaaaa gaaaaatata tgaatttatt caacagtcct tcattaggaa acaaaagatt    3120
ttagatgaaa ttaaaccact tgatgatcta acaacaaga aagacagttg tatgtccaat     3180
catacaacag aaattgggaa agatcttgac tatcttaaag atgtaaatgg aactacaagt    3240
ggtataggaa ctggcagcag tgttgaaaaa tacattattg atgaaagtga ttacatgtca    3300
ttcataaaca accccagtct tactgtgact gtaccaattg ctgtaggaga atctgacttt    3360
gaaaatttaa acacggaaga ctttagtagt gaatcggatc tggaagaaag caaagagaaa    3420
ctgaatgaaa gcagtagctc atcagaaggt agcactgtgg acatcggcg ccctgtagaa     3480 gaacagcccg tagtggaacc tgaagaaact cttgaaccag aagcttgttt cactgaaggc    3540
tgtgtacaaa gattcaagtg ttgtcaaatc aatgtggaag aaggcagagg aaaacaatgg    3600
tggaacctga aaggacgtg tttccgaata gttgaacata actggtttga gaccttcatt      3660
gttttcatga ttctccttag tagtggtgct ctggcatttg aagatatata tattgatcag    3720
cgaaagacga ttaagacgat gttggaatat gctgacaagg ttttcactta cattttcatt    3780
ctggaaatgc ttctaaaatg ggtggcatat ggctatcaaa catatttcac caatgcctgg    3840
tgttggctgg acttcttaat tgttgatgtt tcattggtca gtttaacagc aaatgccttg    3900
ggttactcag aacttggagc catcaaatct ctcaggacac taagagctct gagacctcta    3960
agagccttat ctcgatttga agggatgagg gtggttgtga atgccctttt aggagcaatt    4020
ccatccatca tgaatgtgct tctggtttgt cttatattct ggctaatttt cagcatcatg    4080
ggcgtaaatt tgtttgctgg caaattctac cactgtatta acaccacaac tggtgacagg    4140
tttgacatcg aagacgtgaa taatcatact gattgcctaa aactaataga agaaatgag     4200 actgctcgat ggaaaaatgt gaaagtaaac tttgataatg taggatttgg gtatctctct    4260
ttgcttcaag ttgccacatt caaaggatgg atggatataa tgtatgcagc agttgattcc    4320
agaaatgtgg aactccagcc taagtatgaa gaaagtctgt acatgtatct ttactttgtt    4380
attttcatca tctttgggtc cttcttcacc ttgaacctgt ttattggtgt catcatagat    4440
aatttcaacc agcagaaaaa gaagtttgga ggtcaagaca tctttatgac agaagaacag    4500
aagaaatact ataatgcaat gaaaaaatta ggatcgaaaa aaccgcaaaa gcctatacct    4560
cgaccaggaa acaaatttca aggaatggtc tttgacttcg taaccagaca gttttttgac    4620
ataagcatca tgattctcat ctgtcttaac atggtcacaa tgatggtgga aacagatgac    4680
cagagtgaat atgtgactac cattttgtca cgcatcaatc tggtgttcat tgtgctattt    4740
actggagagt gtgtactgaa actcatctct ctacgccatt attattttac cattggatgg    4800 aatattttg attttgtggt tgtcattctc tccattgtag gtatgttct tgccgagctg     4860 atagaaaagt atttcgtgtc ccctaccctg ttccgagtga tccgtcttgc taggattggc    4920
cgaatcctac gtctgatcaa aggagcaaag gggatccgca cgctgctctt tgctttgatg    4980
atgtcccttc ctgcgttgtt taacatcggc ctcctactct tcctagtcat gttcatctac    5040
gccatctttg ggatgtccaa cttttgccta tgttaagaggg aagttgggat cgatgacatg    5100
ttcaactttg agacctttgg caacagcatg atctgcctat tccaaattac aacctctgct    5160
ggctgggatg gattgctagc acccattctc aacagtaagc cacccgactg tgaccctaat    5220
aaagttaacc ctggaagctc agttaaggga gactgtggga cccatctgt tggaatttc      5280 ttttttgtca gttacatcat catatccttc ctggttgtgg tgaacatgta catcgcggtc    5340
atcctggaga acttcagtgt tgctactgaa gaaagtgcag agcctctgag tgaggatgac    5400
```

```
tttgagatgt tctatgaggt ttgggagaag tttgatcccg atgcaactca gttcatggaa   5460
tttgaaaaat tatctcagtt tgcagctgcg cttgaaccgc ctctcaatct gccacaacca   5520
aacaaactcc agctcattgc catggatttg cccatggtga gtggtgaccg gatccactgt   5580
cttgatatct tatttgcttt tacaaagcgg gttctaggag agagtggaga gatggatgct   5640
ctacgaatac agatggaaga gcgattcatg gcttccaatc cttccaaggt ctcctatcag   5700
ccaatcacta ctactttaaa acgaaaacaa gaggaagtat ctgctgtcat tattcagcgt   5760
gcttacagac gccacctttt aaagcgaact gtaaaacaag cttcctttac gtacaataaa   5820
aacaaaatca aggtgggggc taatcttctt ataaagaag acatgataat tgacagaata   5880
aatgaaaact ctattacaga aaaaactgat ctgaccatgt ccactgcagc ttgtccacct   5940
tcctatgacc gggtgacaaa gccaattgtg gaaaacatg agcaagaagg caaagatgaa   6000
aaagccaaag ggaaataaat gaaaataaat aaaaataatt gggtgacaaa ttgtttacag   6060
cctgtgaagg tgatgtattt ttatcaacag gactccttta ggaggtcaat gccaaactga   6120 ctgttttac acaaatctcc ttaaggtcag tgcctacaat aagacagtga ccccttgtca   6180
gcaaactgtg actctgtgta aaggggagat gaccttgaca ggagattact gttctcacta   6240
ccagctgaca ctgctgaaga taagatgcac aatggctagt cagactgtag ggaccagttt   6300
caaggggtgc aaacctgtga ttttgggggtt gtttaacatg aaacacttta gtgtagtaat   6360
tgtatccact gtttgcattt caactgccac atttgtcaca tttttatgga atctgttagt   6420
ggattcatct ttttgttaat ccatgtgttt attatatgtg actattttg taaacgaagt   6480 ttctgttgag aaataggcna aggacctcta taacangtat gccacctggg gggtanggca   6540
accacatggc nctcccagct acacaaagtc gtggtttgca tgagggcatg ctgcacttag   6600
agatcatgca tgagaaaaag tcacaagaaa aacaaattct taaatttcac catatttctg   6660 ggagggtaa ttgggngata agtggaggtg ctttgttgat cttgttttgc gaaatccagc   6720
ccctanacca agtagattgt tgtgggtag gncagtaaat cttagcaggt gcaaacttca   6780
ttcaaatgtt tggagtcata aatgttatgt ttctttttgt tgtattaaaa aaaaacctga   6840
atagtgaata ttgcccctca ccctccaccg ccagaagact gaattgacca aaattactct   6900
ttataaattt ctgcttttc ctgcactttg tttagccatc ttcggctctc agcaaggttg   6960
acactgtata tgttaatgaa atgctattta ttatgtaaat agtcatttta ccctgtggtg   7020
cacgtttgag caaacaaata acgacctaag cacagtattt attgcatcaa atatgtacca   7080
caagaaatgt agagtgcaag ctttacacag gtaataaaat gtattctgta ccatttatag   7140
atagtttgga tgctatcaat gcatgtttat attaccatgc tgctgtatct ggtttctctc   7200
actgctcaga atctcattta tgagaaacca tatgtcagtg gtaaagtcaa ggaaattgtt   7260
caacagatct catttattta agtcattaag caatagtttg cagcactttta acagcttttt   7320 ggttattttt acatttaag tggataacat aggtatatag ccagactgta cagacatgtt   7380
taaaaaaaca cactgcttaa cctattaaat atgtgtttag aattttataa gcaaatataa   7440
atactgtaaa aagtcacttt atttattttt tcagcattat gtacataaat atgaagagga   7500
aattatcttc aggttgatat cacaatcact tttcttactt tctgtccata gtactttttc   7560 atgaagaaa tttgctaaat aagacatgaa aacaagactg gtagttgta gatttctgct   7620 ttttaaatta catttgctaa ttttagatta tttcacaatt ttaaggagca aaataggttc   7680
acgattcata tccaaattat gctttgcaat tggaaagggg tttaaaattt tatttatatt   7740
tctggtagta cctgtactaa ctgaattgaa ggtagtgctt atgttatttt tgttcttttt   7800
```

```
ttctgacttc ggtttatgtt ttcatttctt tggagtaatg ctgctctaga ttgttctaaa    7860
tagaatgtgg gcttcataat ttttttttcc acaaaaacag agtagtcaac ttatatagtc    7920
aattacatca ggacattttg tgtttcttac agaagcaaac cataggctcc tcttttcctt    7980
aaaactactt agataaactg tattcgtgaa ctgcatgctg gaaaatgcta ctattatgct    8040
aaataatgct aaccaacatt taaaatgtgc aaaactaata aagattacat tttttattcg    8100
aaaaaaggaa aaaaaaaaaa aaaaaaaaa a                                   8131

<210> SEQ ID NO 14
<211> LENGTH: 6586
<212> TYPE: DNA
<213> ORGANISM: Rattus norvegicus
<220> FEATURE:
<221> NAME/KEY: misc_feature
<222> LOCATION: (6539)..(6579)
<223> OTHER INFORMATION: n is any nucleotide: a, c, g, t (u)

<400> SEQUENCE: 14
ccaagatggc gcccaccgca gtcccgcccg ccgcagcctc ggcgcctctg cagtccggcc      60
gcgcctcccg ggccccgcgc tagggccgct gccgcctcgc ccgccgccgc cgccgccagc     120
tgacctgtcc cggacacata actaacgaag ctgctgcagg atgagaagat ggcagcgcgg     180
ctgctcgcac caccaggccc tgatagtttc aagcctttca cccctgagtc gctggcaaac     240
atcgagaggc gtattgccga gagcaagctc aagaaaccac caaaggcgga tggcagccac     300
cgggaggacg atgaagacag caagcccaag ccaaacagtg acctggaggc tgggaagagt     360 ttgccttttca tctacgggga catcccgcaa ggcctggttg cggttcccct ggaggacttt     420
gacccttact atttgacgca gaaaaccttt gtagtattaa acagagggaa aactctcttc     480
agatttagtg ccacacctgc cttgtacatt ttaagccctt ttaacctgat aagaagaata     540
gctattaaaa ttttgataca ctcagttttc agcatgatca tcatgtgcac catcctgacc     600
aactgtgtgt tcatgacctt tagtaaccct ccagaatggt ccaagaatgt ggagtacaca     660
ttcacaggga tttacacatt tgaatcacta gtgaaaatca tcgcaagagg tttctgcata     720
gacggcttca ccttcttgcg agacccgtgg aactggttag acttcagtgt catcatgatg     780
gcatatgtga cagagtttgt ggacctgggc aatgtctcag cgctgagaac attcagggtt     840
ctccgagctt tgaaaactat ctctgtaatt ccaggcctga gacaatcgt gggcgcccta     900 atccagtccg tgaagaagct gtcggacgtg atgatcctga cagtgttctg cctgagtgtt     960
ttcgccctga ttggcctgca gctcttcatg gggaaccttc gaaacaagtg tgtcgtgtgg    1020
cccataaact tcaacgagag ctacctggag aacggcacca gaggctttga ctgggaggaa    1080
tatatcaaca ataaaacaaa cttttacatg gttcctggca tgctagaacc cttgctctgc    1140
gggaacagtt ctgatgctgg gcaatgccca gagggattcc agtgcatgaa agcaggaagg    1200
aaccccaact acggttacac cagctttgac accttcagct gggccttctt ggcattattc    1260
cgccttatga cccaggacta ttgggagaac ttataccagc tgaccttacg agccgctggg    1320
aaaacgtaca tgatcttctt tgtcttggtc atcttcgtgg gttctttcta tctggtgaac    1380
ttgatcttgg ctgtggtggc catggcttat gaggaacaga accaggcaac actggaggag    1440
gcagagcaaa aagaggccga gttcaaggca atgctggagc aactcaagaa gcagcaggag    1500
gaggcacagg ctgctgcaat ggccacctca gcgggcactg tctcggaaga cgccattgaa    1560
gaagaagggg aagatggggt aggctctccg aggagctctt ctgaactgtc taaactcagt    1620
```

| | |
|---|---|
| tccaagagcg cgaaggagcg gcggaaccga cggaagaaga ggaagcagaa ggagctctct | 1680 |
| gaaggcgagg agaaagggga cccggagaag gtgtttaagt cagagtcgga agacggtatg | 1740 |
| agaaggaagg ccttccggct gccagacaac aggataggga ggaagttttc catcatgaat | 1800 |
| cagtcgctgc tcagcattcc aggctcgccc ttcctctccc gacataacag caaaagcagc | 1860 |
| atcttcagct tccggggacc cggtcggttc cgggaccccg gctctgagaa tgagttcgca | 1920 |
| gacgatgaac acagcaccgt ggaggagagc gagggccggc gtgactcgct cttcatcccg | 1980 |
| atccgcgccc gcgagcgccc cagcagctac agtggctaca gcggctacag ccagtgcagc | 2040 |
| cgctcgtcgc gcatcttccc cagcctgcgg cgcagcgtga agcgcaacag cacggtggac | 2100 |
| tgcaacggcg tagtgtcact catcgggccc ggctcacaca tcgggcggct cctgcctgag | 2160 |
| gtgaaaatag ataaggcagc tacgacagcg caacgactg aggtggaaat taagaagaaa | 2220 |
| ggccctggat ctcttttagt ttctatggac caactcgcct cctacggacg aaggacagaa | 2280 |
| atcaacagca taatgagcgt ggtcacaaac acgctagtgg aagagctgga agagtctcag | 2340 |
| agaaagtgcc caccgtgctg gtataagttt gccaacactt tcctcatctg ggagtgtcac | 2400 |
| ccctactgga taaaactgaa ggagatcgtg aacttaatcg tcatggaccc ttttgtagac | 2460 |
| ttagccatca ccatctgcat cgttctgaat acgctattta tggcaatgga gcaccatccc | 2520 |
| atgacaccac agttcgaaca cgtcttggcc gtaggaaatc tggtgttcac cgggatcttc | 2580 |
| acggcggaaa tgtttctgaa gctcatagcc atggaccect actattattt ccaagaaggc | 2640 |
| tggaacattt tgacggatt tattgtctcc ctcagtttaa tggagctgag tctcgcagat | 2700 |
| gtggaggggc tctcagtgct gcggtctttc cgactgctcc gagtcttcaa gctggccaag | 2760 |
| tcctggccca ccctgaacat gctgatcaag atcatcggga actccgtggg tgccctgggc | 2820 |
| aacctgaccc tggtgctggc catcatcgtc ttcatcttcg ccgtggtggg gatgcagctg | 2880 |
| tttggaaaga gttacaagga gtgcgtctgt aagatcaacc aggagtgcaa gctcccgcgc | 2940 |
| tggcacatga acgacttctt ccactccttc ctcatcgtct tccgagtgct gtgtggggag | 3000 |
| tggatcgaga ccatgtggga ctgcatggag gtggccggcc aggccatgtg cctcattgtc | 3060 |
| ttcatgatgg ttatggtcat tggcaacctg gtggtgctga atctattcct ggccttgctt | 3120 |
| ctgagctcct tcagcgcaga caacctggcg gccacagacg acgacgggga aatgaacaac | 3180 |
| ctgcagatct cagtgatccg gatcaagaag ggcgtggcct ggaccaaagt gaaggtgcac | 3240 |
| gccttcatgc aggctcactt caagcagcgg gaggcggatg aagtgaaacc cctcgacgag | 3300 |
| ctgtatgaga agaaggccaa ctgcatcgcc aaccacacgg gcgtggatat ccaccggaac | 3360 |
| ggcgacttcc agaagaacgg gaacggaacc accagcggca tcggcagcag cgtggagaag | 3420 |
| tacatcatcg acgaggacca catgtccttc attaacaacc caaacctgac cgtccgggtg | 3480 |
| cccattgctg tgggcgagtc tgacttcgag aacctcaaca cagaggatgt tagcagcgaa | 3540 |
| tcagaccctg aaggcagcaa agataaactg gacgatacca gctcctcaga aggaagtacc | 3600 |
| atcgacatca gcctgaggt ggaagaagtt cccgtggagc aacctgagga atacttggat | 3660 |
| ccggacgcct gctttacaga gggttgcgtc cagcggttca gtgctgcca ggtcaacatc | 3720 |
| gaggaaggac taggcaagtc gtggtggatc ttgcggaaaa cctgcttcct cattgtggag | 3780 |
| cacaattggt tgagaccttt catcatcttc atgattctgc tcagcagtgg cgccctggcc | 3840 |
| tttgaggaca tctacattga gcagaggaag accatccgca ccatcctgga gtatgcggac | 3900 |
| aaggtcttca cctacatctt catcctggag atgttgctca gtggacagc ctacggcttc | 3960 |
| gtcaagttct tcaccaatgc ctggtgctgg ttggacttcc tcattgtggc tgtctcttta | 4020 |

```
gtcagcctta tagctaatgc cctgggctac tcggaactag gtgccataaa gtcccttagg    4080
accctaagag ctttgagacc cttaagagcc ttatcacgat ttgaagggat gagggtggtg    4140
gtgaatgcct tggtgggcgc catccctcc atcatgaatg tgctgctggt gtgtctcatc    4200
ttctggctga ttttcagcat catgggagtt aacctgtttg cggggaaata ccactactgc    4260
tttaatgaga cttctgaaat ccggttcgaa atcgatattg tcaacaataa aacgactgt    4320 gagaagctca tggagggcaa cagcacggag atccgatgga agaatgtcaa gatcaacttt    4380
gacaatgtcg gagcagggta cctggccctt cttcaagtgg caaccttcaa aggctggatg    4440
gacatcatgt atgcggctgt agattcccga aagccagacg agcagcctga ctacgagggc    4500
aacatctaca tgtacatcta cttcgtcatc ttcatcatct tcggctcctt cttcaccctc    4560
aacctgttca tcggtgtcat catcgacaac ttcaaccagc agaagaaaaa gtttggaggt    4620
caggacatct tcatgacaga ggaacagaag aagtactaca atgccatgaa aaagctgggc    4680
tccaagaagc cacagaagcc catccccga cccttgaaca aaatccaagg gattgtcttt    4740
gatttcgtca ctcaacaagc ctttgacatt gtgatcatga tgctcatctg ccttaacatg    4800
gtgacaatga tggtggagac agacactcag agcaagcaga tggagaacat tctttactgg    4860
attaatctgg tctttgtcat cttcttcacc tgcgagtgtg tgctcaaaat gtttgccttg    4920
agacactact atttcaccat ggctggaac atctttgact ttgtggtggt catcctctcc    4980
attgtgggaa tgttcctggc tgatatcatt gagaagtact cgtctccc aaccctattc    5040 cgagttatcc gattggcccg tattgggcgc atcttgcgtc tgatcaaggg cgccaaaggg    5100
atccgcaccc tgctcttttgc cttaatgatg tcgctgcccg ccctgttcaa catcggcctc    5160
ctgctcttcc tcgtcatgtt catcttctcc attttttggca tgtccaactt cgcatacgtg    5220
aagcacgagg ccggcattga cgacatgttc aacttcgaga catttggcaa cagcatgatc    5280
tgtttgttcc agatcacaac gtctgctggc tgggatggcc tgctgctgcc aatcctgaac    5340
cgcccccctg actgcagctt ggacaaagag cacccaggga gtggcttcaa agggactgt    5400 gggaacccct cggtgggcat cttcttcttt gtgagctaca tcatcatctc cttcctgatt    5460
gtggtgaaca tgtacatcgc catcatcctg gagaacttca gcgtggccac cgaggagagc    5520
gccgaccctc tgagtgagga tgacttcgag actttctatg agatctggga gaagtttgac    5580
ccagacgcca cccagttcat cgagtactgt aagctggcag actttgccga cgccctggag    5640
cacccgctcc gagtacccaa gcccaacacc atcgagctca tcgccatgga cctgcccatg    5700
gtgagcggag atcgcatcca ctgcttggac atccttttcg ccttcaccaa gcgagtcctg    5760
ggagacagtg gggagttgga catcctgcgg cagcagatgg aggagcggtt cgtggcatcc    5820
aatccttcca agtgtcttta cgagcctatc acaaccactc tgcggcgcaa gcaggaggag    5880
gtgtctgcag tggtcctgca gcgtgcctac aggggacact ggctaggcg ggcttcatc    5940 tgcagaaaga tggcctccaa caagctggag aatggaggca cacacagaga caagaaggag    6000 agcacccgt ccacagcctc cctccctct tacgacagcg tcacaaagcc agacaaggag    6060
aagcagcagc gtgcggagga gggcagaagg gaaagagcca agaggcaaaa agaggtcagg    6120
gagtccaagt gctagaggag gggaaaggaa gcttaccccg gctgaacact ggcaagtgaa    6180
agcttgttta caaacttccg aatctcacgg atgcagagca gctgtgcaga cgctcgctgt    6240
actggaagac ctataccaaa catagtctgc ttacatgtga catggtggca tcctgagcgg    6300
tgactgctgg ggacaaagga ccctgctccc tggactcaca gatctcctat cgcttgggca    6360
```

-continued

| | |
|---|---|
| gacggttact gcatgttcca cacttagtca atgcaactta ggactaaaact aaccaggata | 6420 |
| caaaaccgag gcggctgccg ggaccagcag atcaccgctg cagccaaatg gattttattt | 6480 |
| tttcattttg ttgattctca gaagcagaaa gcatcacttt aaaagtttgt tgttcatnc | 6540 |
| aaacaatatt tgaattctta cattagttaa gctaagcanc aaaaag | 6586 |

<210> SEQ ID NO 15
<211> LENGTH: 5858
<212> TYPE: DNA
<213> ORGANISM: Mus musculus

<400> SEQUENCE: 15

| | |
|---|---|
| tggtgccctg agcctcccta gcaggaagac agtgtctgag ccaagggtga agatggagga | 60 |
| gaggtactat ccagtgatct cccagacga gaggaatttc cgccccttca ctttcgactc | 120 |
| tttggctgca atagagaagc ggatcaccat ccaaaaggag aagaagaaat ccaaagacaa | 180 |
| ggcagcaact gagccccagc ctcggcctca gctcgaccta aaggcctcca ggaagttacc | 240 |
| taagctctat ggcgacgttc cccctgacct tatagcgaag cccctggaag atctggaccc | 300 |
| attttacaaa gaccataaga cattcatggt attgaacaag aagagaacaa tctatcgctt | 360 |
| cagcgccaag agggccttgt tcattctggg gccttttaat cccatcagaa gcttcatgat | 420 |
| tcgcatctct gtccattcag tcttcagcat gttcattatc tgcacagtga tcatcaactg | 480 |
| tatgttcatg gctaataatt cttctgtgga cagtcgtcct agcagtaaca ttcccgaata | 540 |
| cgtcttcatt gggatttatg ttttagaagc tgtgattaaa atattggcaa gaggcttcat | 600 |
| tgtggatgag ttttcctacc tccgagatcc ttggaactgg ctggacttca ttgtcatcgg | 660 |
| aacagcgata gcgccttgtt ttctcggtaa caaagtcaat aatctttcca ctctacgtac | 720 |
| cttccgagtg ttgagagctc tgaaagccat ttctgtaatc tcaggtctga aggtcatcgt | 780 |
| gggtgccctg ctgcgctccg tgaagaagct agtggacgtg atggtcctca ctctcttttg | 840 |
| cctcagcatc tttgccctgg ttggtcagca gctcttcatg ggaattctga gccagaaatg | 900 |
| tattaaggac gactgtggcc ctaacgcttt tccaacaag gattgctttg taaagaaaa | 960 |
| tgatagcgag gacttcataa tgtgtggcaa ctggctcggc agaagatcct gccccgatgg | 1020 |
| ttccacgtgc aataaaaacca catttaaccc agattataat tatacaaact ttgcagctt | 1080 |
| tggctggtct tttctcgcca tgttccgggt tatgactcaa gactcctggg agaagcttta | 1140 |
| tcgacagatc cttcgcacct ccgggatcta ctttgtcttc ttcttcgtgg tcgtcatctt | 1200 |
| cctgggctct ttctacctgc ttaacttaac cctggctgtc gtcaccatgg cttacgagga | 1260 |
| acagaacaga aatgtcgctg ccgagacaga ggccaaggag aagatgtttc aggaagccca | 1320 |
| gcagctgttg agggaggaaa aggaggctct ggttgccatg ggaattgaca gaacttccct | 1380 |
| taattccctc caagcttcgt ccttttcccc aaagaagagg aagtttttg gcagtaagac | 1440 |
| aagaaagtcc ttctttatga gagggtccaa gacagcccga gcctcagcgt ccgattcaga | 1500 |
| ggacgatgcc tctaaaaacc cacaactcct tgagcaaaca aaacgactat cccagaactt | 1560 |
| gcccgtagaa ctcttgatg agcacgtgga ccccctccat aggcagagag cgctgagtgc | 1620 |
| cgtcagtatc ttaaccatca ccatgcagga acaagaaaaa tcccaggagc cttgtttccc | 1680 |
| gtgtgggaaa aacttggcat ccaagtacct ggtgtgggaa tgtagccctc cgtggctgtg | 1740 |
| cataaagaag gtcctgcaga ctatcatgac agaccccttc actgagctgg ccatcaccat | 1800 |
| ctgcatcatc gtcaatactg tcttcttggc catggaacac cacaatatgg ataactcttt | 1860 |
| aaaagacata ctgaaaatag gaaactgggt tttcactgga attttcatag cggaaatgtg | 1920 |

-continued

```
tctcaagatc attgcgctag acccttacca ctacttccgg cacggctgga acatctttga    1980
cagcattgtg gcccttgtga gtctcgctga cgtgctcttc cacaaactgt ctaaaaacct    2040
ctccttcttg gcttccctca gagtgctgag ggtcttcaag ttagccaaat cctggcccac    2100
attaaacact ctcattaaga tcatcggcca ctccgtgggt gcgctcggaa acctgactgt    2160
ggtcctaacg atcgtggtct tcatcttttc cgtggttggc atgcggctct ttggtgccaa    2220
gtttaacaag acttgctcca cctctccgga gtccctccgg cgctggcaca tgggtgattt    2280
ctaccattcc ttcctggtgg tgttccgcat cctctgtggg gagtggatcg agaacatgtg    2340
ggaatgcatg caggagatgg aaggctcccc gctgtgtgtc atcgtctttg tgctgatcat    2400
ggtggtcggg aagctcgtgg tgcttaacct cttcattgcc ttgctgctca attccttcag    2460
caatgaggaa aaggatggga acccagaagg agagaccagg aaaaccaaag tgcagctagc    2520
cctggatcgg ttcagccgag cgttctactt catggcgcgc gctcttcaga atttctgttg    2580
caagagatgc aggaggcaaa actcgccaaa gccaaatgag gcaacagaaa gctttgctgg    2640
tgagagtaga gacacagcca ccctggatac aaggtcctgg aaggagtatg attcagaaat    2700
gactctgtac actgggcagg ccggggctcc actggcccca ctggcaaaag aagaggacga    2760
tatggaatgt tgtggtgaat gtgatgcctc acctacctca cagcctagtg aggaagctca    2820
ggcctgtgac ctccctctga agaccaagcg gctccccagc ccagatgacc acggggttga    2880
aatggaagtg ttttccgaag aagatccgaa tttaaccata cagagtgctc gaaagaagtc    2940
tgatgcggca agcatgctct cagaatgcag cacaatagac ctgaatgata tctttagaaa    3000
tttacagaaa acagtttccc cccaaaagca accagatcga tgctttccca agggcctcag    3060
ttgtatcttt ctatgttgca aaacaatcaa aaaaagtcc cctgggtcc tgtggtggaa    3120 tcttcggaaa acctgctacc aaatcgtgaa gcatagctgg tttgagagct tcataatttt    3180
tgtcatcctg ctgagcagcg gagcactgat attcgaagat gtcaatcttc ccagccggcc    3240
ccaagttgaa aaattactga agtgtaccga taatatttc acatttattt ttctcctgga    3300
aatgattttg aagtgggtgg cctttggatt ccggaagtat ttcaccagtg cctggtgctg    3360
gctcgatttc ctcattgtgg tggtgtctgt gctcagcctc acgaacttac caaacttgaa    3420
gtccttccgg aatctgcgag cgctgagacc tctgcgggca ctgtctcagt ttgaaggaat    3480
gaaggttgtt gtcaatgccc tcatgagtgc catacctgcc atcctcaatg tcttgctggt    3540
ctgcctcatt ttctggctca tatttttgtat cctgggagta aattttttt ctgggaagtt    3600 tggaagatgc attaatggaa cagacataaa taaatatttc aacgcttcca atgttccaaa    3660
ccaaagccaa tgtttagtta gtaattacac gtggaaagtc ccgaatgtca actttgacaa    3720
cgtggggaat gcctaccttg ccctgctgca agtggcgacc tataagggct ggctggacat    3780
tatgaatgca gctgttgatt ccagagggaa agatgagcag ccggcctttg aggcgaatct    3840
atacgcatac ctttacttcg tggttttat catcttcggc tcattcttta ccctgaacct    3900
ctttatcggt gttattattg acaacttcaa tcagcagcag aaaaagttag gtggccaaga    3960 cattttatg acagaagaac agaagaaata ttacaatgca atgaaaaagt taggaaccaa    4020
gaagcctcaa aagcccatcc aaggcccct gaacaaatgt caagccttcg tgttcgattt    4080
ggtcacaagc caggtctttg acgtcatcat tctgggtctt attgtcacaa acatgattat    4140
catgatggct gaatctgaag gccagcccaa cgaagtgaag aaaatctttg atattctcaa    4200
catagtcttc gtggtcatct ttaccgtaga gtgtctcatc aaagtctttg ctttgaggca    4260
```

-continued

| | |
|---|---|
| acactacttc accaatggct ggaacttatt tgattgtgtg gtcgtggttc tttccatcat | 4320 |
| tagtaccttg gtttctggct tggagaacag caacgtcttc ccgcccacac tcttcaggat | 4380 |
| tgtccgcttg gctcggatcg gtcgaatcct cagactggtc cgggcggctc gaggaatcag | 4440 |
| gacactcctt ttcgcgttga tgatgtctct cccctctctc ttcaacattg gtctgcttct | 4500 |
| ctttctggtg atgttcattt atgccatctt tgggatgaac tggttttcca aagtgaagag | 4560 |
| aggctctggg attgatgaca tcttcaactt tgacactttc tcgggcagca tgctctgcct | 4620 |
| cttccagata accacttcag ccggctggga tgctctcctc aaccccatgc tggaatcaaa | 4680 |
| agcctcttgc aattcctcct cccaagagag ctgtcagcag ccgcagatag ccatagtcta | 4740 |
| cttcgtcagc tacatcatca tctccttttct cattgtggtt aacatgtaca tagctgtgat | 4800 |
| tctagagaac ttcaacacag ccacagagga gagcgaggac cccctgggcg aagacgactt | 4860 |
| tgagatcttc tatgagatct gggagaagtt tgaccccgaa gcaacacagt tcatccagta | 4920 |
| ctcatccctc tctgacttcg ccgacgcccT gcccgagccg ttgcgtgtgg ccaagcccaa | 4980 |
| caggtttcag tttctcatga tggacttgcc catggtgatg ggtgatcgcc tccattgcat | 5040 |
| ggatgttctc tttgctttca ccaccagggt cctcgggaac tccagcggct tggataccat | 5100 |
| gaaagccatg atggaggaga agttcatgga ggccaatcct ttcaagaagt tgtacgagcc | 5160 |
| cattgtcacc accacaaaga ggaaggagga ggaggaatgt gccgctgtca tccagagggc | 5220 |
| ctaccggaga cacatggaga agatgatcaa gctgaagctg aaaggcaggt caagttcatc | 5280 |
| gctccaggtg ttttgcaatg gagacttgtc tagcttggat gtgcccaaga tcaaggttca | 5340 |
| ttgtgactga aaccccccacc tgcacgccta cctcacagcc tcacagctca gcccccagcc | 5400 |
| tctggcgaac aagcggcgga ctcaccgaac aggccgttca acttgttttt ttgggtgaaa | 5460 |
| gaggtgatag gttggtgtcc attttttaaat gattcttgga aagattgaac gtcggaacat | 5520 |
| gttagaaagg actgccaagg acatccacag taacggaagg cctgaaggac agttcaaatt | 5580 |
| atgtaaagaa acgagaagga aaggtcacat gtctgttcag tttttaagtat gtgacctgcc | 5640 |
| acatgtagct cctttgcatg ttaagtgaga agtcaaaacc ctgccataag taaatagctt | 5700 |
| tgttgcaggt gtttctacca gtgctgccga tttgggtgta tggctcaaac ctgaaagcat | 5760 |
| gactctgact tgtcagcacc ccaactttca gaagctctga tctctgtcct aggtgtttga | 5820 |
| caaataaata cataaaaaaa aaaaaaaaa aaaaaaaa | 5858 |

<210> SEQ ID NO 16
<211> LENGTH: 6503
<212> TYPE: DNA
<213> ORGANISM: Bos Taurus

<400> SEQUENCE: 16

| | |
|---|---|
| cgggacccgg gccgggggac cagcagcttc ccttcaggca gcgtgaggac agcctgtgcc | 60 |
| ccagaagcag gatgagaaga tggcagcctt cctgttacct cggggcacca gcagcttccg | 120 |
| caggttcacc cgggagtctc tggcggccat cgagaagcgc atggcagaga agcaggcccg | 180 |
| gagctcggcc gcctcgcagg agagccgcga cgggctgccc gaggaggagg cgccccggcc | 240 |
| ccagctggac ctgcaagcct ccaaaaagct gccggatctc tacggcaacc caccccgaga | 300 |
| gctcatcggg gagcccctgg aggacctgga ccccttctat agcactcaaa agaccttcat | 360 |
| cgtcctgaac aaaggcaaga ccatcttccg gttcagcgcc accaacgcct tgcatgtcct | 420 |
| cagccccttc caccccatcc ggagagtggc tgtgaagatc ttggtgcatt cgctcttcag | 480 |
| catgctcatc atgtgtacca ttctgaccaa ctgcgtgttc atggcccagc acgaccctcc | 540 |

-continued

```
gccctggacc aaatatgtcg agtacatctt cactgccatc tacacctttg agtctctggt      600
caagattctg gctcgaggct tctgcctgca cgcgttcacc ttccttcggg acccgtggaa      660
ctggctggac ttcagcgtga tcatcatggc atacaccact gaatttgtgg acctgggcaa      720
tgtctcagct ttacgtacct tccgagtcct ccgggccctg aaaactatat cagtcatttc      780
aggcctgaag accatcgtgg gggccctgat ccagtctgtg aagaagctgg ccgatgtgat      840
ggtcctcacg gtcttctgcc tcagcgtctt cgccctcatc ggccttcagc tcttcatggg      900
caacctgagg cacaagtgcg tccgcaactt cacggtgctc aacggcacca acagcaccaa      960
tgcctccgtg gaggccgacg gcctgatctg gcatcgctg gacgactacc tcaacgaccc      1020
agaaaattac ctactcaaga atggcacctc tgacgtgtta ctgtgtggga cagctccga      1080
cgctgggaca tgtcctgagg ctacaggtg cctgaaggca ggtgggaacc ctgaccatgg      1140
ctacaccagc ttcgactcct tcgcctgggc cttcctcgca ctcttccgac tgatgacgca      1200
ggactgctgg gagcgcctct accagcagac cctgaggtct gcaggaagaa tctacatgat      1260
cttcttcatg ctggtcatct tcctgggctc cttctacttg gtgaacttga tcctggctgt      1320
ggtcgccatg gcctacgagg agcaaaaacca agccaccatc gcagagacag aggagaagga      1380
aaagcgattc caggaagcca tggagttgct caagaaagag caggaggccc tcgccatcag      1440
gggtgtggac accgtgtccc gcagctcctt ggagatgtcc ccattggccc cagtaaccac      1500
ccacgagaga aggagcaaga aagaaaacg aatgtcttca gggatggaag agtgtgggga      1560
cgacaagttc cccaagtccg actcagagga tggtccccga gcagtgaatc gtttcagcat      1620
cacccatggc ctcagcagga cctccatgaa gccgcgctcc agccacggga gcattttcac      1680
cttccgccga cgggacctgg gctccgagac agattttgcg gacgatgaaa acagcaccgc      1740
cggggacagt gagagccacc gcacatcact gctggtgcct tggcccctgc ggcggcctag      1800
tacccctggga cagcccagtc ccggaacctc aactcccggc cacgtgctca acggcaaaag      1860
gaacagcact gtggactgta acggggtggt ctccttgctg ggggcaggag accccgaggc      1920
cacctccccca gggagtcacc tcctccaccc tatgaagctg agcgcccccc cagacacgac      1980
cacaccatcg gaggagccgg gcaggcccca gacgctgacg ccccaggctc cgtgtgtaga      2040
cggcttcgag gagccaggag agcggcagcg agccctcagt gcagtgagcg tcctcaccag      2100
tgccctggaa gagctggagg agtctcagcg caggtgtcca ccgtgctgga tccgttttgc      2160
ccagcactac ctgatctggg agtgctgccc gctgtggatg tccattaagc agaaagtgaa      2220
gttcatggtc atggacccat ttgctgacct caccatcacc atgtgcatcg tgcttaacac      2280
gctcttcatg gcactggagc actacaacat gacgaccgaa tttgaggaga tgctgcaggt      2340
tggaaacctg gtcttcacag gaatattcac agcagagatg accttcaaga tcattgcctt      2400
ggaccctac tactacttcc agcagggctg gaacatcttc gacagcatca tcgtcatcct      2460
cagcctcatg gagctggggc tgtcccgcat gggcaatctg tcggtgcttc gctccttctg      2520
cctgcttcgg gtcttcaagc tggccaagtc ctggccacc ctgaacacac tcatcaagat      2580
cattgggaac tcagtgggcg cgctaggcaa cctgacgttg gtgctggcca tcattgtgtt      2640
catcttcgct gtggtgggca tgcagctctt tggcaagaac tactcagagc agaggcaccg      2700
tatcagtgac tcgggcctcc tgccccgctg gcacatgatg gacttcttcc atgccttcct      2760
catcatcttc cgcatcctct gtggagagtg atcgagacc atgtgggact gcatggaggt      2820
gtctgggcag tcactatgcc tgctggtctt cctgcttgtt atggtcattg gtaacctcgt      2880
```

```
ggtcctgaac ctcttcctgg ctttactgct cagctccttc agcgcagaca acctcacagc   2940
tcccgacgag gatggggaga tgaacaacct ccagctggct ctggcccgca tccagcgagg   3000
cctgcgcttc atcaagcgga ccacctggga cttctgctgc gtgctcctgc agcggccgcc   3060
tcagaagccc gcggccctcg cctcccaggg ccagctgccg ggctgtatcg ccacctccag   3120
ccccccaccc caaccagaga gcgagaaggc gcccccagcc cgcaaggaga gcgggtttga   3180
ggaaggccag cggccaggtc agggcgcacc tggggatgcc gagcctgtgt gtgtgcccat   3240
cgccgtggcc gagtcagaca cggatgaccc cgaggaggat gaggagaaca gcctaagcac   3300
agaggaagag tccagcaagc agcaggaatc ccagctggcg tccggcagcc agaggcccct   3360
cccagagccg agggtctgga gccaggtgtc ggagaccacc tcctctgggg ccgaggccag   3420
tgaggttcag gcagacttgc ggcagcagcg gcgagcagag gcccccgccc cagggtgcag   3480
tgagcttccc gaagacagtt actctgaggg gagcacggca gatatgacca acactgctga   3540
cctcctggag cagatccctg acctcggaga ggatgtcaaa gatccagagg actgcttcac   3600
tgaaggctgt gtccgccgct gtccctgctg caccgtggac accacacagg cccacgggaa   3660
ggtctggtgg aggctgcgca agacctgcta ccgcatcgtg gagcacagct ggttcgagac   3720
gttcatcatc ttcatgatcc tgctcagcag tggcgcactg gcctttgagg acatctacct   3780
ggaggagcgg aagaccatca aggtcctgct ggagtacgcc gacaagatgt tcacctacgt   3840
cttcgtgctg gagatgctcc tcaagtgggt ggcctacggc ttcaagaagt acttcaccaa   3900
cgcctggtgt tggcttgatt tcctcatcgt ggacgtcttg ctgatcagcc tggtggccaa   3960
cgccctgggc tttgctgaga tgggccccat caagtcactg cggaccttgc gtgcgctcag   4020 accccctgcga gccctgtcac gatttgaggg catgagggtt gtggttaacg ccctggtggg   4080
cgccatccca tccatcatga acgtcctcct cgtctgcctc atcttctggc tcatcttcag   4140
catcatgggc gtgaacctct cgcgggggaa gtttgggaga tgcatcaacc agaccgaggg   4200
agacctgccc ttgaactata ccatcgtgaa caacaagagc gactgtgagt ctttcaatgt   4260
gactggcgaa ttgtactgga ccaaggtgaa ggtcaacttt gacaacgtgg gggccgggta   4320 cctggcccctt ctgcaggtgg caacatttaa aggctggatg gacatcatgt atgcagctgt   4380
agactccagg gggtacgagg agcagccccca gtgggaatac aacctctaca tgtatatcta   4440
ttttgtcatc ttcatcatct ttgggtcttt cttcacccctg aacctgttca tcggtgtcat   4500
cattgacaac ttcaaccagc agaagaaaaa gttaggggggc caggacatct tcatgacaga   4560
ggagcagaag aagtactaca acgccatgaa gaagctgggc tccaagaagc cccagaagcc   4620
catcccacgg cccctgaaca gtaccaggg cttcatattc gacattgtga ccaagcaggc   4680
cttcgacgtc accatcatgt ttctcatctg cttaaacatg gtgaccatga tggtggagac   4740
agacgaccag agcccgaga aggtcaacat cttggccaag atcaacctgc tgttcgtggg   4800
catcttcaca gccgagtgta tcttcaagat ggttgccctg cgccactatt acttcaccaa   4860
cagctggaac atcttcgact tcgtggttgt catcctctcc atcgtaggca ctgtgctctc   4920
agacatcatc cagaagtact tcttctcccc gacgctcttc cgcgtcatcc gcctggcccg   4980
catcagccgc atcctcaggc tgatccgcgg ggccaagggc atccgcacgc ttctcttcgc   5040
cctcatgatg tccctgcccg cgctcttcaa catcgggctc tgctcttcc tcgtcatgtt   5100 catctactcc atcttcggca tggccaactt cgcctacgtc aagtgggagg ctggcatcga   5160
cgacatgttc aacttccaga ccttcgccaa cagcatgctg tgcctcttcc agatcaccac   5220
gtcggcgggc tgggatgggc tcctcagccc catcctcaac acggggcccc cctactgcga   5280
```

| | |
|---|---:|
| ccccaacctg cccaacagca acggctcccg gggcaactgc gggagccccg cggtgggcat | 5340 |
| cctcttcttc accacctaca tcatcatctc cttcctcatt gtggtcaaca tgtacatcgc | 5400 |
| catcatcctg gagaacttca gcgtggccac ggaggagagc acggagcccc tgagtgagga | 5460 |
| tgacttcgac atgttctacg agatctggga gaagttcgac ccggaggcca cccagttcat | 5520 |
| cgagtatttg gccctgtctg acttcgccga tgccctgtca gagccactcc ggatccccaa | 5580 |
| gcccaaccag ataagcctca tcaatatgga cctgcccatg gtgagtggag accgcatcca | 5640 |
| ctgcatggac atcctctttg ccttcaccaa gagggtcctg ggcgaatctg ggagatggaa | 5700 |
| cgccctgaag atccagatgg aggagaagtt catggcggcc aacccgtcca agatctccta | 5760 |
| cgagcccatc accaccacgc tgcggcgaaa gcacgaggag gtgtcggcca cgatcatcca | 5820 |
| gcgggccttc cgccggcacc tgctgcagcg ctccgtcaag cacgcctcct tcctctaccg | 5880 |
| ccagcaggcg ggcagcagcg gcctctcgga ggaggacgcc cccgagcagg agggcctcat | 5940 |
| cgcctacatg atgaacgaga acttctcccg ccgccccggc ccgccctcca gctcctccgt | 6000 |
| ctcctccacg tccttcccgc cctcctacga cagcgtcacc agggccacca gcgacaaccc | 6060 |
| ccaggtgcgg gcgtctgact acagcccaag cgaggatctc gccgacttcc ccccaacccc | 6120 |
| cgacagggac cgtgagtcaa tcgtgtgagc gcagcccagg ggaggggggc gccagcgcag | 6180 |
| agcatcgcgg caaacccaaa ggcagcccca gcccagcagt cgctgggccg tccgaccttt | 6240 |
| gctttgggct tcgggagtga gaggagcctc ggccccgtgg accgacaagg cagagtcctg | 6300 |
| tgcaccgcgc tgatggctgg aagcacttgg ccgagctgtc tgtctggggt taccagtcct | 6360 |
| gggggctggg tctggtccgg caacgctctg gggctctgac caccacctcc atcccagctg | 6420 |
| ctgaggcaaa atgcgaaacc gagactgtgt atgttgtgaa tgggctttca taaatttatt | 6480 |
| atatttgaaa aaaaaaaaaa aaa | 6503 |

<210> SEQ ID NO 17
<211> LENGTH: 2732
<212> TYPE: DNA
<213> ORGANISM: D. melanogaster

<400> SEQUENCE: 17

| | |
|---|---:|
| gcgacgactg tcgtcagtca gtcaatcaat cagtcagtca gtcagtcagt ccgtcagtca | 60 |
| gtcggtcagt cagttagtca gccagctagt cagttagcta gtcattcatt cagtcagtca | 120 |
| atcagtcagt gtgtcaatct gacaattgga gtttctatcc agacttcaat attttttttac | 180 |
| ctcgctcaaa acccccccact cgcactttaa ataataaaaa aaagcaggtg gtgcgtgccg | 240 |
| cgtagccgcg cgtgattctt gttgttgttt ttttttttttc ggtgaatctc ttgtaaccat | 300 |
| gtaccaaagt tctttgccgc gaaaactaaa atgaaaacga aagtgaaaat gagcgaatgg | 360 |
| cagccgcggc cacagcaatc gatccatgac acaaccagtg acaagcagtc ccccagtgaa | 420 |
| accgcatccg catccgagtc cgataccgat aaagattctg aatcggagtg agtgccgcgt | 480 |
| ccgagagcgt tccctgtcca cgtccaccat cggcggagca ggtgtgcctg aggcccacct | 540 |
| ggtggcatgg ccgccgttgc cggcctctat ggccttgggg aggatcgcca gcaccgcaag | 600 |
| aagcagcagc aacagcagca gcaccagaag gagcagctcg agcagaagga ggagcaaaag | 660 |
| aagatcgccg agcggaagct gcagctgcgg gagcagcagc tccagcgcaa ctccctcgat | 720 |
| ggttacgggt ctttgcccaa attgagcagt caagacgaag aagggggggc tggtcatggc | 780 |
| tttggtggcg gaccgcaaca ctttgaaccc attcctcacg atcatgattt ctgcgaaaga | 840 |

| | | | | |
|---|---|---|---|---|
| gtcgttataa | atgtaagcgg | attaaggttt | gagacacaac | tacgtacgtt | aaatcaattc | 900 |
| ccggacacgc | tgcttgggga | tccagctcgg | agattacggt | actttgaccc | gcttagaaat | 960 |
| gaatatttt | ttgaccgtag | tcgaccgagc | ttcgatgcga | ttttatacta | ttatcagagt | 1020 |
| ggtggccgac | tacggagacc | ggtcaatgtc | cctttagacg | tatttagtga | agaaataaaa | 1080 |
| ttttatgaat | taggtgatca | agcaattaat | aaattcagag | aggatgaagg | ctttattaaa | 1140 |
| gaggaagaaa | gaccattacc | ggataatgag | aaacagagaa | aagtctggct | gctcttcgag | 1200 |
| tatccagaaa | gttcgcaagc | cgccagagtt | gtagccataa | ttagtgtatt | tgttatattg | 1260 |
| ctatcaattg | ttatattttg | tctagaaaca | ttacccgaat | ttaagcatta | caaggtgttc | 1320 |
| aatacaacaa | caaatggcac | aaaaatcgag | gaagacgagg | tgcctgacat | cacagatcct | 1380 |
| ttcttcctta | tagaaacgtt | atgtattatt | tggtttacat | ttgaactaac | tgtcaggttc | 1440 |
| ctcgcatgtc | cgaacaaatt | aaatttctgc | agggatgtca | tgaatgttat | cgacataatc | 1500 |
| gccatcattc | cgtactttat | aacactagcg | actgtcgttg | ccgaagagga | ggatacgtta | 1560 |
| aatcttccaa | aagcgccagt | cagtccacag | gacaagtcat | cgaatcaggc | tatgtccttg | 1620 |
| gcaatattac | gagtgatacg | attagttcga | gtatttcgaa | tatttaagtt | atctaggcat | 1680 |
| tcgaagggtt | tacaaatatt | aggacgaact | ctgaaagcct | caatgcggga | attaggttta | 1740 |
| cttatattt | tcttatttat | aggcgtcgta | ctcttctcat | cggcggttta | ttttgcggaa | 1800 |
| gctggaagcg | aaaattcctt | cttcaagtcc | atacccgatg | cattttggtg | ggcggtcgtt | 1860 |
| accatgacca | ccgttggata | tggtgacatg | acaccgtcg | gcgtttgggg | caagattgtg | 1920 |
| ggatcacttt | gtgccattgc | tggcgtgctg | accatcgcac | tgccggtgcc | ggtcatcgtc | 1980 |
| agcaatttca | actacttcta | tcaccgcgaa | acggatcagg | aggagatgca | gagccagaac | 2040 |
| tttaatcacg | ttactagttg | tccatatttg | ccaggtacat | taggtcaaca | catgaagaaa | 2100 |
| tcatcattgt | ctgagtcctc | atcggatatg | atggatttgg | acgatggtgt | cgagtccacg | 2160 |
| ccgggattga | cagaaacaca | tcctggacgc | agtgcggtgg | ctccattttt | gggagcccag | 2220 |
| cagcagcagc | aacaacaacc | ggtagcatcc | tcgctgtcga | tgtcgatcga | caaacaactg | 2280 |
| cagcacccac | tgcagcacgt | gacgcagacg | caactgtacc | aacagcagca | acagcagcag | 2340 |
| cagcagcagc | aaaacggctt | caagcagcag | cagcaacaga | cgcagcagca | gctgcaacag | 2400 |
| caacagtccc | acacaataaa | cgcaagtgca | gcagcggcga | cgagcggcag | cggcagtagc | 2460 |
| ggtctcacca | tgaggcacaa | taatgccctg | gccgttagta | tcgagaccga | cgtttgacta | 2520 |
| ctggtgcaaa | agacgttgcg | tggtataaat | ttggccttga | caggagttac | gttggatgcc | 2580 |
| agaaacgact | acaaaagctg | tttatattta | atttaagtag | aacaaataac | aaaaacaaat | 2640 |
| ttaatctatt | gctaaattaa | attaaaatct | aaattaaaat | ctaaattaat | ttaattaaat | 2700 |
| tatagattta | atgataaaca | acactaaaaa | aa | | | 2732 |

<210> SEQ ID NO 18
<211> LENGTH: 3756
<212> TYPE: DNA
<213> ORGANISM: Homo sapiens

<400> SEQUENCE: 18

| | | | | |
|---|---|---|---|---|
| gtcgggatgg | aggtgagaag | acggccgtga | cgcgcgcccg | cggggccccc | tgcaccccca | 60 |
| gcagcccaca | gcgctccctg | cccccctccc | ccgcagcagc | gggccttgcc | gtcgagtgac | 120 |
| agcggcctgg | gggggcaggg | ggggcggggg | cggccggatc | agcgatgccg | gcgggcatga | 180 |
| cgaagcatgg | ctcccgctcc | accagctcgc | tgccgcccga | gcccatggag | atcgtgcgca | 240 |

-continued

```
gcaaggcgtg ctctcggcgg gtccgcctca acgtcggggg gctggcgcac gaggtactct    300
ggcgtaccct ggaccgcctg ccccgcacgc ggctgggcaa gctccgcgac tgcaacacgc    360
acgactcgct gctcgaggtg tgcgatgact acagcctcga cgacaacgag tacttctttg    420
accgccaccc gggcgccttc acctccatcc tcaacttcta ccgcactggg cgactgcaca    480
tgatggagga gatgtgcgcg ctcagcttca gccaagagct cgactactgg ggcatcgacg    540
agatctacct ggagtcctgc tgccaggccc gctaccacca agagaaagag cagatgaacg    600
aggagctcaa gcgtgaggcc gagaccctac gggagcggga aggcgaggag ttcgataaca    660
cgtgctgcgc agagaagagg aaaaaactct gggacctact ggagaagccc aattcctctg    720
tggctgccaa gatccttgcc ataatttcca tcatgttcat cgtcctctcc accattgccc    780
tgtccctcaa cacgctgcct gagctacaga gcctcgatga gttcggccag tccacagaca    840
accccccagct ggcccacgtg gaggccgtgt gcatcgcatg gttcaccatg gagtacctgc    900
tgaggttcct ctcctcgccc aagaagtgga agttcttcaa gggcccactc aatgccattg    960
acttgttggc cattctgcca tactatgtca ccattttcct caccgaatcc aacaagagcg   1020
tgctgcaatt ccagaatgtc cgccgcgtgg tccagatctt ccgcatcatg cgaattctcc   1080
gcatccttaa gcttgcacgc cactccactg gcctccagtc tctgggcttc actttgcgga   1140
ggagctacaa tgagttgggc ttgctcatcc tcttccttgc catgggcatt atgatcttct   1200
ccagccttgt cttctttgct gagaaggatg aggacgacac caagttcaaa agcatcccag   1260
cctcttctg gtgggccacc atcaccatga ctactgttgg gtatggagac atctacccca   1320
agactctcct ggggaaaatt gttgggggac tctgctgcat tgcaggagtc ctggtgattg   1380
ctcttcccat cccatcatc gtcaataact tctctgagtt ctataaggag cagaagagac   1440
aggagaaagc aatcaaacgg cgagaggctc tggagagagc caagaggaat ggcagcatcg   1500
tatccatgaa catgaaggat gcttttgccc ggagcattga gatgatggac attgtggttg   1560
agaaaaatgg ggagaatatg ggtaagaaag acaaagtaca agataaccac ttgtctccta   1620
acaaatggaa atggacaaag aggacactgt ctgaaaccag ctcaagtaag tcctttgaaa   1680
ccaaggaaca gggatcccct gaaaaagcca gatcgtcttc tagtcctcag cacctgaacg   1740
ttcagcagtt ggaagacatg tacaataaga tggccaagac ccaatcccaa cccatcctca   1800
ataccaagga gtcagcagca cagagcaaac caaaggaaga acttgaaatg gagagtatcc   1860
ccagccccgt agcccctctg cccactcgca cagaaggggt cattgacatg cgaagtatgt   1920
caagcattga tagtttcatt agctgtgcca cagacttccc tgaggccacc agattctccc   1980
acagcccttt gacatcactc cccagcaaga ctggggcag cacagcccca gaagtgggct   2040
ggcggggagc tctgggtgcc agtggtggta ggtttgtgga ggccaacccc agccctgatg   2100
ccagccagca ctctagtttc ttcatcgaga gccccaagag ttccatgaaa actaacaacc   2160
ctttgaagct ccgagcactt aaagtcaact tcatggaggg tgaccccagt ccactcctcc   2220
ccgttctagg gatgtaccat gaccctctca ggaaccgggg gagtgctgcg gctgctgtcg   2280
ctggactgga gtgtgccacg cttttggaca aggctgtgct gagcccagag tcctccatct   2340
acaccacagc aagtgctaag acacccccc ggtctcctga aaacacaca gcaatagcgt   2400
tcaactttga ggcgggtgtc caccagtaca ttgacgcaga cacagatgat gagggacagc   2460
tgctctacag tgtggactcc agcccccca aaagcctccc tgggagcacc agtccgaagt   2520
tcagcacggg gacaagatcg gagaaaaacc actttgaaag ctcccctta cccacctccc   2580
```

-continued

```
ctaagttctt aaggcagaac tgtatttact ccacagaagc attgactgga aaaggcccca      2640
gtggtcagga aaagtgcaaa cttgagaacc acatctcccc tgacgtccgt gtgttgccag      2700
ggggaggagc ccatggaagc acacgagatc agagcatctg aactgccctg ccttggagga      2760
gagacttttg ggtgaggtcc aaagaggaga gctgttcagc ttacctgcca cagagctttt      2820
ctgcatgaac tctggaacag aaaggccctg taaagccctc agagagaaga gagactccag      2880
agaaggctcc ctaagacctt gagagccatg acaggtccat cagcatgaag ttggccaagc      2940
catagggcac agcacctcct tgtaacaact ctatagccct cttggggaga tgacatgagt      3000
ggaactcaca gccaccacta ccaccacttt agacaggacc gaggccacat actcccatt       3060 ctctcgtggc tttccatctc agcctcggag ggcaacattg acagtcctcc tggcttcagc      3120
tagagaagga tgctggaaca gcggctggt gttgaaagag tgggttgacc aatttggtat       3180
tgaatgttgc ccagccaccc ctaggaacac ctgtccatca cctcctggat ggattccact      3240
gttagacagc tacagggaat gattggtcat ggggaagtct ctgcgccata agccacgatc      3300
ccagcgcaaa acccttactc aaatgtcttc attgacttcg gtatttcata gtacctgaga      3360 tttatttg agataccatc agggtgagtt gcaccacttg tactcaattc taattgcccc       3420
ctggcaatct gggaagggtt cagaaggtgg gcacccagcc aacagcatga actcagagca      3480
ttgttttagg gttggaggag gaacacgctt tctttacatc actagtgtag actcaaaaga     3540
tatgcaagtg tcaaatatgc aaaagaaata gtttattcaa agagactgtg tgttactgaa      3600
gaacagcata aaaatatgat ttttttactt gcaaaaatga aaggaaaaaa ataccacgca      3660
ttgaaatgcc cagttcagac tgaataattc ctgctgcagc aaggaaagta cctactataa      3720
tagaaattct gttttgtttt ctgtggtttt caagtt                                 3756
```

<210> SEQ ID NO 19
<211> LENGTH: 2882
<212> TYPE: DNA
<213> ORGANISM: Oryctolagus cuniculus

<400> SEQUENCE: 19

```
cctggggccg tcgggatgga ggtgagaaga cggccgtgac gcgcgcccgc gccccgcctg       60
cacgccagcg gcccgcagcg ctccctgccc ccctcgcccg ccgcagcagc gggccttgcc      120
gtcgagtgac agcggcctgg ggggcgggg ggggcggggg cggccggacc agcgatgccg       180
gcgggcatga cgaagcatgg ctcgcgctcc gccagctcgc tgccgccgga gcccatggag      240
atcgtgcgca gcaaggcgtg ctctcggcgc gtccgcctca acgtcggggg cctggcgcac      300
gaggtgctgt ggcgcaccct ggaccgcctg ccccgcacgc ggctgggcaa gctccgcgac      360
tgcaacacac acgactcgct gctcgaggtg tgtgacgact acagcctgga cgacaatgag      420
tacttcttcg accggcaccc gggcgccttc acctccatcc tcaacttcta ccgcacgggg      480
cggctgcaca tgatggagga gatgtgcgcg ctcagcttca gccaggagct tgactactgg      540
ggcatcgacg agatctacct ggagtcctgc tgccaggcgc ggtaccacca gaagaaggag      600
cagatgaatg aggaacttaa gcgcgaggcc gagacgctcc gtgagcgcga gggcgaggag      660
tttgacaaca cgtgctgcgc ggagaagcgc aagaagctgt gggacctgct ggagaagccc      720
aactcctccg tggccgccaa gatcctggcc atcatctcca tcatgttcat cgtcctctcc      780
accatcgccc tgtccctcaa cacgctgccc gagctgcaga gcctcgacga gttcggccag      840
accacggaca cccccagct ggcccacgtg gaggccgtgt gcatcgcgtg gttcaccatg      900
gagtacctgc tgcgcttcct ctcctcgccc aagaagtgga agttcttcaa gggcccgctc      960
```

```
aacgccatcg acctgctggc catcctgccc tactacgtca ccatcttcct caccgagtcc    1020
aacaagagcg tgctgcagtt ccagaacgtg cggcgcgtgg tccagatctt ccgcatcatg    1080
cgcatcctgc gcatcctgaa gctggcgcgg cactccaccg gcctccagtc cctgggcttc    1140
accctgcgga ggagctacaa cgagctgggc ttgctcatcc tcttcctcgc catgggcatc    1200
atgatcttct ccagcctcgt cttctttgcc gagaaggatg aggacgacac caagttcaaa    1260
agcatcccgg cctctttctg gtgggccacc atcaccatga cgactgtggg gtatggagac    1320
atctacccca agactctcct ggggaaaatt gtaggggggc tctgctgtat cgccggggtc    1380
ctggtgattg ctcttcccat ccccatcatc gtcaacaact tctccgagtt ctacaaggag    1440
caaaagaggc aggagaaagc gatcaagcgc agagaggctc tggagagagc caagaggaat    1500
ggcagcatcg tatccatgaa catgaaggac gctttcgccc ggagtgtcga gatgatggac    1560
atcgtggtgg agaagaacgg ggagaatttg gcgaagaagg aaaaagtaca agataaccac    1620
ttgtctccca acaagtggaa gtggacaaag aggaccctgt ccgaaaccag ctcaagtaag    1680
tcctttgaga cgaaggagca gggctcccct gagaaagcca gatcctcgtc gagtccccag    1740
cacctgaacg tgcagcagct ggaagacatg tacaacaaga tggccaagac ccagtcgcag    1800
cccgtcctca acaccaagga ggcagcggca cagagcaagc cgaaggaaga actggaaatg    1860
gagagcatcc caagcccgt ggccctctg cccactcgca ccgagggggt catcgacatg    1920
cgaagtatgt caagcattga cagctttatc agctgtgcca cggacttccc cgaagccacc    1980
aggttctccc cagccccctt ggcttccctc ccaccaagg ctggggcgg cgcggcccca    2040 gagctgggct ggcggggagc cctgggtgcc agcgggggcc ggctcgtgga ggccaacccc    2100 accccgatg ccagccacgg ctccggtttc ttcatcgaga gccccaagag ttccatgaag    2160
accaacaacc ccttgaagct ccgagcactc aaagtcaact ttatggccgg cgagcccggt    2220
ccactcctcc ctgtcctggg gatgtaccat gaccctctga ggaccgggg gggtgctgcg    2280 gctgctgtcg ccggcctgga gtgcgccaca ctcttggaca gcctgtgct gagcccagag    2340 tcctccatct acaccacagc gagtgcgagg acaccccccc ggtcgcccga aagcccaca    2400 gcaatagcat tcaatttcga ggcaggcgtc caccagtaca ttgatgccga cacagatgac    2460
gagggccagc tgctctacag tgtagactcc agccctccca agagcctcca cggggcgcc    2520 agtcccaagt gcagcatcgg ggcgaggtca gaaaagaacc actttgaaag tgccccctta    2580
cccacctccc cgaaattctt gaggcagaac tgtatttact ccacagaagg gttgactgga    2640
aaaagcctca gcggccagga aaagtgcaaa ctcgggaacc acatctcccc cgacgtccgc    2700
gtgttgccag gggaggagc tcacgggagt actcggatc agagcctctg aaccacccc     2760 ccccccacct gccgtggagg ggagactgtg gccgcggccc agagtggggg ggctgttcct    2820
ctgacctgcc atagagcttt tctgcttgaa ctctgacgca gaaaagccct gcagagcccc    2880
ca                                                                   2882

<210> SEQ ID NO 20
<211> LENGTH: 2046
<212> TYPE: DNA
<213> ORGANISM: Xenopus laevis

<400> SEQUENCE: 20
ttcggcacga gtggaaacaa gcctccttcc aagtcatgtt tgaaaggaaa tatgggcaaa      60
aacgaggaca gcgacaaaat tgtcattaat gttgggggta tcaggcatga gacctacagg     120
```

```
agtacccca  aaaccttgcc  aggtaccaga  ctctcctggc  tcactgagcc  tgatgccttt      180
agtaactttg  actatgaccc  caaaacagac  gagttcttct  ttgacagaca  ccctcaagtc      240
tttgcctgtg  tcttgaacta  ctataggact  gggaagctgc  actgtccctc  cgatgtgtgc      300
ggacccctgt  acgaggaaga  gttggctttt  tgggggattg  atgagactga  tgtggaggca      360
tgttgttgga  tgaattacag  gcagcacagg  gatgcagagg  aagccctgga  tagctttgag      420
actccagagc  cagaggagga  agaggatgga  gatctgaaaa  gactctgcct  ccaagaagat      480
ggtagaaagc  tgggctggtg  gaagaggttg  cggcctaaag  tctgggctct  ctttgaggat      540
ccctactctt  caaaatatgc  caggtatatc  gccttagctt  ccctattctt  catactcatc      600
tccatcacaa  cgttctgcct  tgagacccat  gaggcattta  atgatgtcaa  caacaagact      660
gaggtcttca  cacaaggcaa  catcactaag  acgagaccta  tattggaaat  ggagactgcg      720
ccttttctca  attacgtaga  aggcatttgt  gtgatctggt  tcacttttga  gtttctaata      780
cgtgttattt  tctgcccaga  taaaatggag  ttcattaaaa  gcagcttaaa  cattatagac      840
tttgtggcca  ttttaccctt  ctacttggaa  attggcttga  gtggcttgtc  ttccaaagca      900
gccaaggatg  ttctcggttt  ccttcgggtt  gttcgatttg  ttaggatcct  gagaatcttt      960
aagctcactc  gccatttgt   tgggctcagg  gttcttggcc  acactctacg  agccagtaca     1020
aatgagtttc  tccttcttat  catatttttg  gcacttggag  ttttaatctt  cgctaccatg     1080
atatactacg  ccgaaaggat  tggtgctgac  ccagatgaca  tcactggaag  taagcacacc     1140
tacttcaaaa  acatcccaat  agggttttgg  tgggctgtcg  taactatgac  aactttggga     1200
tatggggaca  tgtacccaat  gacttggtct  ggcatgttgg  tgggtgctct  ttgtgctttg     1260
gcaggtgtgc  taactattgc  tatgccagtc  cctgttattg  tcaacaattt  tggaatgtac     1320
tactcccttg  ctatggctaa  gcaaaagcta  ccaaagaaaa  agaataaaca  tattccccga     1380
cctcctctac  ctggatcacc  caattactgt  aaaccagact  tgcagtctcc  acatagaagt     1440
gctcaaggag  atgcctgccc  tttagctcag  gaggaaatca  ttgagatcaa  cagagcagac     1500
tccaagcaga  atggggatgc  tgcaaatgct  gcactggcca  atgaagattg  ccctactata     1560
gaccaggctc  tgtcaccaga  ggaaaagtca  cctatcacgc  ctggtgggag  ggagagatat     1620
aatcgtgatc  gtgcttgctt  cctgttgacc  acgggagact  tgcacattc   cccagatggc     1680 aacatccgca  aaggttatga  aaaatcccgg  agtctaaaca  gcatagctgg  catgagtgga     1740
aatatgctca  gactgtctcc  tatctccacc  ccatttgggt  caccatctgc  agtgagacgc     1800
ccacggtctc  ccattccctc  catcttatag  catggactca  accaactgat  aaggggaaca     1860
ttaactagta  aatacaataa  aaacaaacag  acatcaacaa  tggcaagaga  acaaaataag     1920
agactttaac  aaattctatt  attttttaag  tggttgatga  aaaatataga  ttatatgcag     1980
atatatttaa  aaaaaaagt   ttggctttta  aaaaaaaaaa  agacaaggaa  aaaaaaaaa      2040 aaaaaa                                                                     2046
```

<210> SEQ ID NO 21  
<211> LENGTH: 3591  
<212> TYPE: DNA  
<213> ORGANISM: Xenopus laevis

<400> SEQUENCE: 21

```
atggcaacct  ggaacgcatc  tcagatcatc  ttaaatagta  tgagcaacat  cattgagagc       60
ccgcaatcca  aacctcgccc  cgtaatgcgc  tccaatgggg  cgtccttatt  tattccagtc      120
actatggagg  tgccttgtga  tcaggggaca  cgtatgtggt  gggcattcct  ggcctcttct      180
```

```
atggtgacgt ttttcggagg tctgttcatt atcctggtgt ggaggacatt caaatacctg    240
tggactgtat gttgtcactg tgggggcaaa acaaggagg cacagaaagt tgtaaatgta     300
gcaagcagcc aggtcactga tgggactac aagccaactg atgataaaga agaagtagga    360
gtggcagaag ttggctggat gacatcagtt aaagactggg caggcgtgat gatttctgcc    420 cagacccta caggtcgtgt gttggttgtg acagtctttg ctctgagcat ggagcactt     480 atgatatact ttattgactc atcaaaccct attgaatctt gtcaaaactt ttacaaggat   540
ttcactcttc aaatagacat ggccttcaac atcttctttc tgctatattt tggcttgcgg   600
ttcatagctg ctaatgacaa gctttggttc tggctggaag tgaattcagt tgtggatttc   660
ttcacagtac ctcctgtgtt tgtgtcagtg tatctaaaca ggagttggct tgggctgagg   720
ttcctccgtg ctttgcggct aatacaattt tcagaaatcc tgcaattttt aaacatttta   780
aaaacaagta attccattaa gctggtgaac ctatgctcca tctttatcag tacgtggctg   840
actgcagctg gcttcatcca tttggtggag aactcaggag atccctggag aaattttgaa   900
aactcccagg accttttctta ctgggaatgt atgtacttgc tcatggtgac tatgtccaca   960
gtgggctatg gagatgttta tgcaaaaacc acccttggtc gtctcttcat ggtcttcttc  1020
attctcggcg gtttggccat gtttgccagc tacgtcccg aaatcataga gttaatagga  1080
aaccgaaaga aatatggtgg ttcatatagt gcagttagtg gacggaagca tattgtggtc  1140
tgtggtcaca tcacattaga aagcgtgtcc aacttcttga aagacttcct gcacaaggac  1200
cgagatgatg tgaatgtgga gattgtattt ttgcacaaca tatccccaaa tttggagttg  1260
gaagctttat ttaagaagca ctttactcag gtagaatttt accagggatc tgttctgaat  1320
ccacacgacc tggcaagagt taagattgag tctgcagatg cctgtctgat ccttgctaac  1380
aagtactgtg ctgaccctga tgctgaagat gcttctaaca ttatgagagt catctccatc  1440
aaaaattatc atcccaagat aagaatcatc actcagatgt tgcagtacca caataaggct  1500
cacctactta atatacccag ctggaattgg aaagatggag atgatgccat ctgccttgct  1560
gagctgaaac ttggttttat tgctcagagt tgtttggctc aaggtctatc aaccatgctg  1620
gctaatcttt tttccatgcg ttcctttatt aagattgagg aagacacctg caaaagtat   1680 tacctggaag gagtggccaa tgaaatgtat acagaatatt tatccagtgc ttttgtgggc  1740
ctttcattcc ctgcagtttg cgagttgtgc tttgtgaagt tgaaactgct aatgatagct  1800
atcgagtaca agtcagagaa aggagagagc aggatcttaa tcaatccggg taaccatatg  1860
aaaataaaag aaggtacccct gggattttttt attgccagtg atgccaaaga agtaaaacgg  1920
gccttttttt actgtaaagc atgtcatgat gacatcacag acccaaagcg gataaagaaa  1980
tgcgcctgca agagacttga agatgagcag ccatcagcct tgtcacccaa aaaaaagcaa  2040
cgaaatggag gaatgaggca ctctccaaac acttctccta acatgatgag gcatgatccc  2100
cttctcatga ctgggaatga tcaaattgat aatatggatt ctagcagtgt taaaagatat  2160
gattctactg gtatgttcca ctggtgtcca gccaaggaat tggataaagt gcttctgaca  2220
cggagtgaag ctgccatgac agtcctcagt gggcatgtgg ttgtctgcat ttttggagac  2280
atgacgtcgg cactgattgg agtacggaat tggtgatgc cactgagagc cagcaatttc  2340
cattaccatg agctgaaaca tatagtcttt gttgggtccc ttgattacat taaaagagaa  2400
tgggaaacac tacacaactt cccaaaggtg tcaatattgc ctgggacacc gttaagtcga  2460
gcagatctaa gagctgtcaa cattaacctg tgtgacatgt gcgttatcct gtcagccaac  2520
```

```
cagaataata ttgatgatac atcactgcag gacaaagaat gcattttagc atctctcaac    2580
atcaaatcta tgcagtttga tgacagcata gggctcttgc aagcaaactc tcaagggttt    2640
acacccccag gtatggagag gtcatcacct gataatagcc cactgcatgg tgttgcaaga    2700
caggcatcca taactacagg agccaacatt cccataatta cagaacttgt gaacgactca    2760
aatgttcagt tcttggacca ggatgatgat gatgacccag atacagagtt atacttgact    2820 cagcccttttg cctgtgggac agcatttgct gtcagtgtgt tggactccct catgagtgca    2880
acatacttca atgataacat cctgactctg atcagaactc tggtgactgg gggagcaaca    2940
ccagagctgg aagccctcgt tgcagaagag aatgctctgc gtggaggtta tgcaccccca    3000
caaactctag caaacagaga ccgctgtcga gtagcccaat tagccttgta tgatggacca    3060
tttgcagatt tgggggatgg tggatgttat ggagaccttt actgcaaagc attaaaaacc    3120
tacaacatgc tgtgctttgg tatataccga ctcagagatg cccacatcag cacacccagc    3180
cagtgtacca aaaggtatgt tataaccaac cctccatatg agtttgaact ggttcccaca    3240
gacctcatct tttgcctgat gcagttcgac cataatgcca gccaatcgcg agctagcctg    3300
tctcactctt cacactcctc gcactcgtct agcaaaaaaa gttcgtctgt tacctccata    3360
ctacacacag cctcagccaa ccgtcagaac agagtcaagg ctcgagattc ccgtgacaaa    3420
caaaaaatgg gccaagcaga aaagaaatgg tatacagatg aaacggaaaa caattatccc    3480
agaaacattc agattaagcc aatgagcaca catatggcta atcagattaa tcagtacaaa    3540
tcaacaagca gcttgatacc gccaatacga gaggttgaag atgaatgtta a             3591
```

US 7,888,046 B2

VOLTAGE SENSOR DOMAINS OF VOLTAGE-DEPENDENT ION CHANNEL PROTEINS AND USES THEREOF

The invention described in this application was made with funds from the National Institutes of Health, Grant Number GM43949 and GM47400. The United States government has certain rights in the invention.

CROSS REFERENCE TO RELATED APPLICATION

This application claims priority to U.S. application Ser. No. 10/377,139, filed on Mar. 1, 2003, the contents of which are incorporated by reference.

BACKGROUND OF THE INVENTION

Many cells produce electrical impulses known as electrical activities (e.g., action potential) that propagate across their surface membrane. Action potentials travel quickly, and their arrival at a distant location initiates cellular processes such as the release of neurotransmitter molecules or the contraction of muscles (Hille B. Ion Channels of Excitable Membranes. Sinauer Associates, Inc. Sunderland, Mass., 2001). These electrical impulses are the means by which living cells transfer information over large distances in short time intervals.

Action potential theory contains two key elements (Hodgkin et al. *J. Physiol.* (*Lond*) 1952, 117:500-544). The first element is that the membrane of a cell can undergo transient changes in its selective permeability to, for example, $Na^+$ and $K^+$ ions. The second element is that the permeability changes depend on membrane voltage. These two elements create an interesting situation because selective permeability to ions determines the membrane voltage, while the voltage determines the permeability.

The family of protein molecules known as the voltage-dependent cation channels typically mediate electrical activity. This family includes potassium ($K^+$), sodium ($Na^+$) and calcium ($Ca^{2+}$) selective members. The opening of a pore of a voltage-dependent ion channel, a process known as gating, is dependent upon the membrane voltage. When the pore of a voltage-dependent cation channel opens, it selectively conducts predominantly its namesake ion.

It is believed that charged amino acids, called gating charges, move through the membrane electric field before the pore opens, allowing membrane voltage to bias the equilibrium between closed and opened conformations (Armstrong et al. *J. Gen. Physiol.* 1974, 63:533-552; Sigworth et al. *Q. Rev. Biophys.* 1994, 27:1-40; and Bezanilla *Physiol. Rev.* 2000, 80:555-592).

In $K^+$ channels, the gating charge per tetrameric channel corresponds to 12-14 electron charges (3.0-3.5 charges per subunit) crossing the entire membrane voltage difference. This large gating charge gives rise to a steep change in open probability as a function of membrane voltage.

All members of the voltage-dependent cation channel family typically contain six hydrophobic segments, S1 through S6 (S1-S6) (see FIGS. 1 and 2), per subunit. Four subunits (most often identical in K+ channels and linked together as homologous 'domains' in $Na^+$ and $Ca_2^+$ channels) surround a central ion conduction pore. S5 through S6 line the pore and determine ion selectivity, while S1 through S4 form the voltage sensors. Certain charged amino acids within the voltage sensors account for most of the gating charge. These amino acids are particularly the first four arginines in S4.

Voltage-dependent ion channels are present in every cell and are involved in generation of electrical activity and information processing. As such, aberrant electrical activity can result in various conditions, such as heart arrhythmias, epilepsy, hypertension, etc.

There is a need for a composition and method for rapidly screening chemical compounds to determine whether the compounds bind to voltage-dependent ion channels.

SUMMARY OF THE INVENTION

In one embodiment, the invention relates to a composition of matter suitable for use in identifying chemical compounds that bind to voltage-dependent ion channel proteins. The composition comprises a screening protein that comprises an ion channel voltage sensor domain of the ion channel protein immobilized on a solid support.

In another embodiment, the invention relates to a kit suitable for use in identifying chemical compounds that bind to voltage-dependent ion channel proteins. The kit comprises a screening protein that comprises an ion channel voltage sensor domain of the ion channel protein and a solid support.

In another embodiment, the invention relates to a labeled screening protein suitable for use in identifying chemical compounds that bind to a voltage-dependent ion channel protein. The labeled screening protein comprising an ion channel voltage sensor domain of the ion channel protein and a detectable label.

In another embodiment, the invention relates to a method for screening for drug candidates that target voltage dependent ion channel protein. The method comprises providing a screening protein, contacting the screening protein with a chemical compound, determining whether the chemical compound binds to the screening protein, wherein chemical compounds that bind to the screening protein are drug candidates.

DETAILED DESCRIPTION OF THE INVENTION

The invention is based on the surprising discovery by the inventors that a protein comprising a voltage sensor domain of a voltage-dependent ion channel protein retains its native structure, even when immobilized on a solid support. Such a protein is herein referred to as a screening protein. If the ion channel protein is full-length, the ion selectively is retained after reconstitution into planar lipid bilayers.

In one embodiment, the invention relates to a composition of matter suitable for use in screening chemical compounds in order to identify drug candidates that bind to voltage-dependent ion channel proteins. The composition comprises a voltage-dependent ion channel protein immobilized on a solid support. The protein may contain additional components often found on proteins, such as glycosylation units. Further additional components include lipids, sulfur groups, and phosphate groups.

Voltage-dependent ion channel proteins are selective for particular ions. Such ions include, for example, potassium, sodium, and calcium. Thus, the ion channel protein can be a potassium ion channel protein, a sodium ion channel protein, or a calcium ion channel protein.

The amino acid sequence of a voltage-dependent ion channel protein across species is highly conserved. Thus, the ion channel protein can be from an organism of any species.

For example, the species can be a prokaryotic organism. Some examples of prokaryotic organisms include archaebacteria and bacteria. An example of an archaebacteria is *Aeropyrum pernix*. Examples of bacteria include *Pseudomonas aeruginosa* and *Deinococcus radiodurans*. Preferably, the ion channel protein is an *Aeropyrum pernix* (Apernix) ion channel protein, such as KvAP. The amino acid sequence of Apernix KvAP, (amino acid residues of 14-253 of SEQ. ID. NO: 1) is shown in FIG. 1.

Alternatively, the species can be a eukaryotic organism. Examples of eukaryotic organisms include invertebrates, vertebrates, and mammals. Examples of invertebrates include insects, such as *Drosophila melanogaster* and mollusks. Examples of vertebrates include mammals, reptiles, and fish. Mammals include, for example, dogs, cats, horses, sheep, cows, rats, such as *Rattus norvegicus*, mice, and primates, including humans (i.e., *Homo sapiens*). The preferred eukaryotic ion channel protein is a *Homo sapien* ion channel protein.

Figure 1:
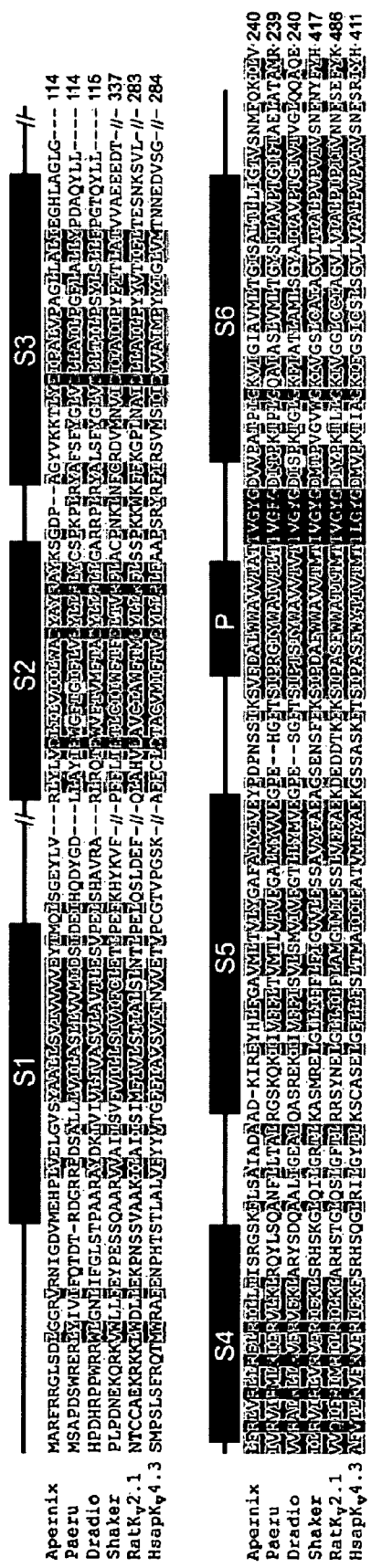
FIG. 1. Sequences of prokaryotic and eukaryotic voltage-dependent potassium (Kv) channels. Regions of high homology are colored in grey; functionally important residues are colored dark grey. Alignment was made with ClustalW followed by manual adjustment and exclusion of loops. The potassium channels are: Apernix, *Aeropyrum pernix* amino acid residues 14-253 of SEQ. ID. NO: 1 (Genbank Accession number GI: 5104624 (SEQ. ID. NO: 1); Paeru, *Pseudomonas aeruginosa* amino acid residues 1-239 of SEQ. ID. NO: 2 (Genbank Accession number GI: 15596693 (SEQ. ID. NO: 2)); Dradio, *Deinococcus radiodurans* amino acid residues 10-249 of SEQ. ID. NO: 3 (Genbank Accession number GI: 15805856 (SEQ. ID. NO: 3)); Shaker, *Drosophila melanogaster* amino acid residues 203-258 and 278-337 and amino acid residues 360-486 of SEQ. ID. NO: 4 (Genbank Accession number GI: 13432103 (SEQ. ID. NO: 4)); RatKv2.1, *Rattus norvegicus* amino acid residues 165-220 and 228-287 and 295-421 of SEQ. ID. NO: 5 (Genbank Accession number GI: 24418849 (SEQ. ID. NO: 5)); HsapKv4.3, *Homo sapiens* amino acid residues 159-214 and 225-411 of SEQ. ID. NO: 6 (Genbank Accession number GI: 5059060 (SEQ. ID. NO: 6)). The sequences corresponding to the above Genbank Accession numbers are hereby incorporated by reference.

The amino acid sequence homology for voltage-dependent potassium channel proteins of *Aeropyrum pernix, Pseudomonas aeruginosa, Deinococcus radiodurans, Drosophila melanogaster, Rattus norvegicus* and *Homo sapiens* is compared in FIG. 1. These amino acid sequence were predicted from the corresponding nucleic acid sequences disclosed in Genbank. The accession numbers are given in the brief description of FIG. 1 above.

The Genbank accession numbers of nucleic acid sequences that encode some calcium and sodium channel proteins, as well as some additional potassium channel proteins, are listed below.

Some examples of Genbank Accession numbers for voltage-dependent calcium channels include *Rattus norvegicus* calcium channel, voltage-dependent, T type, alpha 1G subunit, mRNA, Genbank Accession number GI:24429575 (SEQ. ID. NO: 7); *Homo sapiens* calcium channel, voltage-dependent, alpha 1I subunit (CACNA1I) mRNA, Genbank Accession number GI:21361076 (SEQ. ID. NO: 8); *Mus musculus* calcium channel, voltage-dependent, L type, alpha 1C subunit (Cacna1c), mRNA, Genbank Accession number GI:6753227 (SEQ. ID. NO: 9); *Homo sapiens* calcium channel, voltage-dependent, alpha 1G subunit (CACNA1G), mRNA, Genbank Accession number GI:20070162 (SEQ. ID. NO: 10); and *Caenorhabditis elegans* calcium Channel, Alpha subunit CCA-1 (210.2 kD) (cca-1) mRNA, Genbank Accession number GI:25146600 (SEQ. ID. NO: 11).

Some examples of Genbank Accession numbers for voltage-dependent sodium channels include *Rattus norvegicus* sodium channel, voltage-gated, type 11, alpha polypeptide (Scn11a), mRN, Genbank Accession number GI:15011860 (SEQ. ID. NO: 12); *Homo sapiens* sodium channel, voltage-gated, type I, alpha polypeptide (SCN1A), mRNA, Genbank Accession number GI:21914835 (SEQ. ID. NO: 13); *Rattus norvegicus* sodium channel, voltage-gated, type 8, alpha polypeptide (Scn8a), mRNA, Genbank Accession number GI:9507066 (SEQ. ID. NO: 14); *Mus musculus* sodium channel, voltage-gated, type XI, alpha polypeptide (Scn11a), mRNA, Genbank Accession number GI:6755405 (SEQ. ID. NO: 15); and *Bos taurus* mRNA for voltage-gated sodium channel alpha subunit, Genbank Accession number GI: 18477464 (SEQ. ID. NO: 16).

Some examples of Genbank Accession numbers for voltage-dependent potassium channels include *D. melanogaster* ShB1 mRNA for Shaker gene, Genbank Accession number GI:288441 (SEQ. ID. NO: 17); *Homo sapiens* potassium voltage-gated channel, Shab-related subfamily, member 1 (KCNB 1), mRNA, Genbank Accession number GI:27436972 (SEQ. ID. NO: 18); *Oryctolagus cuniculus* voltage-gated potassium channel Kv2.1 (KCNB1) mRNA, complete cds, Genbank Accession number GI:8572238 (SEQ. ID. NO: 19); *Xenopus laevis* Kv3.1 potassium channel mRNA, complete cds, Genbank Accession number GI:5817539 (SEQ. ID. NO: 20); and *Xenopus laevis* maxi-K potassium channel alpha subunit Slo mRNA, complete cds, Genbank Accession number GI: 14582151 (SEQ. ID. NO: 21).

All the sequences corresponding to the above listed Genbank Accession numbers are hereby incorporated by reference.

Figure 2B:
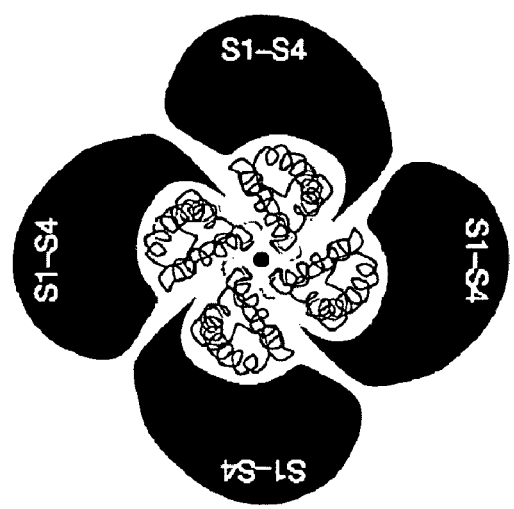
FIG. 2. Architecture of a voltage-dependent potassium channel. A) Transmembrane-spanning segments (S1-S6) are labelled; B) four subunits surround the pore. S1-S4 form the voltage sensor and S5-S6, including P, form the pore, represented by the KcsA potassium channel structure (backbone model).
Figure 2A:
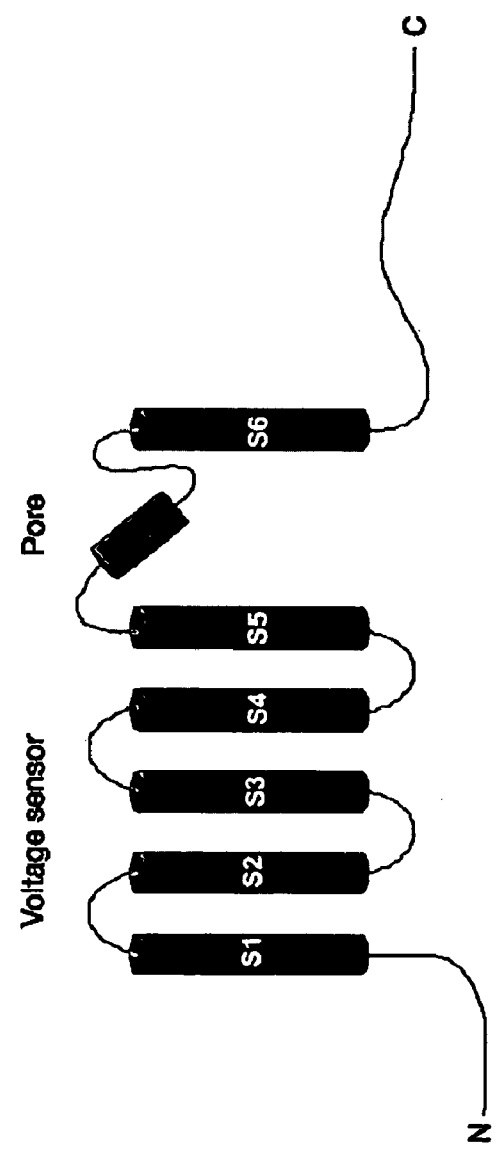

As can be seen from FIGS. 1 and 2, an entire ion channel protein comprises (i) a voltage sensor and (ii) an ion-selective pore which includes a selectivity filter. The ion voltage sensor domain comprises segments S1-S4. The ion-selective pore comprises segments S5-S6. The selective filter comprises the signature sequence amino acids between P and S6.

The screening protein useful in the present invention comprises an ion channel voltage sensor domain. For example, the screening protein can comprise the entire ion channel protein. Preferably, the screening protein includes only (i.e., consists of or consists essentially of) the ion channel voltage sensor domain, i.e., segments S1-S4, and excludes an ion conduction (i.e., selective) pore as defined above.

In a more preferred embodiment, the screening protein comprises an amino acid sequence that consists essentially of the voltage sensor domain, i.e., includes segments S1-S4, and one or more additional amino acid residues that do not change the essential nature of the voltage sensor domain. The number of additional amino acid residues is preferably relatively small. In order to constitute a relatively small number of amino acids, the number of amino acid residues should not exceed approximately 100, preferably approximately 50, and more preferably approximately 10 amino acid residues. The additional amino acid residues may, for example, be relics of the method of isolating the voltage sensor domains In addition, one or more amino acid residues may be added to the screening protein for a specific purpose. For example, amino acids may be added for the purpose of labeling the screening protein or for attachment of the screening protein to a solid support. Examples of an amino acid sequence for attaching screening proteins to a solid support include hexahistidine (e.g., $Co^{2+}$ column) and glutathione S-transferase.

The optional amino acids can be attached anywhere on the screening protein. Preferably, the optional amino acids are attached to either the N-terminus or C-terminus. The optional amino acids may also be added to any internal residue in the sequence of the screening protein, as long as the optional amino acids do not disrupt the native structure of the screening protein.

The screening protein can be a monomer or a polymer. Examples of polymers include dimers, trimers, tetramers, etc. There is no limit to the number of subunits that can polymerize, although screening proteins are typically not larger than tetramers.

The screening protein can be a functional analog of a naturally occurring voltage-dependent ion channel protein. An analog can, for example, be a substitution or deletion mutant of the ion channel protein. Substitutions and deletions can be made as long as the screening protein continues to satisfy the function of the voltage-dependent ion channel protein described herein.

Preferably, any substitutions of amino acids in a screening protein are conservative, i.e, within a group of amino acids having similar physicochemical characteristics. Amino acids may be grouped according to their physicochemical characteristics as follows:

(a) Non-polar amino acids: Ala(A) Ser(S) Thr(T) Pro(P) Gly(G);

(b) Acidic amino acids: Asn(N) Asp(D) Glu(E) Gln(Q);

(c) Basic amino acids: His(H) Arg(R) Lys(K);

(d) Hydrophobic amino acids: Met(M) Leu(L) Ile(I) Val (V); and (e) Aromatic amino acids: Phe(F) Tyr(Y) Trp(W).

During expression, the first five N-terminal amino acids may be replaced by a single leucine residue. Therefore, a screening protein where the first five N-terminal amino acids are replaced by a single leucine residue is considered to be a functional analog.

In one embodiment, the screening protein is immobilized on a solid support. The screening protein may be attached to the solid support by any method known in the art, and by any type of bond. The bond can be a covalent bond or a non-covalent bond. An example of a non-covalent bond is a hydrogen bond.

The solid support can be any support that is capable of immobilizing the screening protein. Examples of solid supports include a resin, a microtitre plate, and nitrocellulose paper. The resin may, for example, comprise cobalt, nickel, nickel-NTA agarose, and glutathione sepharose.

In another embodiment, the invention relates to a labeled screening protein suitable for use in identifying chemical compounds that bind to voltage-dependent ion channel proteins. The labeled screening protein comprises an ion channel voltage sensor domain of the ion channel protein and a detectable label. The screening protein may be any of the screening proteins described herein.

Methods for preparing a labeled protein are well known in the art. Some examples are described below.

The label may be radioactive. Some examples of useful radioactive labels include $^{32}P$, $^{125}I$, $^{131}I$, $^{35}S$, $^{14}C$, and $^{3}H$. Use of radioactive labels have been described in U.K. 2,034,323, U.S. Pat. No. 4,358,535, and U.S. Pat. No. 4,302,204.

Some examples of non-radioactive labels include enzymes and chromophores. Useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, in Ausubel, F. M. et al. (Eds.), Rotman 1961. Proc. Natl. Acad. Sci. USA 47:1981-1991, and by Current Protocols in Molecular Biology, John Wiley & Sons, Inc., New York (1999).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

In another embodiment, the invention relates to a kit suitable for use in identifying chemical compounds that bind to voltage-dependent ion channel proteins. The kit comprises a screening protein that comprises an ion channel voltage sensor domain of the ion channel protein and a solid support. The screening protein can comprise any screening protein described herein. The solid support present in the kit can be any support described herein.

The kit may further contain optional components that are helpful in preparing reagents and carrying out procedures described herein. Some examples of optional components include labels, nucleases, proteases, buffers, etc.

In another embodiment, the invention relates to a method for screening for drug candidates that target voltage-dependent ion channels. The first step in the method is providing a screening protein. Methods for preparing screening proteins by expression of the DNA encoding a screening protein in a host cell are described below.

The screening protein is contacted with a chemical compound. The chemical compound can be any molecule. Examples of molecules include biological molecules and small molecules. The chemical compounds can be a mixture of one or more different chemical compounds.

A biological molecule is any molecule which contains a polyamino acid, a polynucleotide, or a polysaccharide, and has a molecular weight greater than 450. Polyamino acids include proteins, polypeptides, and peptides.

Small molecules are typically organic compounds, including organometallic and organosilicon compounds, and the like, and generally have molecular weights of approximately 450 or less. Small molecules can further include molecules that would otherwise be considered biological molecules, except their molecular weight is not greater than 450. Thus, small molecules can include, monosaccharides, oligosaccharides, amino acids, oligopeptides, nucleotides, oligonucleotides, and their derivatives, having a molecular weight of 450 or less.

It is emphasized that a small molecule can have any molecular weight. They are merely called small molecules because they typically have molecular weights less than 450. Molecules with a molecular weight less than 450 typically do not qualify as biological molecules.

The screening protein can be contacted with the chemical compound by any method known to those in the art. Preferably, either the screening protein or the chemical compound is immobilized on a solid support.

For example, the screening protein may be immobilized on a resin. The screening protein can be contacted with the chemical compound by eluting the chemical compound through a column containing the screening protein immobilized on the resin.

Alternatively, the chemical compound may be immobilized on a microtitre plate. The screening proteins can be contacted with the chemical compound by incubating the plate with the chemical compound. Many chemical compounds may be immobilized on a plate, thereby allowing the rapid screening of the compounds.

The next step in screening is to determine whether the chemical compound binds to the screening proteins. Binding can be determined by any method known in the art.

For example, a label may be bound to the chemical compound or to the screening protein, depending on which is immobilized to the solid support. Usually, the component that is not immobilized is the component that is labeled. Thus, if the screening protein is immobilized, the chemical compound is labeled. If the chemical compound is immobilized, the screening protein is labeled.

After contacting the chemical compounds and the screening proteins as described above, detection of an immobilized label indicates the binding of screening proteins to a chemical compound. Such chemical compounds are drug candidates that target voltage dependent ion channel proteins.

Preferably, the drug candidate alters the function of the voltage dependent ion channel proteins, typically by causing the ion channel proteins either to stay open or to stay closed. For example, a drug candidate that causes the ion channel protein to stay closed inhibits the ion channel proteins. Any assay known to those in the art can be used to determine whether a drug candidate alters voltage dependent ion channels. An example of an assay is an electrophysiological assay described in, for instance, Example 2, see below.

Electrical activity, (i.e., cellular electrical activity), whether normal or abberant, is generated by voltage dependent ion channels, and therefore can be influenced by agents that affect voltage dependent ion channels. The drug candidate may be useful for treating any condition mediated by aberrant electrical activity, such as the magnitude of the resting membrane voltage, or shape and frequency of the action potential.

The condition can be, for example, asthma, hypertension, arrhythmia, epilepsy, nerve conduction abnormalities, atrial fibrillation, conditions associated with immune abnormalities due to, for instance, inappropriate lymphocyte stimulation, conditions associated with abnormalities of fluid and/or electrolyte secretion by, for example, epithelial membranes, such as in cystic fibrosis, and conditions associated with abnormal excretion by the renal system, such as in certain nephropathies, etc. Aberrant electrical activity can also initiate uptake or release of neurotransmitters, or initiate contraction of muscles.

The aberrant electrical activity can occur in any cell, organ or system in a body. Examples of cells include nerve cells, such as neurons, glial cell, and dendrites. Examples of organs and systems include heart, brain, lung, kidney, liver, muscle, digestive system, and peripheral nervous system. The muscle can be cardiac, skeletal, or smooth muscle.

The neurotransmitter can be any neurotransmitter. Examples of neurotransmitters include dopamine, epinephrine and norepinephrine.

Neurotransmitters are generally either excitatory neurotransmitters or inhibitory neurotransmitters. Excitatory neurotransmitter typically open cation channels, causing an influx of, for example, sodium, which depolarizes the postsynaptic membrane for firing an action potential. Examples of excitatory neurotransmitters include acetylcholine, glutamate, and serotonin.

Alternatively, inhibitory neurotransmitters usually suppresses firing of an action potential by keeping postsynaptic membranes polarized. Examples of inhibitory neurotransmitters include γ-aminobutyric acid and glycine.

These candidate drugs can be further tested for activity against a condition mediated by an aberrant electrical activity by methods known to those in the art. For example, the further testing can be those that are routinely done by clinicians and physicians during pre-clinical and clinical trials.

General Methods and Assays

The screening proteins may be prepared by methods that are well known in the art. Some general methods and techniques are described below. More specific methods and techniques are found in the specific examples below.

One method for producing screening proteins includes isolating or synthesizing DNA encoding the screening protein, and producing the recombinant protein by expressing the DNA, optionally in a recombinant vector, in a suitable host cell.

The proteins may also be made synthetically, i.e. from individual amino acids, or semisynthetically, i.e. from oligopeptide units or a combination of oligopeptide units and individual amino acids. Suitable methods for synthesizing proteins are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997).

Nucleic acids encoding the proteins may also be synthesized in vitro. Suitable methods for synthesizing DNA are described by Caruthers et al. 1985. *Science* 230:281-285 and DNA Structure, Part A: Synthesis and Physical Analysis of DNA, Lilley, D. M. J. and Dahlberg, J. E. (Eds.), Methods Enzymol., 211, Academic Press, Inc., New York (1992).

Nucleic acid molecules encoding the ion channel proteins may be designed or assembled from known nucleic acid sequences encoding the ion channel proteins. The nucleic acid sequences may be obtained by those skilled in the art from collections of nucleic acid sequences, such as GenBank.

Alternatively, the nucleic acid sequence may be derived from a known amino acid sequence of an ion channel protein using the genetic code, as is routine to those of skill in the art. The nucleic acid sequence may then be synthesized as described above. Similarly, the amino acid sequences of the screening proteins may be derived from the corresponding nucleic acid sequence.

The methods, constructs and host cells suitable for production of screening proteins in standard small-scale culture systems, as well as large-scale production systems, include fermenter systems, hollow fiber culture systems, tumbler systems, and suspension culture systems to name but a few.

Methods and procedures for the manipulation of nucleic acids, polymerase chain reaction (PCR) methods for amplification of nucleic acids, construction of expression vectors, transformation of host cells, and the culture of transformed cells for the production of protein are known. These and many more relevant methods may be found in a variety of laboratory manuals, texts and guides. For a general guide, see, for instance, Sambrook & Russel, (2001) Molecular Cloning, Third edition, Cold Spring Harbor Press. Other useful sources include: Ausubel et al., 1992 Short Protocols in Molecular Biology, Second edition, John Wiley & Son; Gene Expression Technology, Methods in Enzymology Vol. 185 (ed. David Goeddel et al., Academic Press, Inc., London, 1991); Gene Structure and Expression, Second Edition, J. D. Hawkins (Cambridge University Press, London, 1991); PCR Protocols: A Guide to Methods and Applications (Innis, et al. 1990, Academic Press, San Diego, Calif.); Methods in Molecular Biology (Vol. 7), Gene Transfer and Expression Protocols, (ed. E. J. Murray, 1991, The Humana Press Inc., Clifton, N.J.).

The nucleic acid encoding screening proteins may be replicated and expressed in a suitable host cell. Suitable host cells include prokaryotic host cells and eukaryotic host cells. Suitable prokaryotic host cells include *E. coli* cells which are preferred. Suitable eukaryotic host cells include yeast cells, insect cells and mammalian cells, the latter being preferred.

Screening proteins are expressed in eukaryotic hosts in preference to prokaryotic hosts in cases where the protein must be post-transcriptionally modified. Examples of post-transcriptional modification include glycosylation, phosphorylation, disulfide bond formation, oligomerization and specific cleavage of the transcribed protein product.

Prokaryotic hosts do not perform certain post-transcriptional modifications of ion channel proteins, such as for instance glycosylation. For this reason expression in eukaryotic systems is preferred despite the higher costs associated with production of biologics in eukaryotic systems as compared with the costs of biologics produced in prokaryotic host systems.

Prokaryotic host systems are preferred for expression and production of screening proteins of the invention that do not require post-transcriptional modifications that are unique to eukaryotic systems and where the screening proteins are correctly folded or may be refolded in vitro.

Many standard well known cloning and expression and isolation/purification techniques that reflect the state of the art in recombinant DNA and protein methods are described in detail in Sambrook & Russel, *Molecular Cloning: A Laboratory Manual*, Third Edition, Cold Spring Harbor Laboratory Press, Cold Spring Harbor, N.Y. (2001). Techniques for expression of cloned genes in *E. coli* and in mammalian cells is described in detail in Chapters 15 and 16-17, respectively of the Sambrook & Russel Laboratory Manual (Id).

Labels

The labels may be conjugated to the screening protein or chemical compound by methods that are well known in the art. The labels may be directly attached through a functional group on the screening protein or chemical compound. The screening protein or chemical compound either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules may be conjugated to the screening protein or chemical compound by means of coupling agents, such as dialdehydes, carbodiimides, dimaleimides, and the like.

EXAMPLES

Example 1

Preparation of *Aeropyrum pernix* KvAP

A sample of *Aeropyrum pernix* was obtained from the Japan Collection of Microorganisms. *Aeropyrum pernix* cultures were grown in a solution of autoclaved sea water supplemented with bactoyeast extract, trypticase peptone and sodium thiosulphate for three days in an oil bath maintained at 95° C.

*Aeropyrum pernix* genomic DNA was collected by standard procedures. The gene coding for KvAP starting from methionine 14 was cloned by polymerase chain reaction (PCR) amplification of the genomic DNA and inserted into the protein expression vector pQE60 (Qiagen) between NcoI and BglII restriction endonuclease sites with a thrombin cleavage site between a carboxy-terminal hexahistidine sequence and the channel.

Channel protein was expressed in XL1-blue cell cultures grown in LB medium supplemented with 10 mM BaCl2 on induction with 0.4 mM isopropyl-b-D-thiogalactopyranoside (IPTG). Expressed protein was extracted with 40 mM decylmaltoside (DM) and purified on a Talon $Co^{2+}$ affinity column (Clontech).

The protein was maintained in 5 mM DM, 20 mM Tris, pH 8.0, and 100 mM KCl. Nonspecifically bound protein was washed using 15 mM imidazole added to the above buffer, and the channel then eluted with 400 mM imidazole. Immediately after elution, 1.0 unit of thrombin (Roche) per 3.0 mg channel was added to cleave the hexahistidine sequence overnight at room temperature. Protein was concentrated to about 15 mg ml$^{-1}$ and run on a Superdex-200 (10/30) column (Pharmacia) in the above buffer.

MALDI-TOF mass spectrometry (PerSeptive Biosystems Voyager-STR) and N-terminal sequencing analysis (Rockefeller University Protein/DNA Technology Center) indicated that the KvAP protein undergoes a modification during expression in which the first five residues of the encoded construct are replaced with a single leucine residue in the expressed channel protein.

Example 2

KvAP of Prokaryotic Organism, *Aeropyrum pernix*, is Functionally Similar to Eukaryotic Kv Channels KvAP channels were expressed in *Escherichia coli*, extracted with decylmaltoside, purified and reconstituted into planar lipid bilayers of 1-palmitoyl-2-oleoyl-phosphotidylglycerol (POPG) and 1-palmitoyl-2-oleoyl-phosphotidylethanolamine (POPE) for functional studies.

KvAP channels have a large conductance—the slope of the single-channel current-voltage relationship recorded in solutions containing 150 mM KCl and 10 mM HEPES, pH 7.0, on both sides of the membrane shows a conductance of approximately 170 pS. The presence of the $K^+$ channel signature sequence indicates that the KvAP pore should be strongly selective for $K^+$ versus $Na^+$ ions.

To examine ion selectivity, the reversal potential of macroscopic tail currents in a tenfold $K^+$ gradient by substituting 135 mM NaCl for 135 mM KCl in the solution on one side of the membrane. The measured reversal potential is −56.5±1.2 mV, which is near the Nernst potential for a perfectly $K^+$ selective pore at room temperature (21° C.).

Example 3

KvAP of Prokaryotic Organism, *Aeropyrum pernix*, is Structurally Similar to Eukaryotic Kv Channels To examine the structural similarity of KvAP to eukaryotic $K^+$ channel pores, the ability of a small protein toxin from scorpion venom to inhibit the KvAP channel was examined.

Venomous animals, such as scorpions, exploit the conservation of ion-channel structure by producing a toxin that recognizes a structural feature common to an entire family of ion channels. By making many sequence variants of the same basic toxin structure, a scorpion can inhibit virtually every member of an ion channel family. The scorpion *Leiurus quinquestriatus hebraeus* specializes in a family of pore-blocking toxins, exemplified by charybdotoxin (CTX), which fit, like a key to a lock, to the pore entryway of $K^+$ channels.

CTX inhibits the KvAP channel with a dissociation constant (Kd) of about 0.4 mM. We emphasize that CTX would not bind to the KvAP channel if its pore were not very similar in structure to that of eukaryotic $K^+$ channels.

Example 4

Voltage-Dependence of KvAP is Similar to Eukaryotic Kv Channels

To determine the orientation of channels incorporated into planar lipid bilayers, we used CTX, which causes inhibition by binding only to the extracellular side. KvAP channels open in response to membrane depolarization (e.g., when the voltage of the CTX-insensitive (intracellular) side of the membrane is made positive relative to the CTX-sensitive (extracellular) side. KvAP channels are strongly voltage-dependent, opening as a function of membrane voltage, similar to Shaker and other eukaryotic neuronal Kv channels.

Example 5

Isolation of KvAP Voltage Sensor (S1-S4)

DNA for the isolated voltage sensor (from KvAP) encoding Met1 to Lys147 was cloned into a pQE60 expression vector (Qiagen) between NcoI and BglIII sites with a thrombin cleavage site followed by a C-terminal hexahistadine sequence.

Protein was expressed in *E. coli* XL1-Blue cells by induction (at $A_{600}$~1.0) with 0.4 mM isopropyl-β-D-thiogalactopyranoside (IPTG) for 4 hours at 37° C. Cells were harvested and lysed in 50 mM Tris, pH 8.0, 100 mM KCl, containing 1 μg ml$^{-1}$ Leupeptin, 1 μg ml$^{-1}$ Pepstatin, 2 μg ml$^{-1}$ Aprotinin and 1 mM PMSF (Sigma) to inhibit proteases.

Protein was then extracted from the cell lysate for 3 hours at room temperature in the above solution by adding 40 mM decylmaltoside (DM). The extracted cell lysate was centrifuged at 16,000 rpm for 20 minutes and the supernatant was collected and loaded onto a Talon $Co^{2+}$ affinity column (Clontech) equilibrated in 5 mM DM, 20 mM Tris, pH 8.0, and 100 mM KCl. Nonspecifically bound protein was washed using 10 mM imidazole added to the above buffer, and the voltage sensor domain was eluted with 300 to 400 mM imidazole in the above buffer. The isolated voltage sensor domain was then dialyzed against 100 ml of the above buffer for ~7-8 hours and transferred to 100 ml of fresh buffer for dialysis overnight. Voltage sensor domain was concentrated to ~5 mg ml$^{-1}$, calculated by 280 nm absorbance using the extinction coefficient ε=1.01 (mg ml$^{-1}$*cm)$^{-1}$ determined from amino acid analysis. Purification yields ~3 mg of voltage sensor domain protein per liter of bacterial culture.

Analysis by MALDI-TOF mass spectrometry (PerSeptive Biosystems Voyager-STR) and N-terminal sequencing indicated that the N-terminus undergoes modification during expression in which the first five residues of the encoded constructs are replaced with a single leucine residue.

Example 6

Isolated Voltage Sensor Domain Retains Native Structure and Isolates and Binds to Toxins Isolated voltage sensor was expressed and purified according to Example 5. To generate the voltage sensor domain column for isolation of toxins, 0.1 ml of $Co^{2+}$ resin was washed with water and then equilibrated with Buffer A (20 mM Tris pH 8.0, 100 mM KCl, and 10 mM DM) in an eppendorf tube by 3-4 rounds of centrifugation (500 rpm) to collect resin, careful removal of the supernatant with a pipette and resuspension of the resin in either 1 ml of water or 0.4 ml of Buffer A.

Approximately 2 mg of voltage sensor domain was added to the equilibrated resin. The resin and voltage sensor domain protein were incubated for ~15 minutes. The resin was then applied to a micro chromatography column (Biorad). Samples of the voltage sensor domain prior to addition to the resin and the flow through after addition of resin to the column was kept and later run on an SDS gel to ensure that an excess of protein has been added to the resin and saturated with protein.

The column was washed twice with 2 column volumes of Buffer A to remove any remaining unbound voltage sensor domain protein. A control column was prepared containing 0.1 ml of resin treated equivalently with the exception that instead of adding voltage sensor domain protein to the equilibrated resin, the same volume of Buffer A was added.

Venom from *Grammostola spatulata* (SpiderPharm) was diluted ten fold in Buffer A and 0.1 ml of the venom stock was applied to the column with bound S1-S4 domain or the control column. Both columns were washed to minimize non-specifically bound toxins, first in 4 column volumes Buffer A and then 4 column volumes Buffer A with 10 mM imidazole.

Remaining protein was eluted from both columns with 0.1 ml of Buffer A containing 400 mM imidazole and reduced with 50 mM DTT at 37° C. for 2 hours to improve separation by reverse phase high performance liquid chromatography (HPLC). Equal volumes of eluted, reduced protein from the two columns were run on an Agilent 1100 Series HPLC with a C-18 reverse-phase 5 μm 80 Å column using a 2 min isocratic flow of 75% mobile phase A ($H_2O$, 0.1% TFA) and 25% mobile phase B (90% acetonitrile, 10% $H_2O$, 0.1% TFA) followed by a 25%-55% mobile phase B gradient over 40 minutes. Peaks are collected and analyzed by MALDI-TOF mass spectrometry focusing on the low molecular weight range (~800-10,000 Da).

Figure 3:
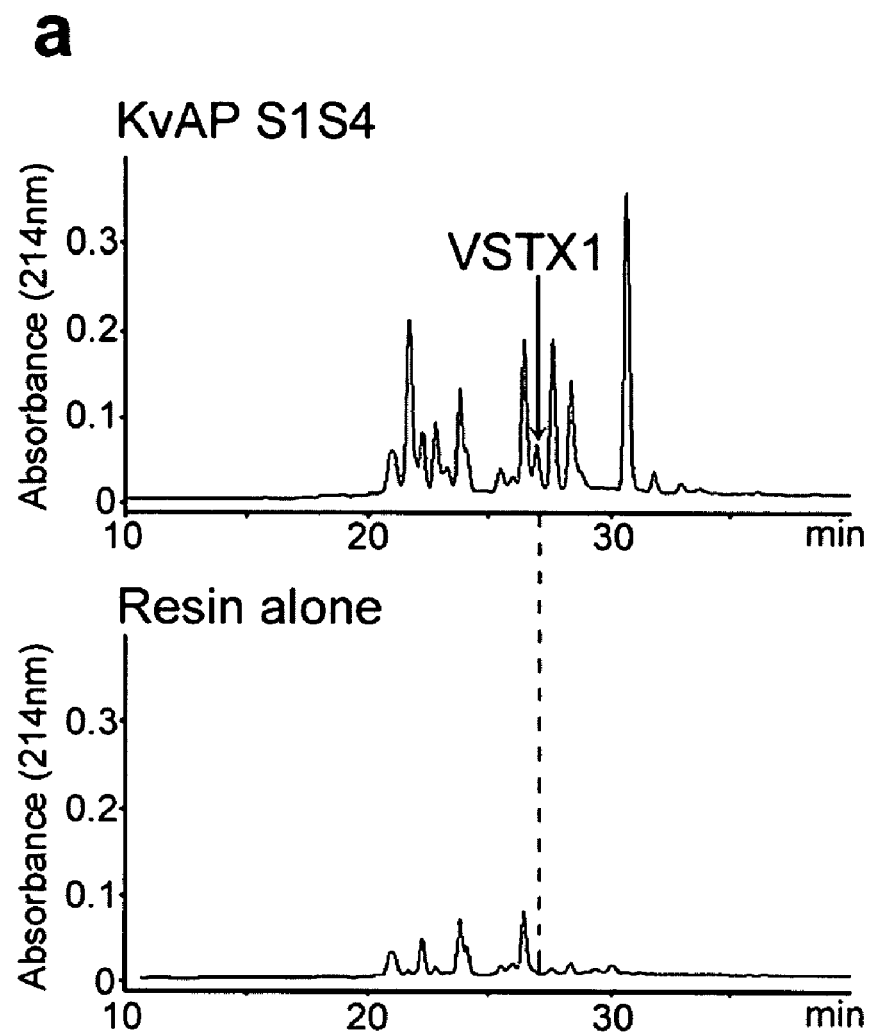
FIG. 3. Functional and structural analysis of the isolated voltage sensor domain. A) The isolated voltage sensor retains its ability to bind tarantula toxins that specifically inhibit voltage sensors. Quantitative reverse phase HPLC chromatogram of toxins eluted from a $Co^{2+}$ affinity column in the presence (top) or absence (bottom) of the voltage sensor domain. B) VSTX1, eluted at the position marked with an arrow (in FIG. 3A), binds to the domain and inhibits KvAP channel currents elicited by a +100 mV depolarization.
Figure 3B:
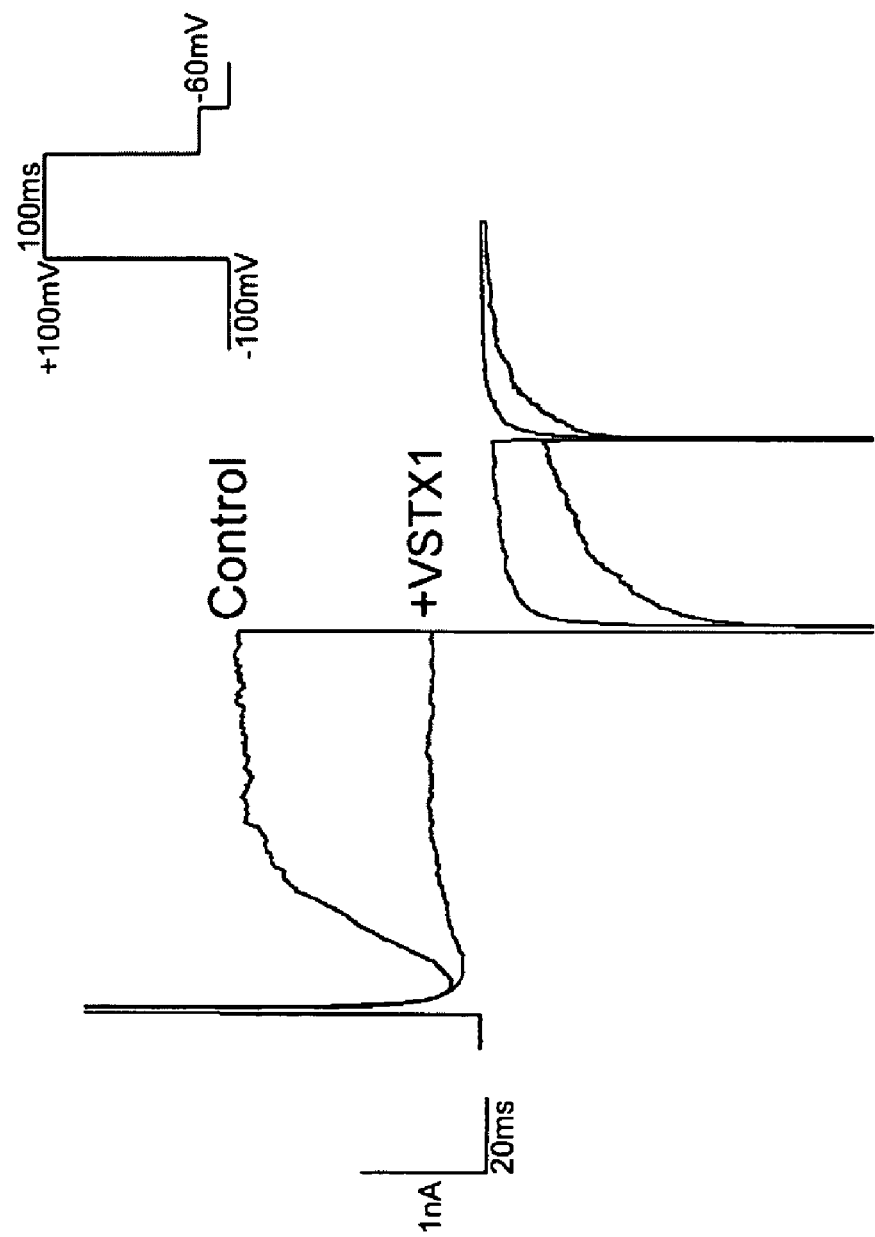

The isolate voltage sensor immobilized to a resin in the column efficiently purifies toxins from tarantula venom (FIG. 3A). These toxins also inhibit functional KvAP channels in an electrophysiological assay (FIG. 3B).

Thus, the data show that the isolated voltage sensor retains native structure due to binding of protein toxins with high affinity to the voltage sensor.

These experiments were performed with voltage-dependent ion channels from *Aeropyrum pernix*. However, due to the close homology between the amino acid sequences of voltage-dependent ion channels across species, the present invention can be applied to voltage sensor domains from any species, including *Homo sapiens*.

What is claimed is:

1. A composition of matter suitable for use in identifying chemical compounds that bind to a voltage-dependent calcium ion channel protein, the composition comprising a screening protein consisting essentially of a calcium ion channel voltage sensor domain having transmembrane segments S1-S4 of the ion channel protein immobilized on a solid support.

2. The composition of claim 1, wherein the solid support is a resin.

3. The composition of claim 2, wherein the resin comprises cobalt.

4. The composition of claim 2, wherein the resin comprises nickel.

5. The composition of claim 4, wherein the nickel is nickel-NTA agarose.

6. The composition of claim 2, wherein the resin comprises glutathione sepharose.

7. A kit suitable for use in identifying chemical compounds that bind to a voltage-dependent ion channel protein, the kit comprising a screening protein consisting essentially of a calcium ion channel voltage sensor domain having transmembrane segments S1-S4 of the ion channel protein and a solid support.

8. The kit of claim 7, wherein the solid support is a resin.

9. The kit of claim 8, wherein the resin comprises cobalt.

10. The kit of claim 8, wherein the resin comprises nickel.

11. The kit of claim 10, wherein the nickel is nickel-NTA agarose.

12. The kit of claim 8, wherein the resin comprises glutathione sepharose.

13. A labeled screening protein suitable for use in identifying chemical compounds that bind to a voltage-dependent calcium ion channel protein, the labeled screening protein consisting essentially of a calcium ion channel voltage sensor domain having transmembrane segments S1-S4 of the ion channel protein and a detectable label.

14. The labeled screening protein of claim 13, wherein the detectable label is radioactive.

15. The labeled screening protein of claim 13, wherein the detectable label is colorimetric.

16. A method for screening for drug candidates that target voltage dependent calcium ion channel protein, the method comprising:
   providing a screening protein consisting essentially of a calcium ion channel voltage sensor domain having transmembrane segments S1-S4 of the ion channel protein;
   contacting the screening protein with a chemical compound;
   determining whether the chemical compound binds to the screening protein;
   wherein chemical compounds that bind to the screening protein are drug candidates.

17. A method according to claim 16, wherein the screening protein is immobilized on a solid support.

18. A method according to claim 16, wherein the chemical compound is immobilized on a solid support.

19. A method according to claim 16, wherein the chemical compound is a biological molecule.

20. A method according to claim 19, wherein the biological molecule is a polyamino acid.

21. A method according to claim 16, wherein the chemical compound is a small molecule.

22. A method according to claim 16, wherein the drug candidate alters the target voltage dependent ion channel proteins.

* * * * *